United States Patent [19]  [11]  4,321,255
Boden  [45]  Mar. 23, 1982

[54] USE OF BRANCHED KETONES IN AUGMENTING OR ENHANCING THE AROMA OR TASTE OF FOODSTUFFS, CHEWING GUMS, TOOTHPASTES OR CHEWING TOBACCO

[75] Inventor: Richard M. Boden, Monmouth Beach, N.J.

[73] Assignee: International Flavors & Fragrances Inc., New York, N.Y.

[21] Appl. No.: 184,132

[22] Filed: Sep. 4, 1980

[51] Int. Cl.³ .............................................. A23L 1/226
[52] U.S. Cl. .......................................... 424/49; 426/3; 426/534; 252/522 R; 131/276; 568/417
[58] Field of Search ..................... 426/534, 3; 568/417; 424/49

[56]  References Cited
U.S. PATENT DOCUMENTS 2,246,032  6/1941  Bent et al. ........................ 568/417 X
2,870,210  1/1959  Surmatis et al. ................ 426/534 X
4,234,518  11/1980  Yoshida et al. ................. 426/534 X Primary Examiner—Joseph M. Golian
Attorney, Agent, or Firm—Arthur L. Liberman

[57]  ABSTRACT

Described is the use in augmenting or enhancing the aroma or taste of foodstuffs, chewing gums, toothpastes or chewing tobaccos comprising the step of adding to a foodstuff, toothpaste, chewing gum or chewing tobacco an aroma or taste augmenting or enhancing quantity of at least one acylated diisoamylene derivative defined according to the structure:

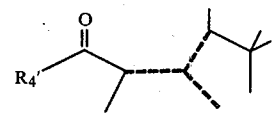

wherein $R_4'$ represents $C_1$–$C_3$ lower alkyl; wherein one of the dashed lines is a carbon-carbon double bond and the other of the dashed lines represent carbon-carbon single bonds.

5 Claims, 34 Drawing Figures

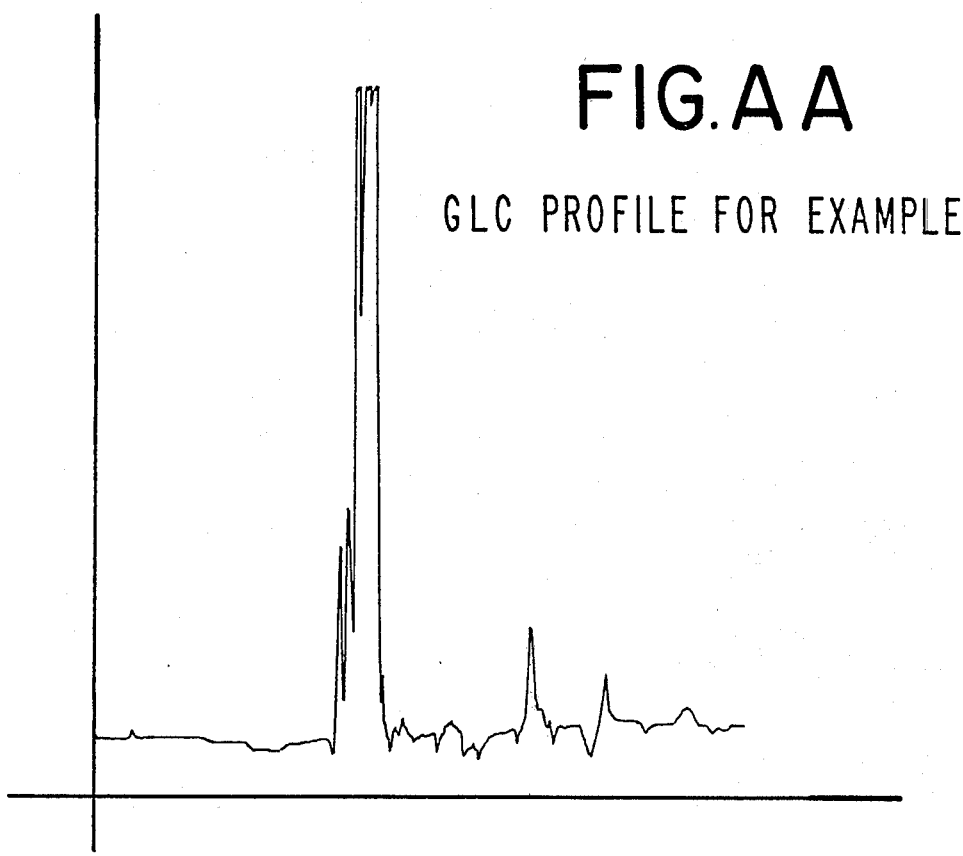
FIG. AA
GLC PROFILE FOR EXAMPLE A.
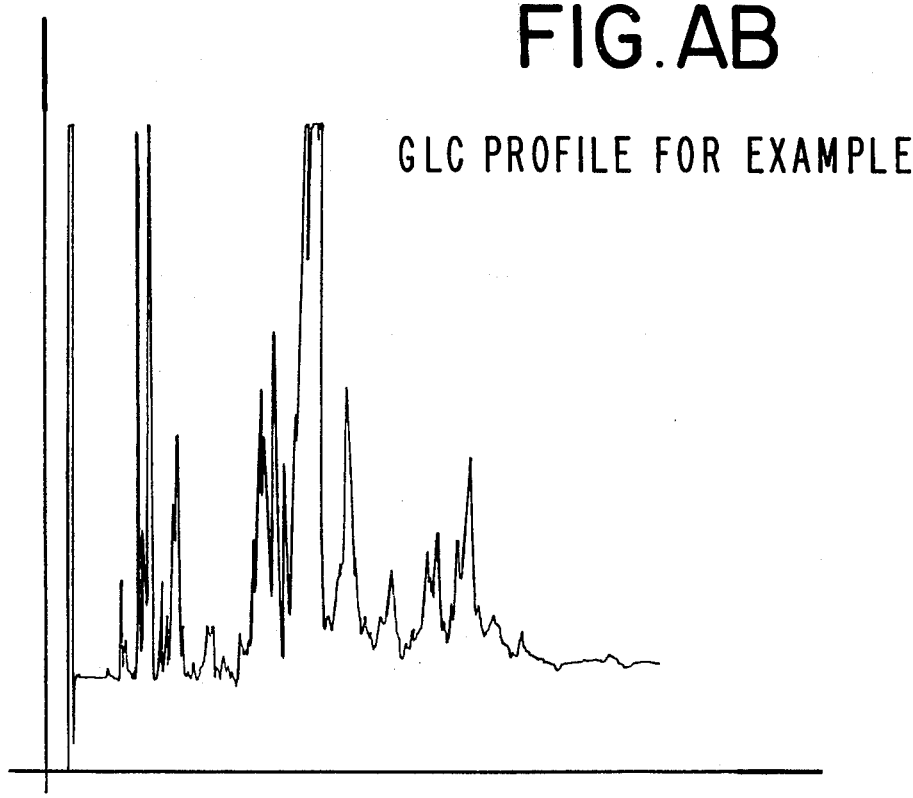
FIG. AB
GLC PROFILE FOR EXAMPLE A

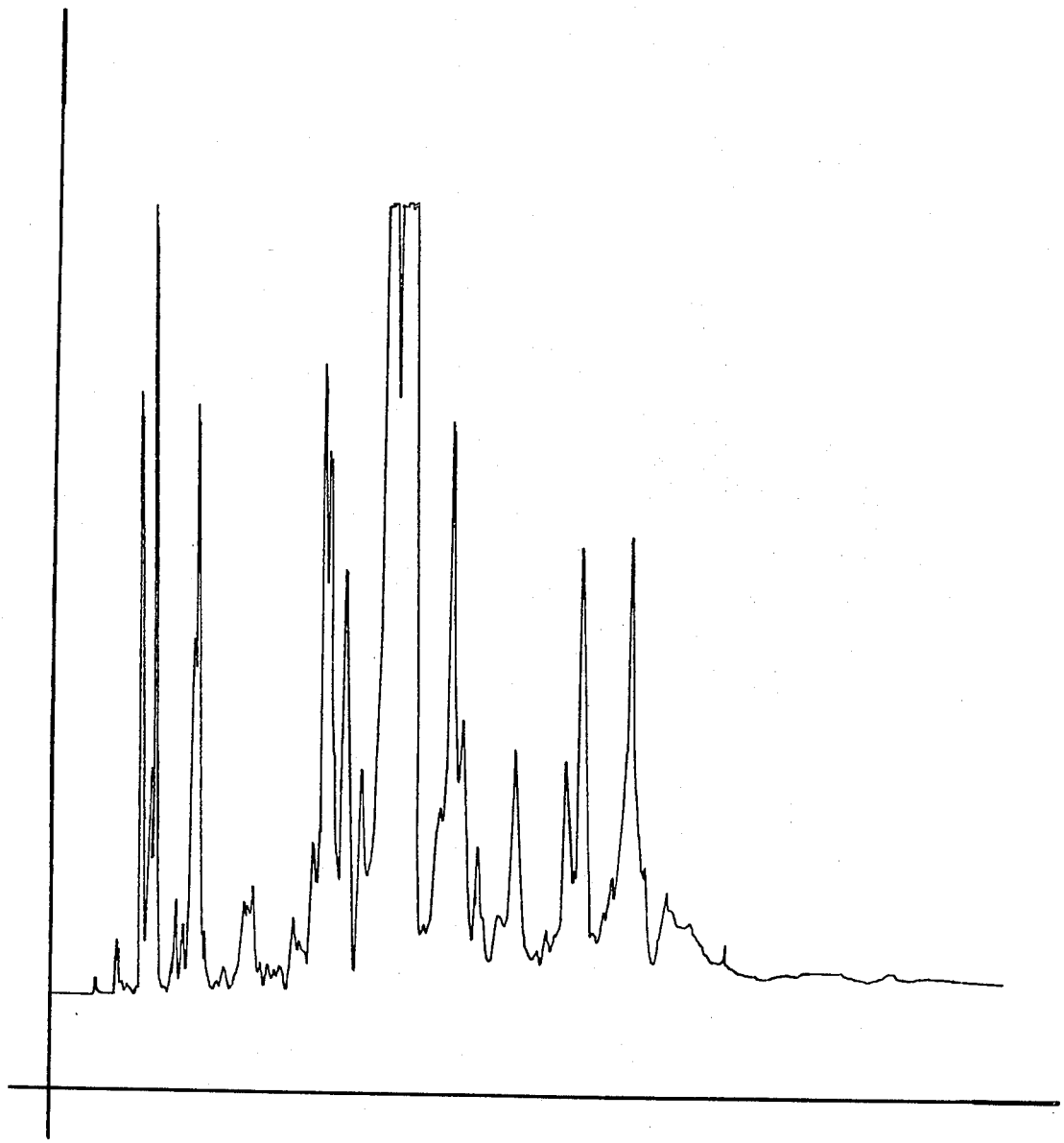
GLC PROFILE FOR EXAMPLE A.
FIG.AC

FIG.AD
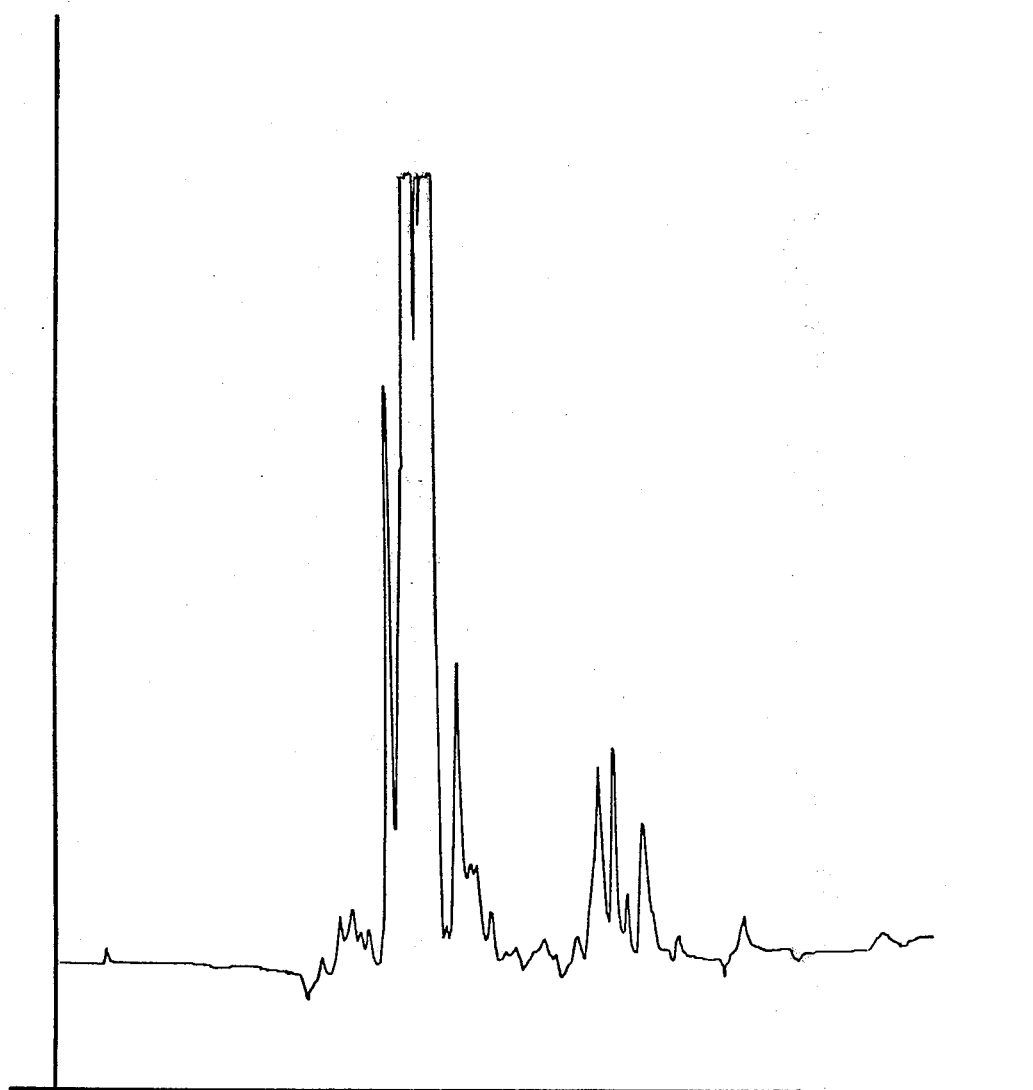
GLC PROFILE FOR EXAMPLE A.
CRUDE PRODUCT

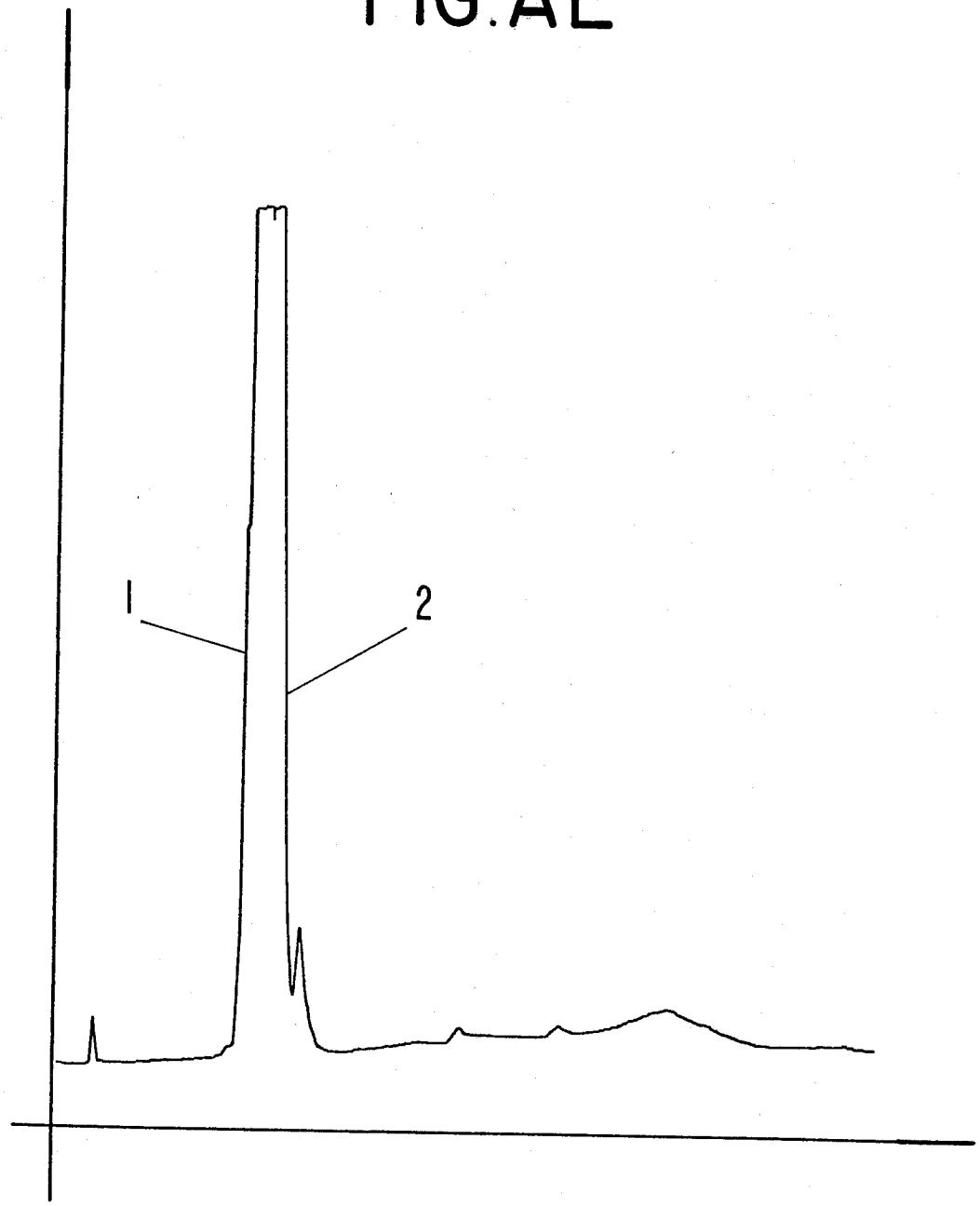
FIG.AE
GLC PROFILE FOR EXAMPLE A.
DISTILLATION PRODUCT

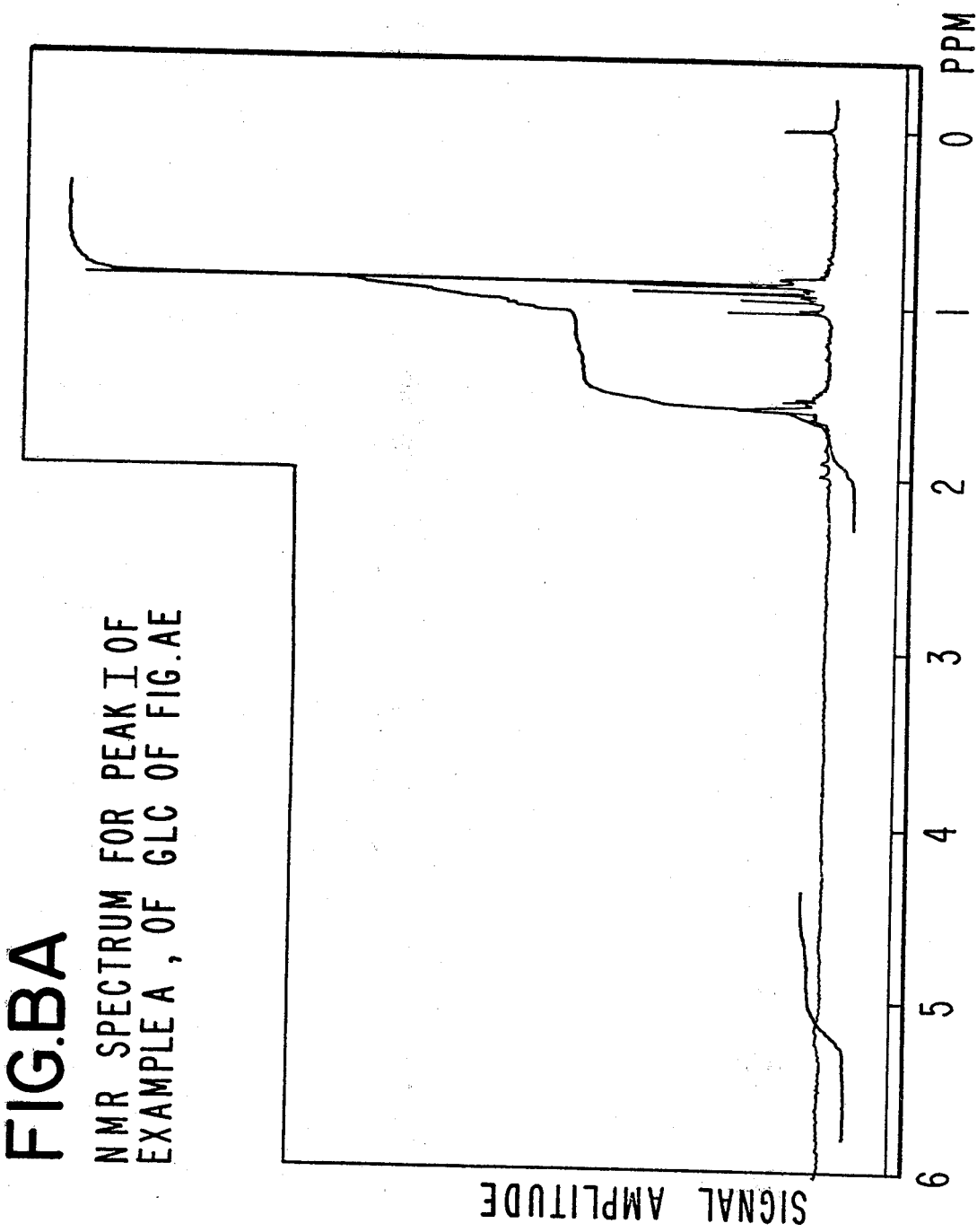
FIG.BA
NMR SPECTRUM FOR PEAK I OF EXAMPLE A, OF GLC OF FIG.AE

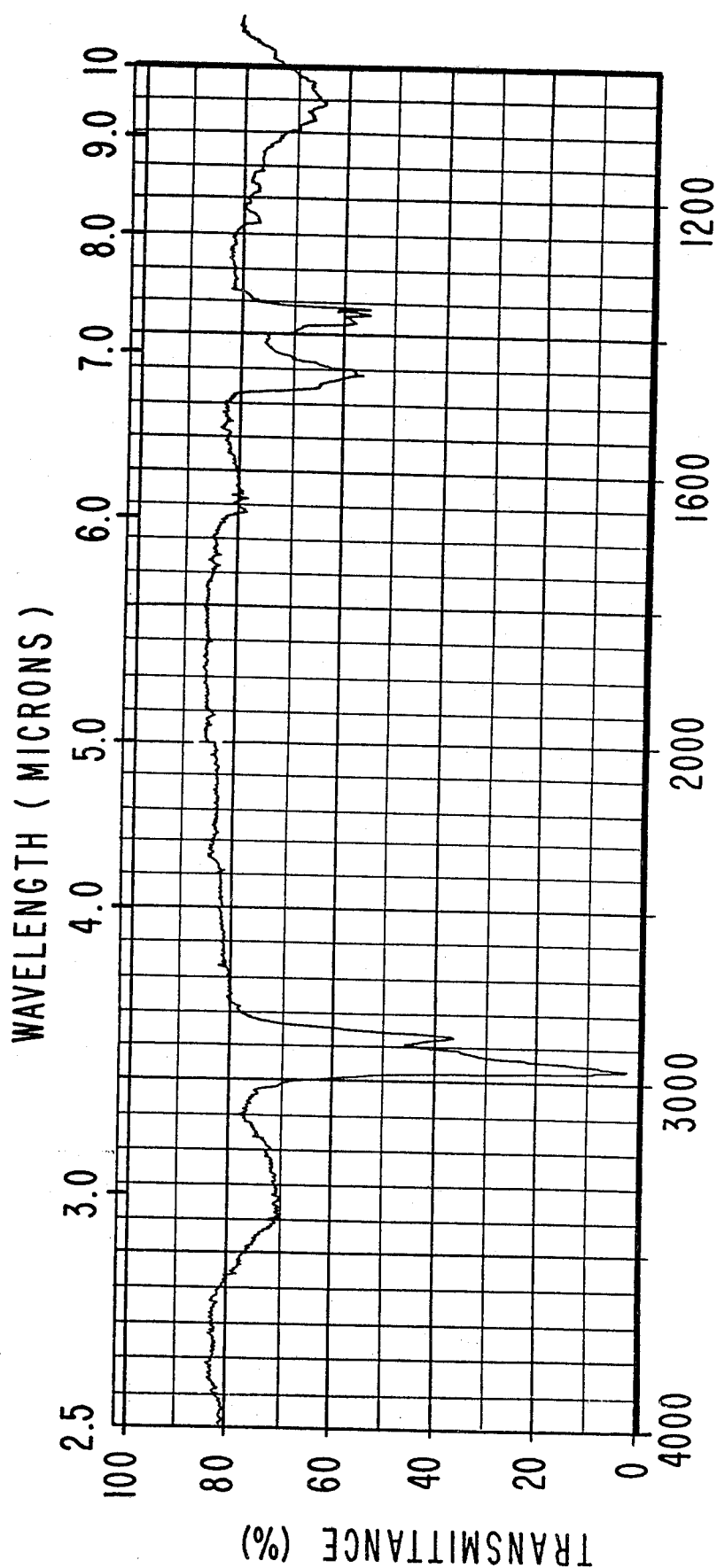
FIG.BB
IR SPECTRUM FOR EXAMPLE A, PEAK 1, OF GLC OF FIG. AE.

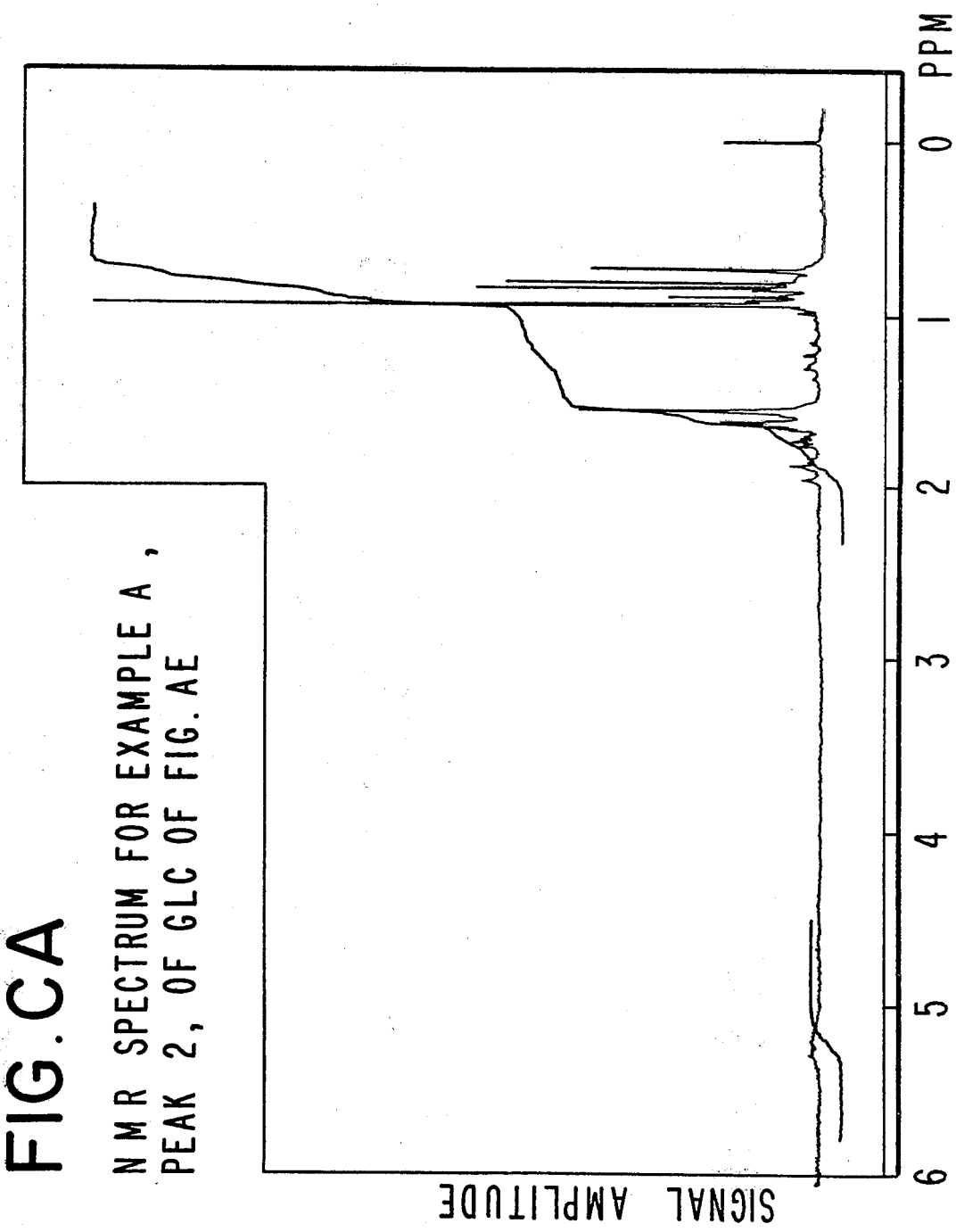
FIG. CA NMR SPECTRUM FOR EXAMPLE A, PEAK 2, OF GLC OF FIG. AE

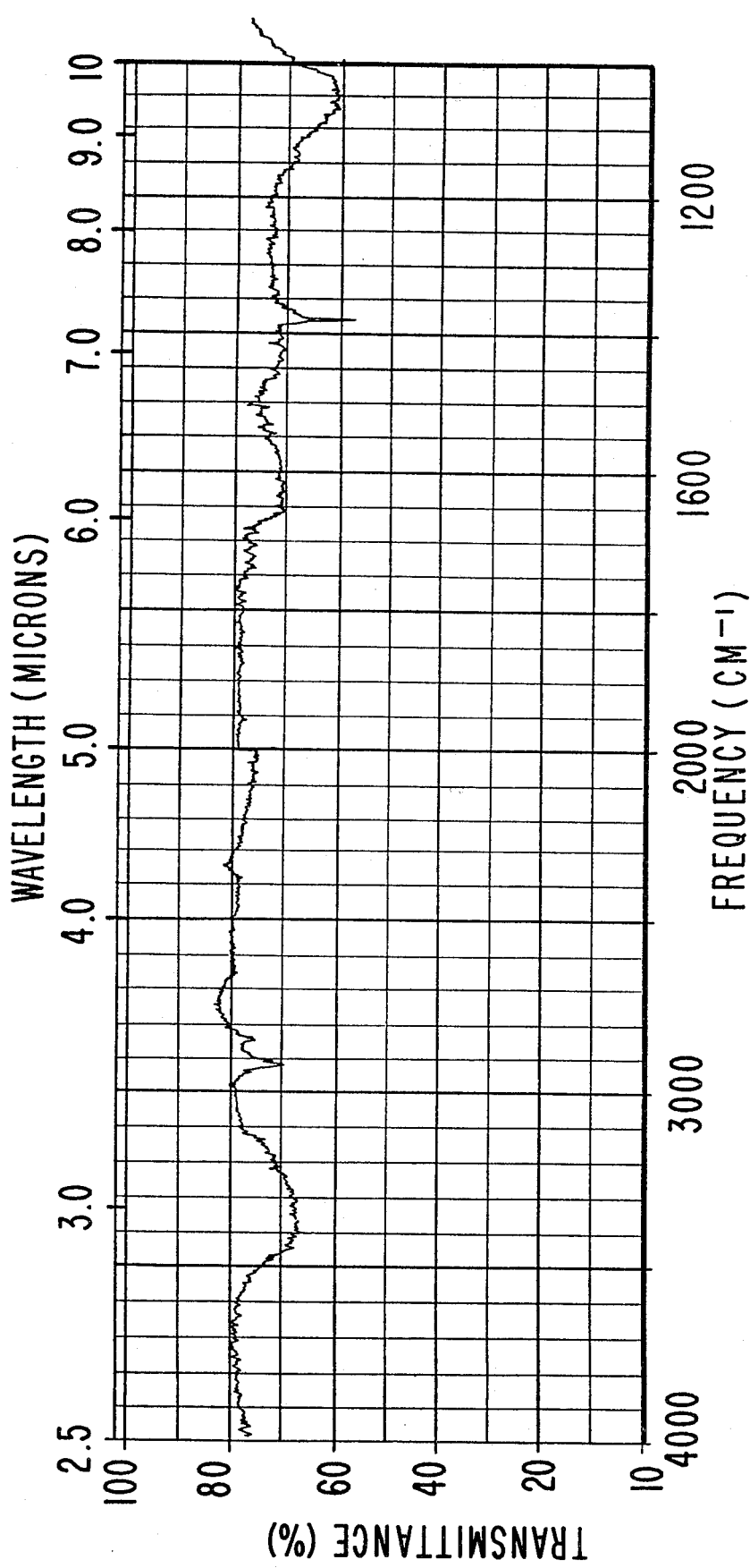
FIG.CB
IR SPECTRUM FOR EXAMPLE I, PEAK 2 OF GLC OF FIG.AE

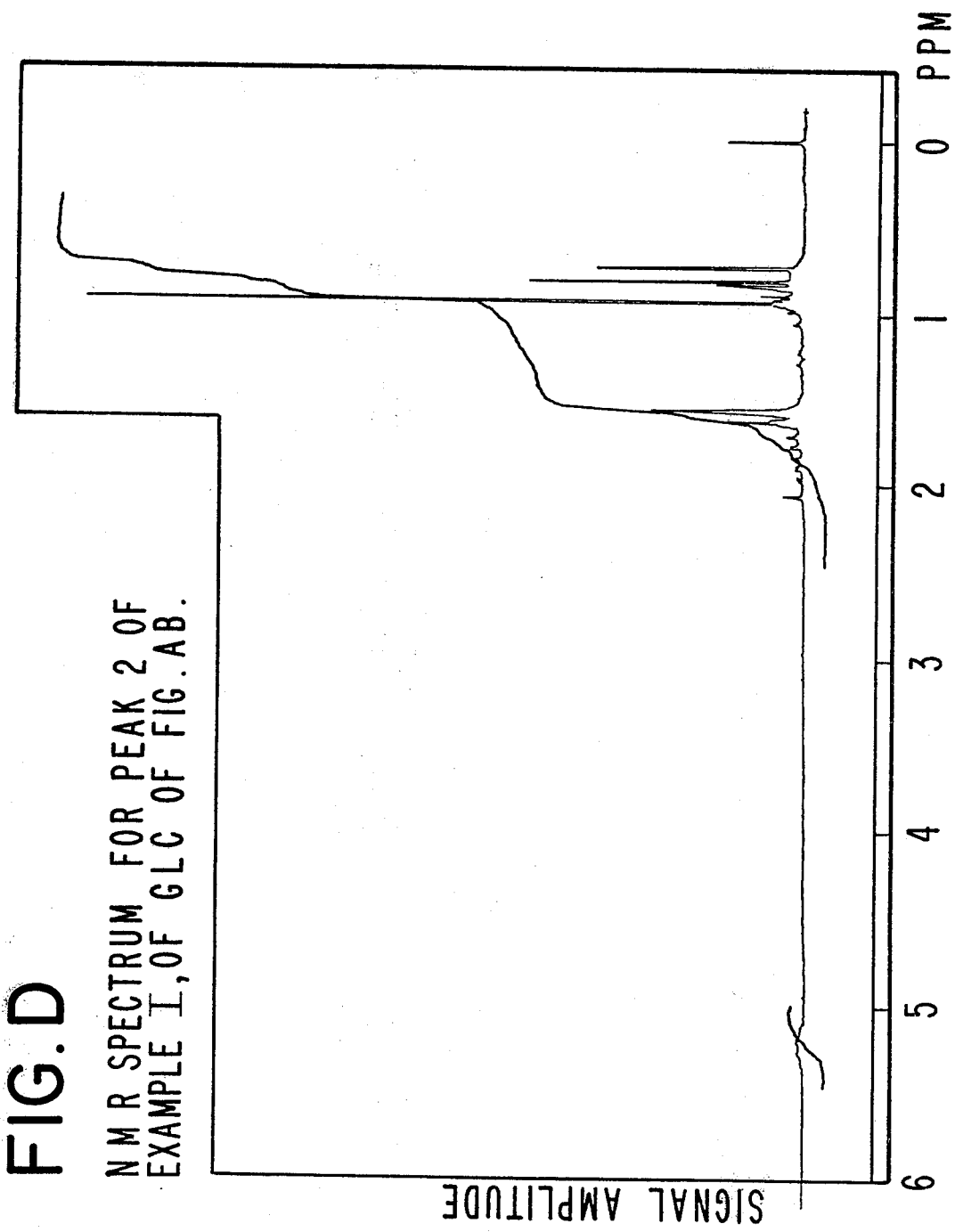
FIG. D
NMR SPECTRUM FOR PEAK 2 OF EXAMPLE I, OF GLC OF FIG. AB.

FIG.I
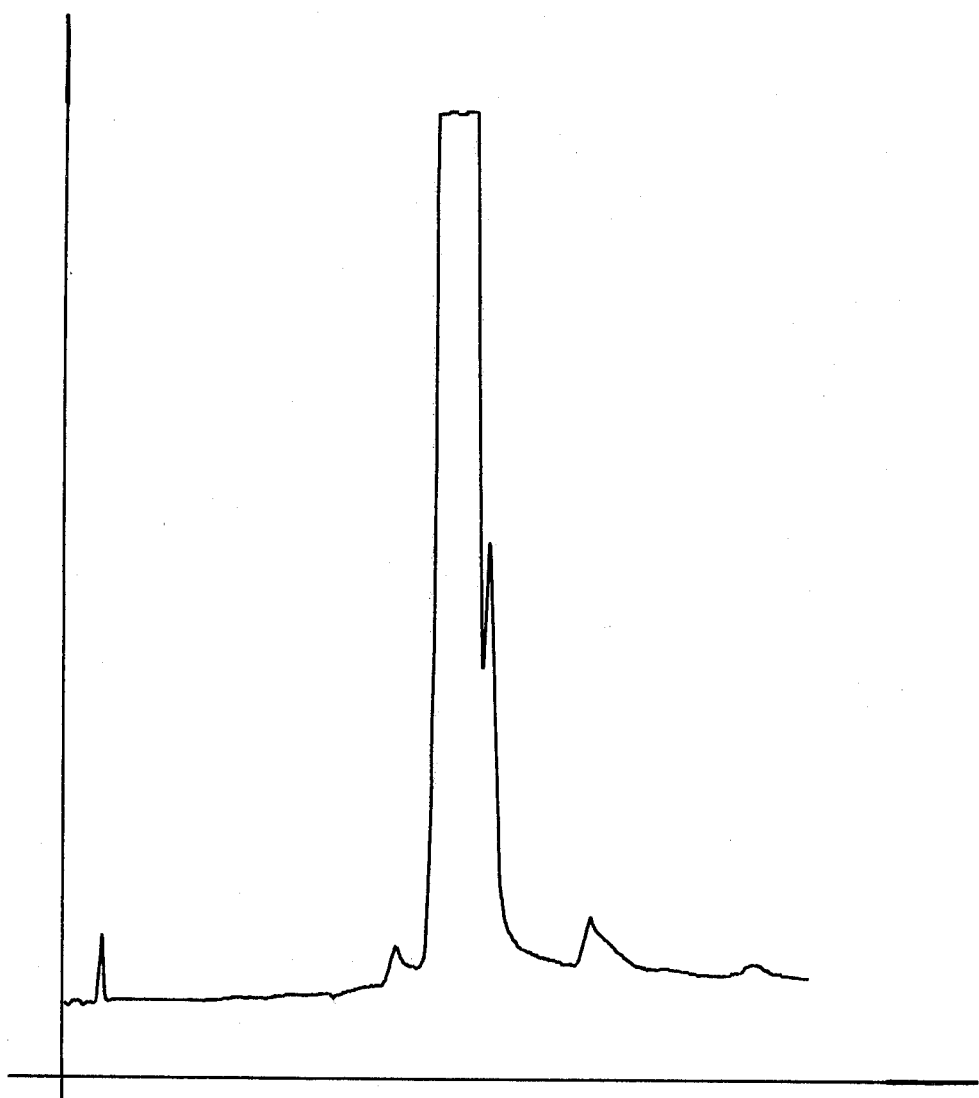
GLC PROFILE FOR EXAMPLE I.

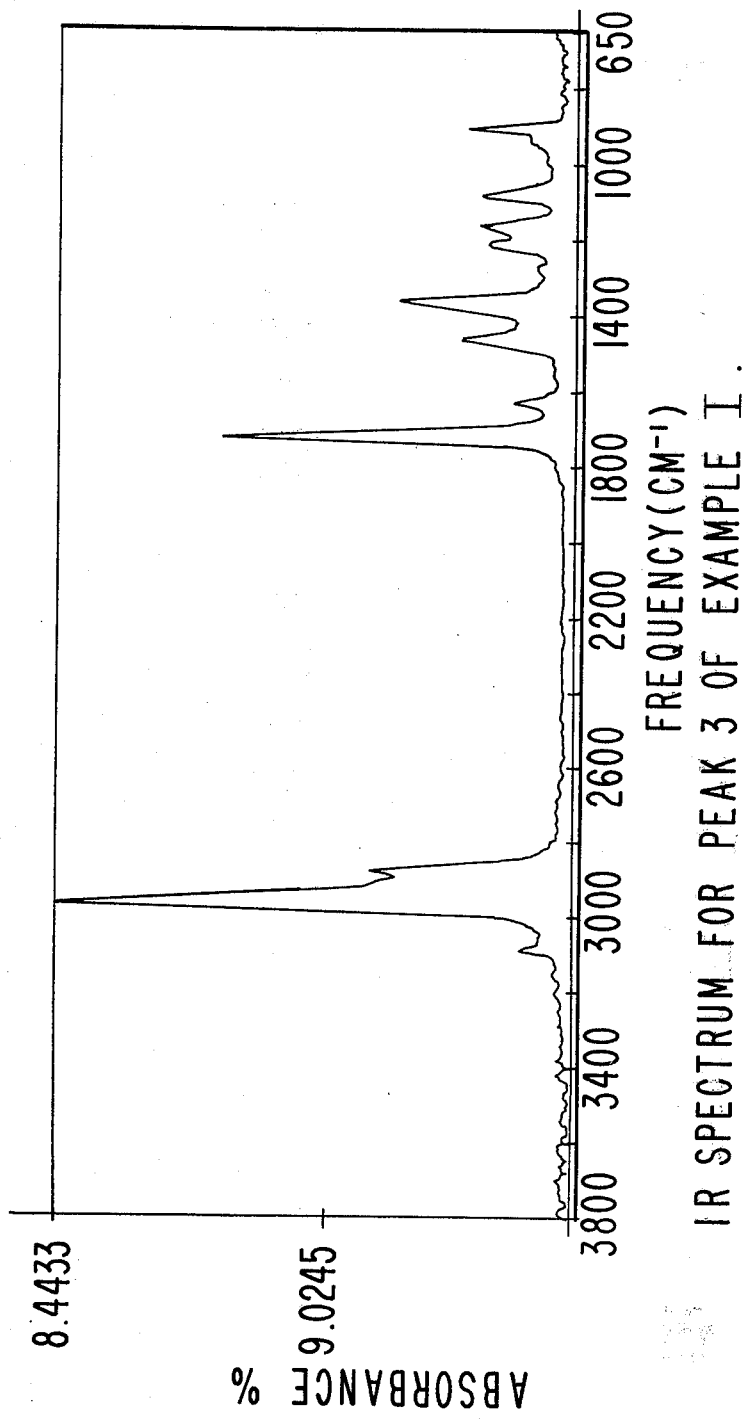

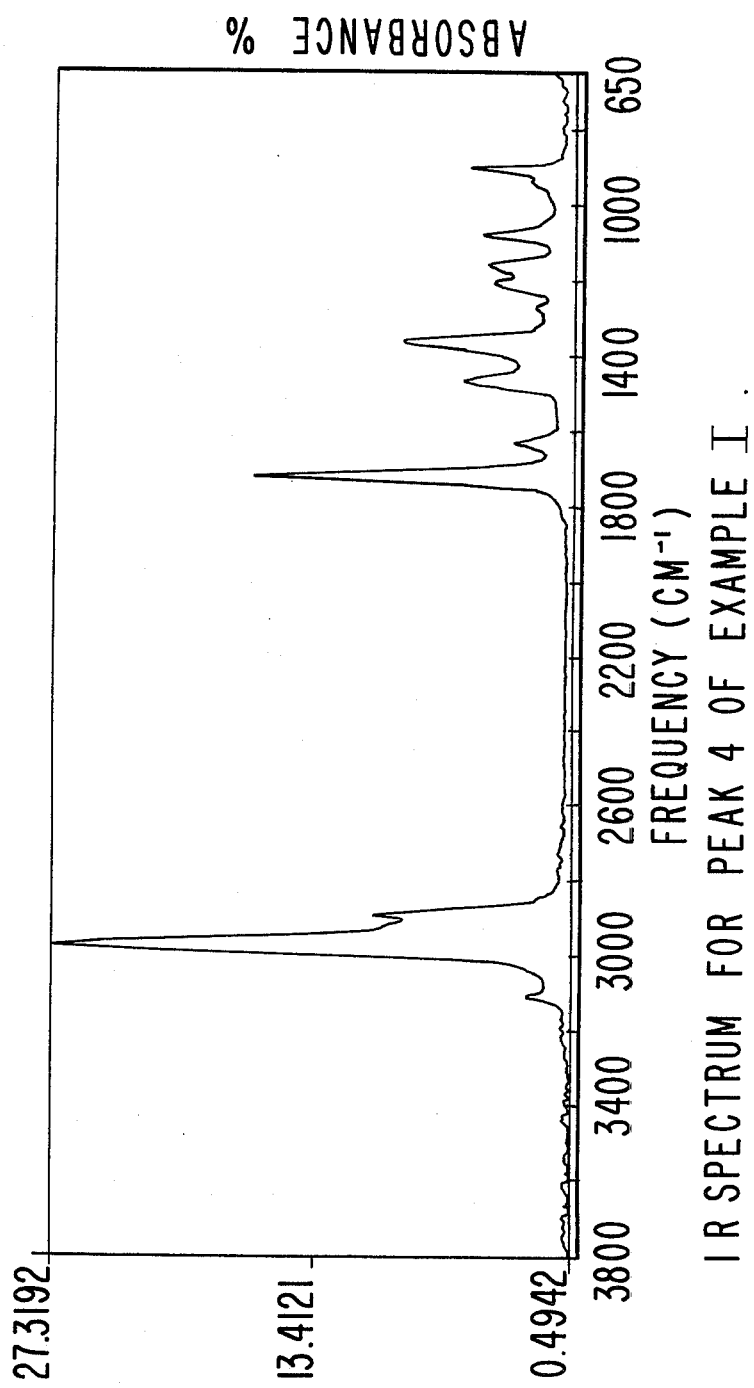

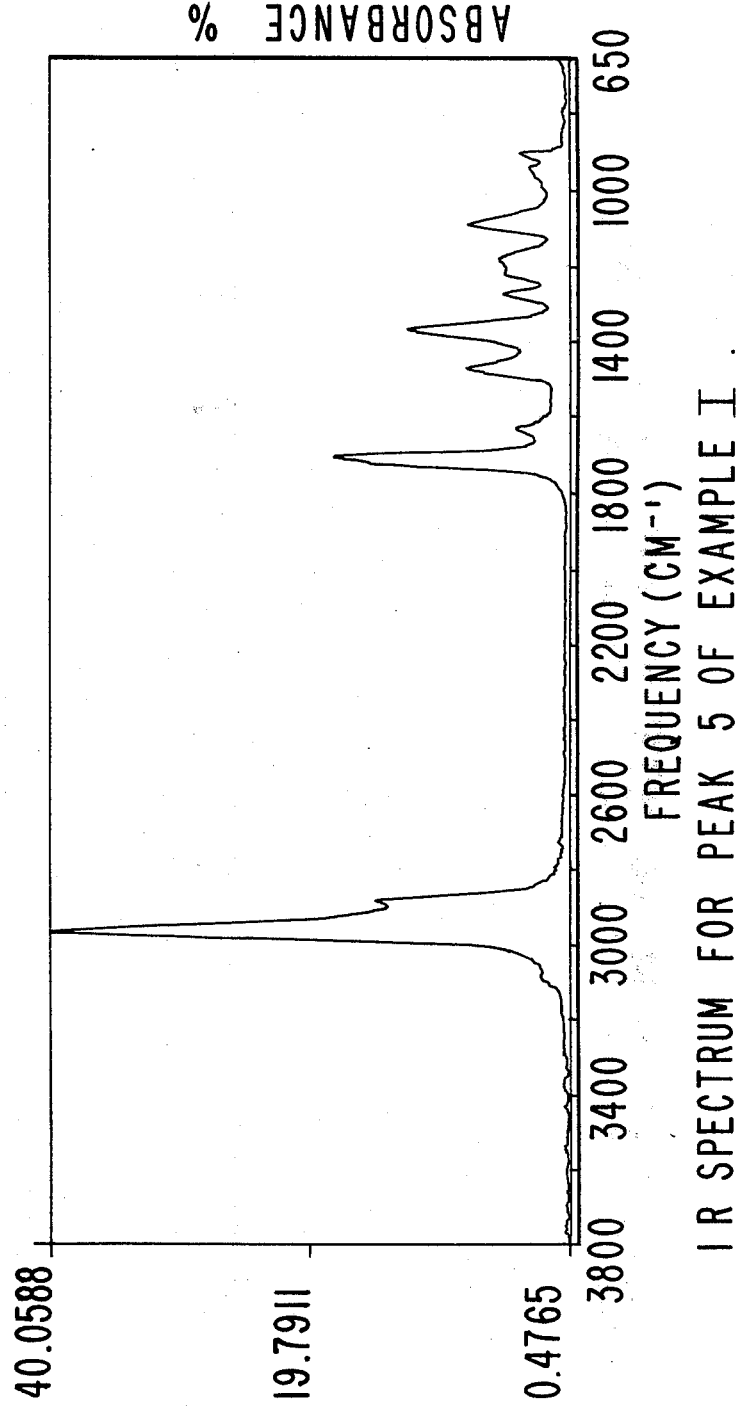
FIG. 2C — IR SPECTRUM FOR PEAK 5 OF EXAMPLE I.

IR SPECTRUM FOR PEAK 6 OF EXAMPLE I.

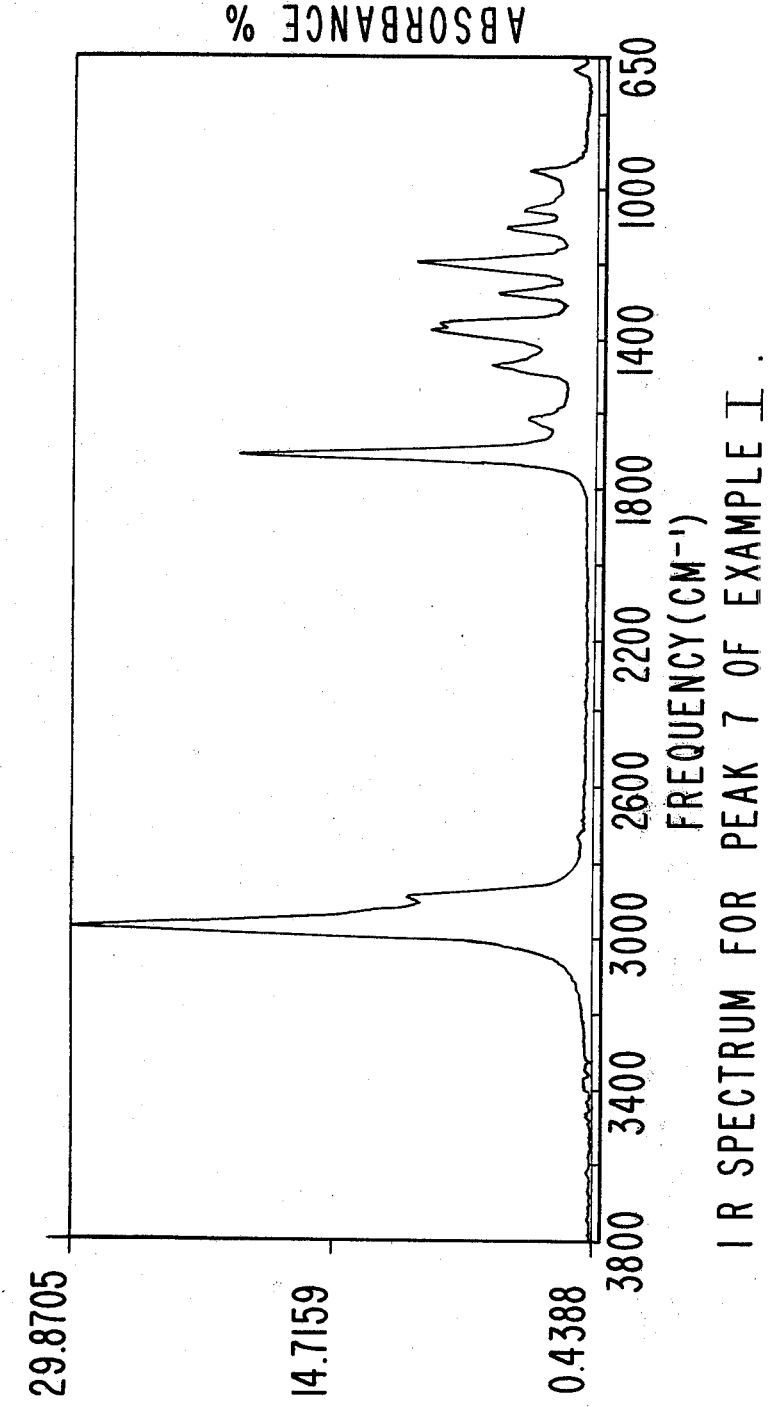

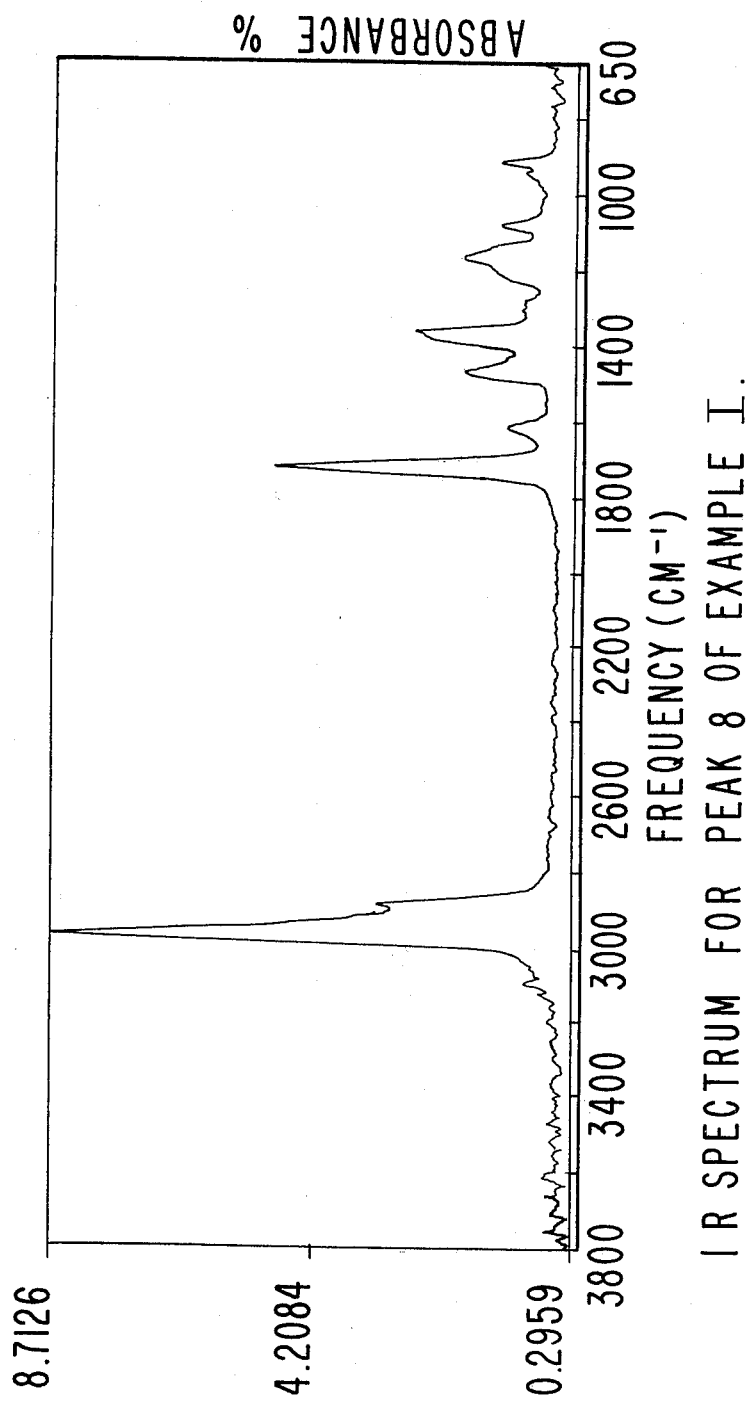

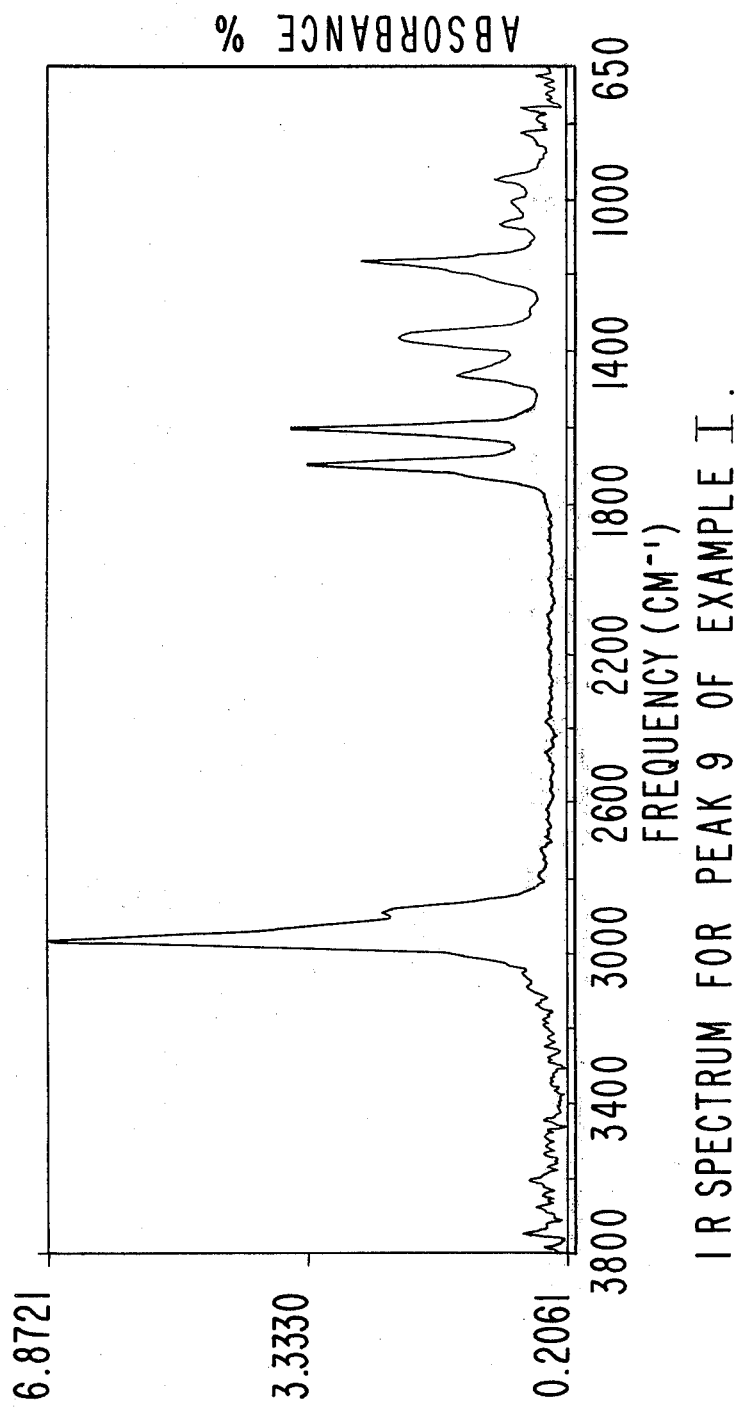
FIG. 2G  IR SPECTRUM FOR PEAK 9 OF EXAMPLE I.

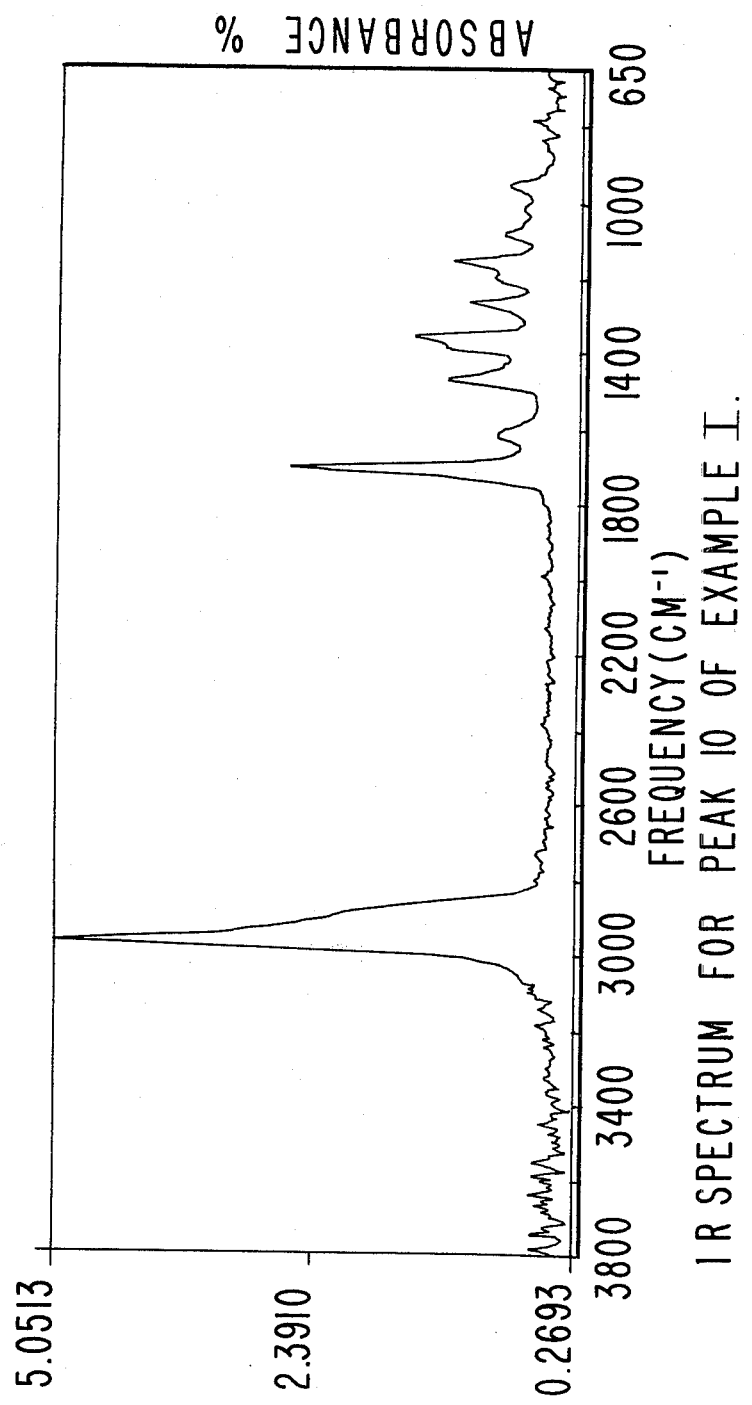
FIG.2H  IR SPECTRUM FOR PEAK 10 OF EXAMPLE I.

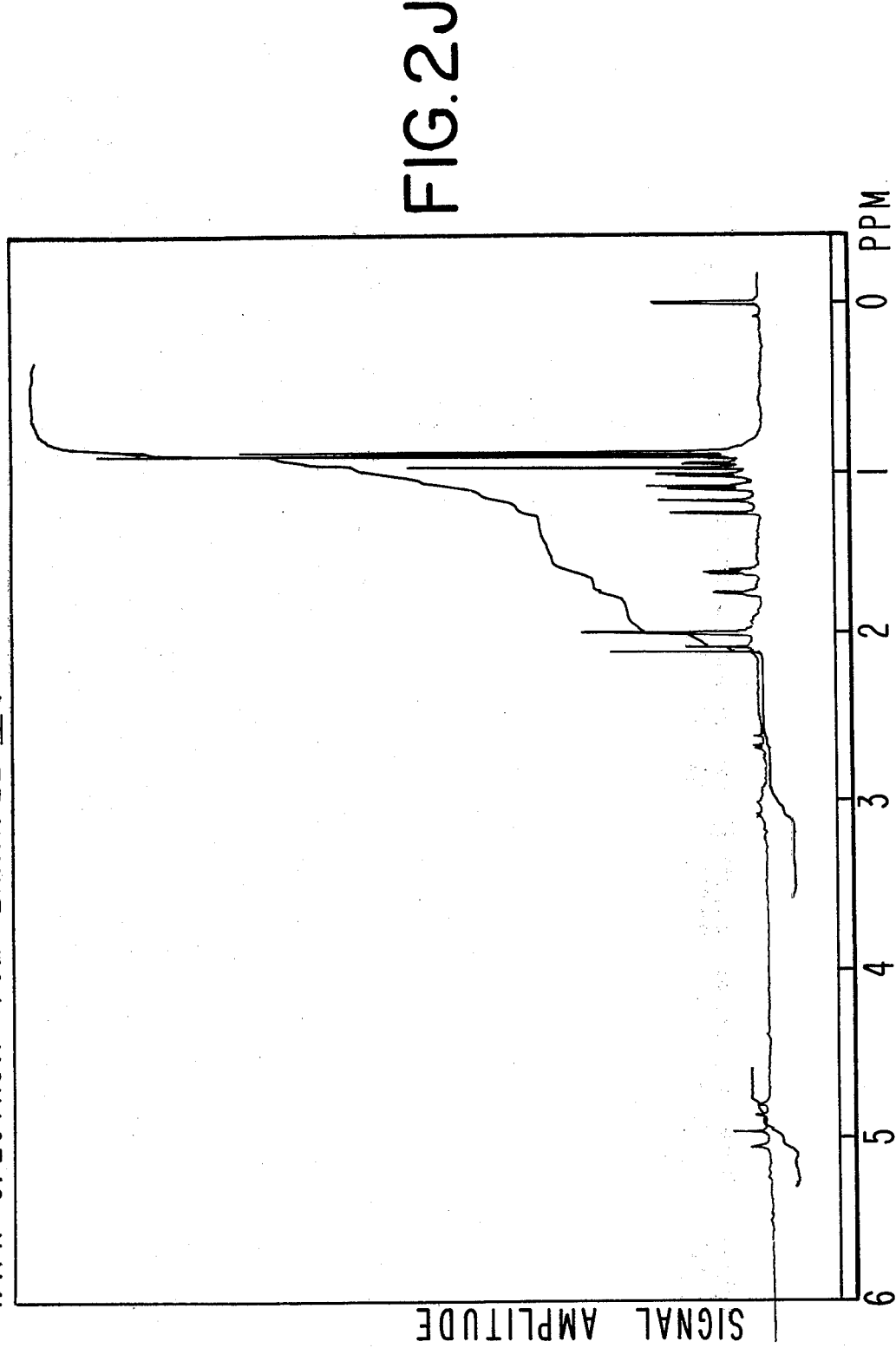

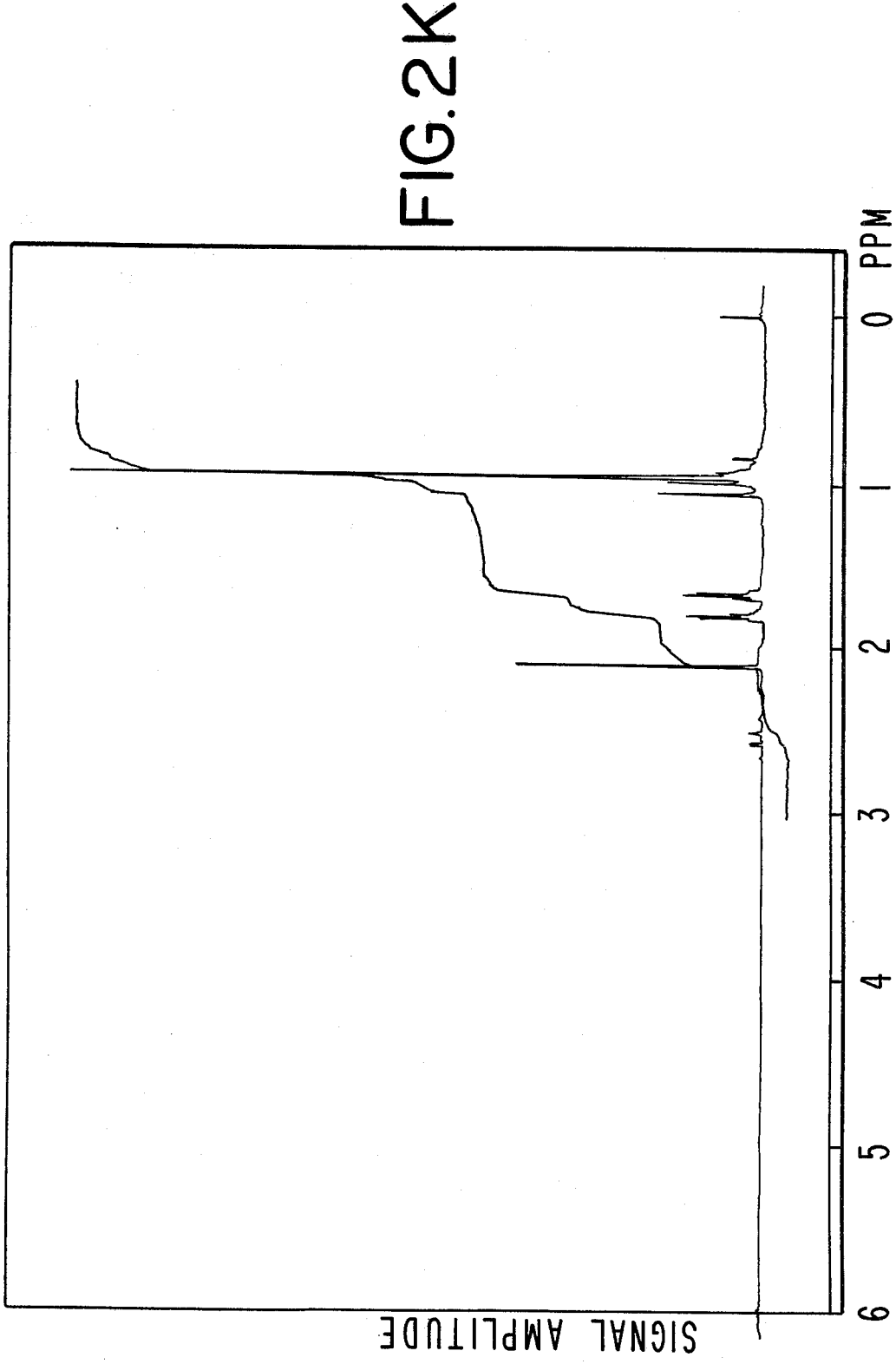

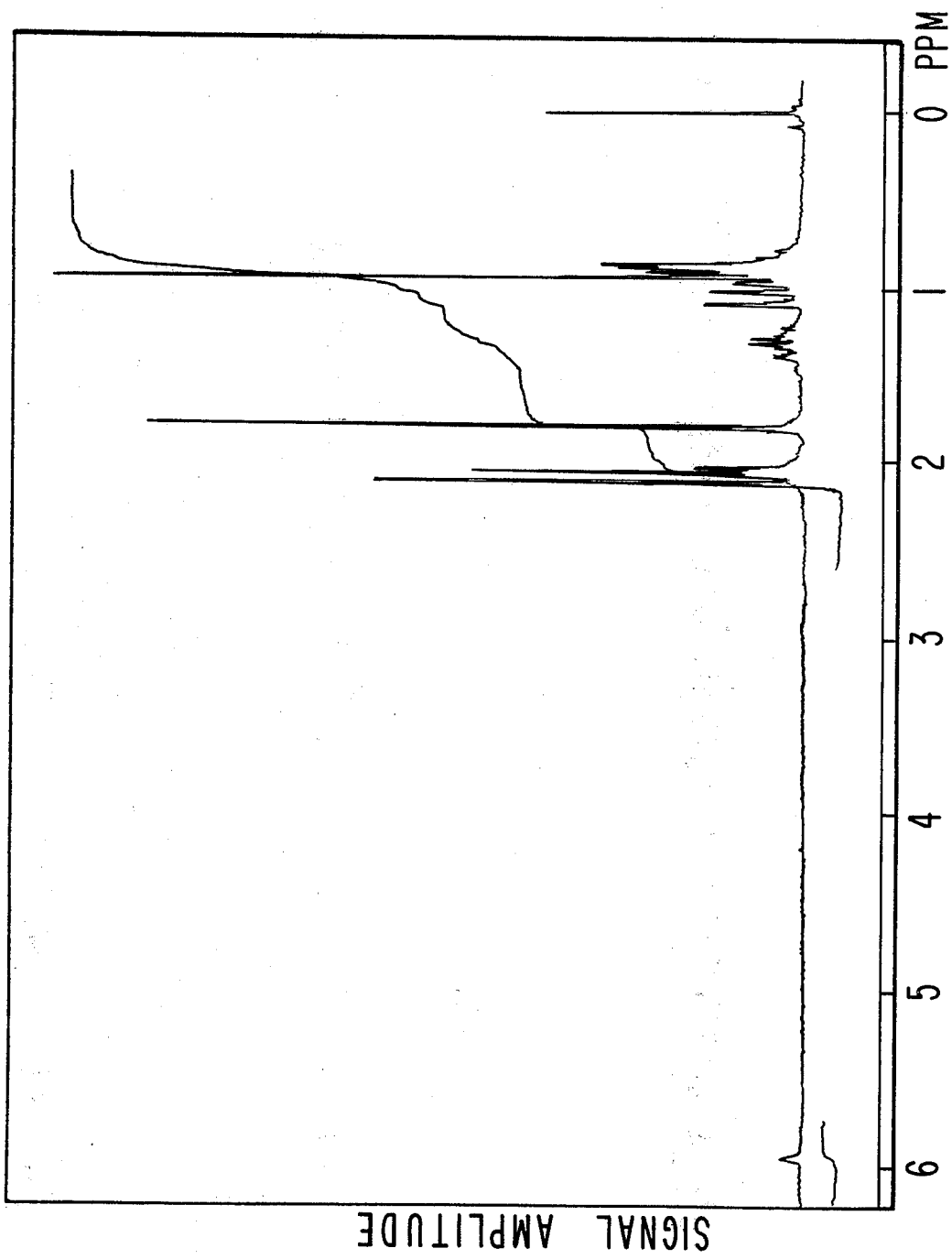
FIG. 2L — NMR SPECTRUM FOR EXAMPLE I.

GLC PROFILE FOR EXAMPLE II.

IR SPECTRUM FOR EXAMPLE II.

MASS SPECTRUM FOR EXAMPLE II.

GLC PROFILE FOR EXAMPLE III.

MASS SPECTRUM FOR EXAMPLE III.

GLC PROFILE FOR EXAMPLE IV.

MASS SPECTRUM FOR EXAMPLE IV.

GLC PROFILE FOR EXAMPLE VA.

GLC PROFILE FOR EXAMPLE VB

GLC PROFILE FOR EXAMPLE VIIA.

USE OF BRANCHED KETONES IN AUGMENTING OR ENHANCING THE AROMA OR TASTE OF FOODSTUFFS, CHEWING GUMS, TOOTHPASTES OR CHEWING TOBACCO

BACKGROUND OF THE INVENTION

The present invention relates to branched ketones of the genus of compounds having the structure:

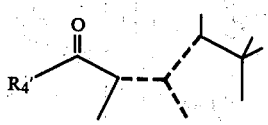

wherein $R_4'$ represents $C_1$–$C_3$ lower alkyl; wherein one of the dashed lines is a carbon-carbon double bond and the other of the dashed lines represents carbon-carbon single bonds, produced by the novel process of our invention, and to novel compositions using one or more of such branched ketones to augment or enhance the flavor and/or aroma of consumable materials, or impart flavor and/or aroma to consumable materials.

There has been considerable work performed relating to substances which can be used to impart (modify, augment or enhance) flavors and fragrances to (or in) various consumable materials. These substances are used to diminish the use of natural materials, some of which may be in short supply, and to provide more uniform properties in the finished product.

Woody, citrus, floral, ionone-like, incense-like, oriental, grapefruit-like, piney, fruity and rosin-like aromas with woody, citrusy, floral, ionone-like, oriental, grapefruit-like, piney, fruity and rosin-like tastes with bitter undertones are particularly desirable for many uses in foodstuff flavors, chewing gum flavors, toothpaste flavors, medicinal products flavors and chewing tobacco flavors.

Sweet, woody, oriental-like, camphoraceous, fruity and spicey aromas prior to smoking and woody, peppery and oriental-like aromas with natural tobacco nuances on smoking in the main-stream and in the side-stream are desirable in smoking tobaccos, smoking tobacco articles and in smoking tobacco flavoring compositions.

Fruity, warm, woody, amber, rum/cognac-like, sandalwood-like, sweet, floral, rich woody, vetiver-like, aromas with patchouli top-notes and minty undertones, are highly desirable in several types of perfume compositions, perfumed articles and colognes.

Unsaturated ketones including unsaturated branched aliphatic, acyclic ketones are well known for use in augmenting or enhancing the aroma and/or taste of consumable materials. Thus, Arctander, "Perfume & Flavor Chemicals (Aroma Chemicals)", published 1969, discloses at monograph No. 472, the use of butylidene acetone having the structure:

Arctander states that butylidene acetone has a powerful, grassy, green, pungent odor and a rather poor tenacity. At monograph 2427, Vol. 2, Arctander states that Octylidene acetone having the structure:

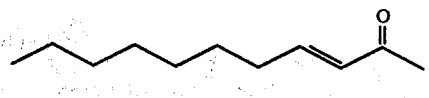

is useful in Jasmin compositions as a modifier for Amylcinnamic aldehyde, or in Gardenia and other heavy floral perfumes, where herbaceous-fruity notes are desirable and compatible with the fragrance picture.

U.S. Pat. No. 2,315,046 discloses the use as ingredients in perfumery of certain acylated olefins, which olefins have structures such as:

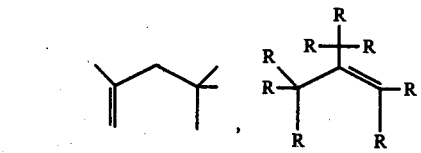

These materials are prepared interalia from commercial diisobutylene according to the reaction:

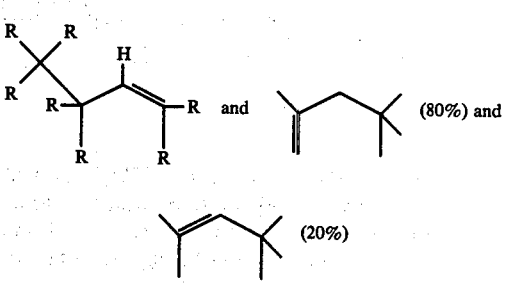

wherein n is 3 or more, and R represents a hydrocarbon radical. Branched unsaturated alpha-beta ketones were known prior to that, for example, in U.S. Pat. No. 2,246,032, issued on June 17, 1941, disclosing compounds having the generic structure:

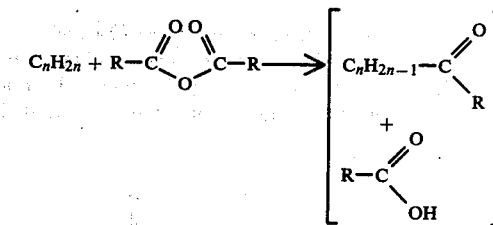

wherein $R_1$–$R_7$ may be any member of the group consisting of hydrogen, aliphatic and cyclo paraffinic.

Also, claimed in U.S. Pat. No. 2,315,046 are compounds having the structures:

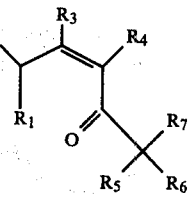

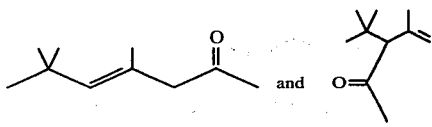

In addition, U.S. Pat. No. 2,463,742 discloses the reaction:

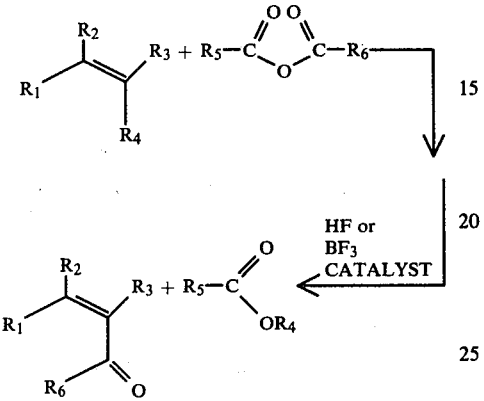

U.S. Pat. No. 3,453,317, issued on July 1, 1969, discloses certain gamma, delta unsaturated ketones as odorants for perfumery purposes at Column 4, line 33 including the group of ketones having the structure:

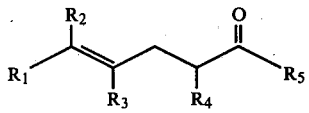

wherein $R_1$–$R_5$ are various hydrocarbon radicals.

U.S. Pat. No. 2,870,210, discloses as having aromas such as fruity, "reminiscent of apple juice" the compound 6,8-dimethyl-5-nonene-2-one having the structure:

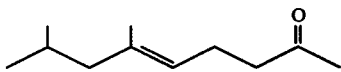

as well as 6,10-dimethyl-5-undecane-2-one having the structure:

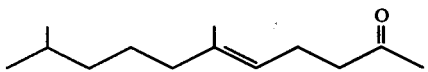

Nothing in the prior art specifically discloses the genus of compounds having the structure:

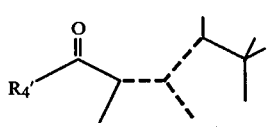

wherein $R_4'$ represents $C_1$–$C_3$ lower alkyl; wherein one of the dashed lines represents a carbon-carbon double bond and the other of the dashed lines represents a carbon-carbon single bond. And nothing in the prior art discloses the generic process:

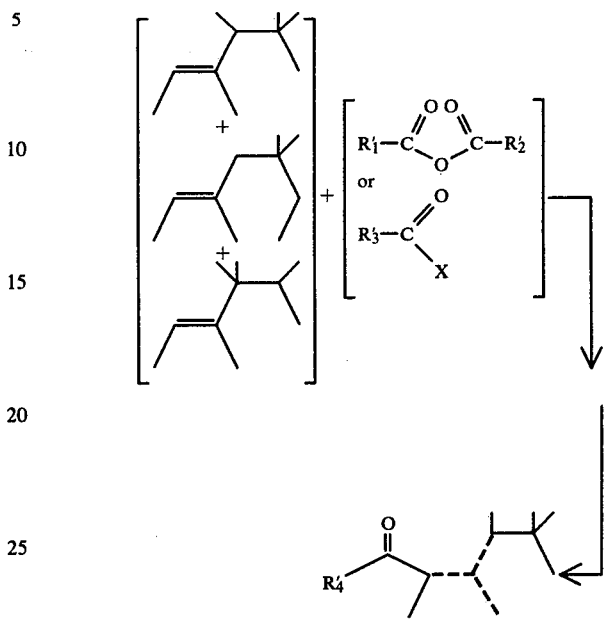

wherein $R_1'$, $R_2'$ and $R_3'$ are the same or different and each represents $C_1$–$C_3$ lower alkyl; wherein $R_4'$ is as defined above and wherein X is chloro or bromo. Indeed, the compounds and processes of our invention give rise to unexpected, unobvious and advantageous utilities insofar as organoleptic uses are concerned.

BRIEF DESCRIPTION OF THE DRAWINGS

FIG. AA represents the GLC profile for the reaction product of Example A using a 70% sulfuric acid catalyst at 35%C.

FIG. AB represents the GLC profile for the reaction product of Example A using an Amberlyst ® 15 acidic ion exchange resin catalyst at a temperature of 150° C.

FIG. AC represents the GLC profile for the reaction product of Example A, using an Amberlyst ® 15 catalyst at 100° C.

FIG. AD represents the GLC profile for the reaction product of Example A, using a sulfuric acid catalyst and an alpha-methylstyrene diluent at 35° C. according to the conditions of United Kingdom Pat. No. 796,130 (crude reaction product).

FIG. AE represents the GLC profile for the reaction product of Example I, using a sulfuric acid catalyst, at 35° C. and an alpha-methyl styrene diluent according to the conditions of United Kingdom Pat. No. 796,130 (distilled reaction product).

FIG. BA represents the NMR spectrum for Peak 1 of the GLC profile of FIG. AE.

FIG. BB represents the infra-red spectrum for Peak 1 of the GLC profile of FIG. AE.

FIG. CA represents the NMR spectrum fir Peak 2 of the GLC profile of FIG. AE.

FIG. CB represents the infra-red spectrum for Peak 2 of the GLC profile of FIG. AE.

FIG. D represents the NMR spectrum for Peak 2 of the GLC profile of FIG. AB.

FIG. 1 sets forth the GLC profile for the reaction product of Example I, containing compounds defined according to the structure:

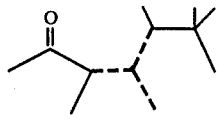

wherein in each molecule of the mixture, one of the dashed lines is a carbon-carbon double bond and the other of the dashed lines are carbon-carbon single bonds.

FIG. 2A represents the infra-red spectrum of Peak 3 of the GLC profile of FIG. 1.

FIG. 2B represents the infra-red spectrum of Peak 4 of the GLC profile of FIG. 1.

FIG. 2C represents the infra-red spectrum for Peak 5 of the GLC profile of FIG. 1.

Figure 2D:
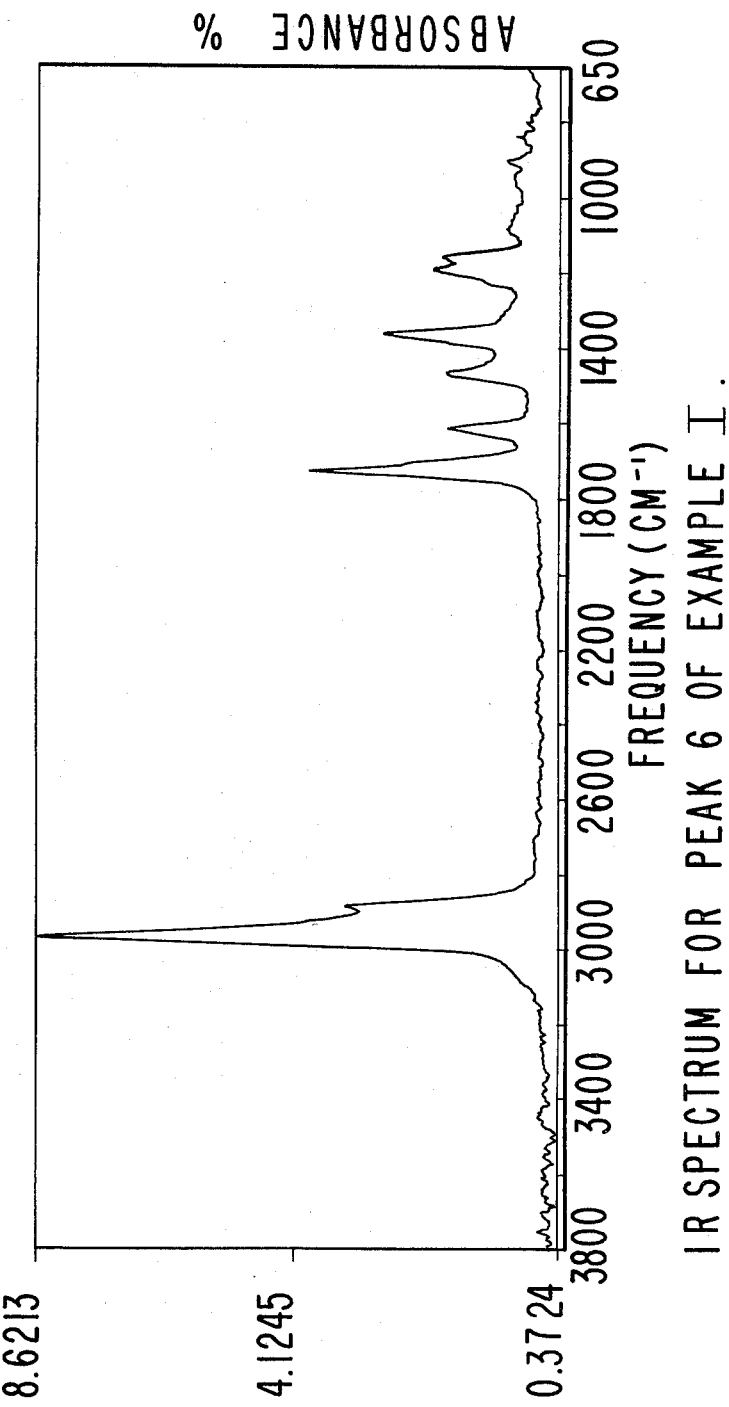

FIG. 2D represents the infra-red spectrum for Peak 6 of the GLC profile of FIG. 1.

FIG. 2E represents the infra-red spectrum for Peak 7 of the GLC profile of FIG. 1.

FIG. 2F represents the infra-red spectrum for Peak 8 of the GLC profile of FIG. 1.

FIG. 2G represents the infra-red spectrum for Peak 9 of the GLC profile of FIG. 1.

FIG. 2H represents the infra-red spectrum for Peak 10 of the GLC profile of FIG. 1.

FIG. 2J represents the NMR spectrum for a mixture of compounds having the structures:

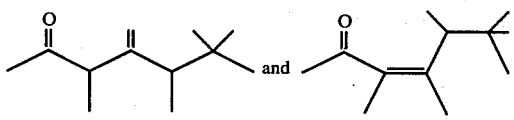

produced according to Example I.

FIG. 2K represents the NMR spectrum for the compound having the structure:

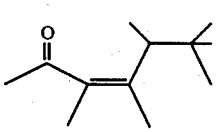

produced according to Example I.

FIG. 2L represents the NMR spectrum for the compound containing the structure:

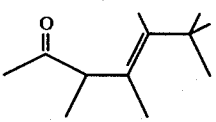

produced according to Example 1.

Figure 3:
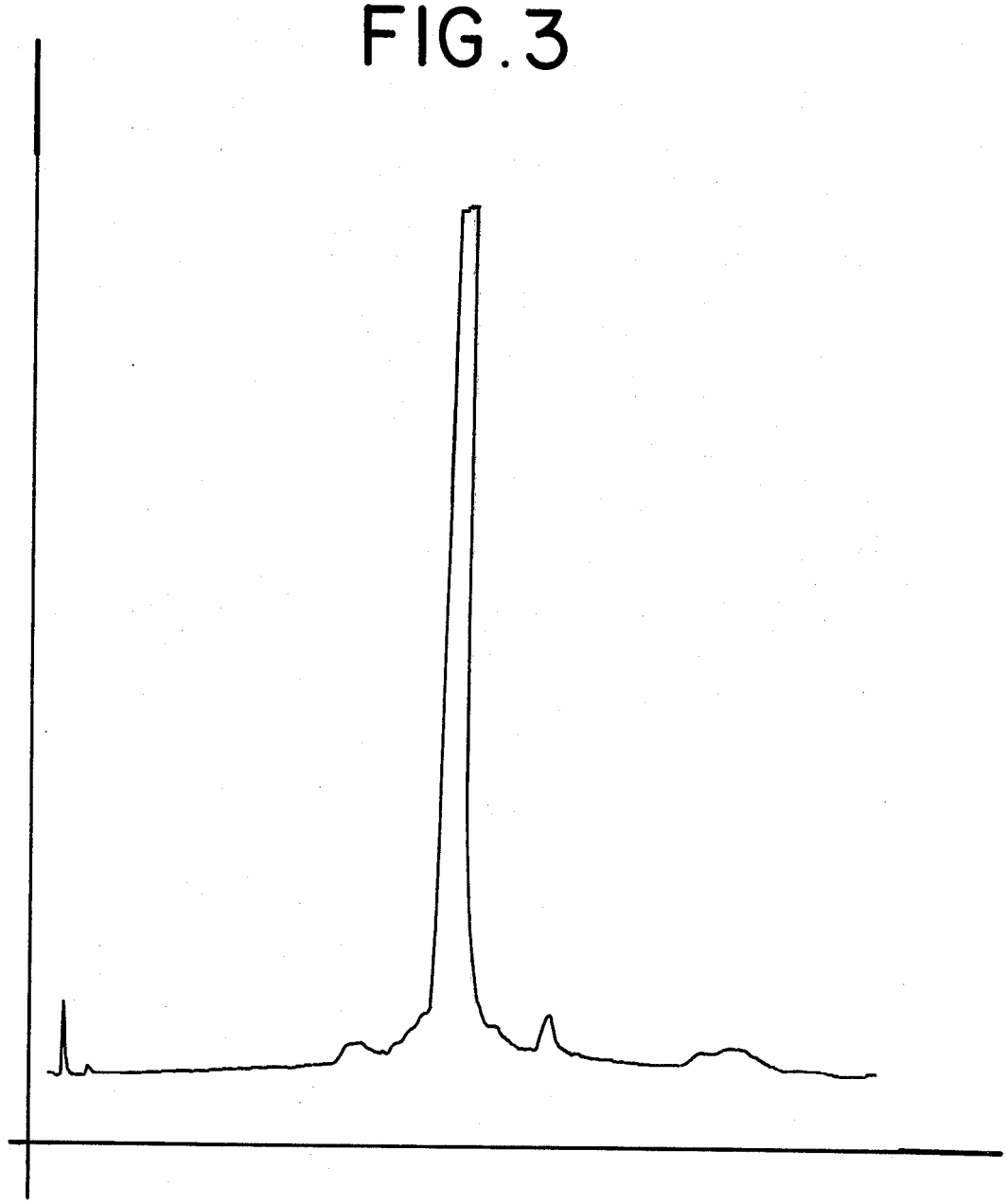

FIG. 3 represents the GLC profile for the reaction product of Example II containing a mixture of compounds, each of which is defined according to the generic structure:

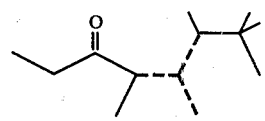

wherein in each molecule one of the dashed lines is a carbon-carbon double bond and each of the other of the dashed lines are carbon-carbon single bonds.

Figure 4:
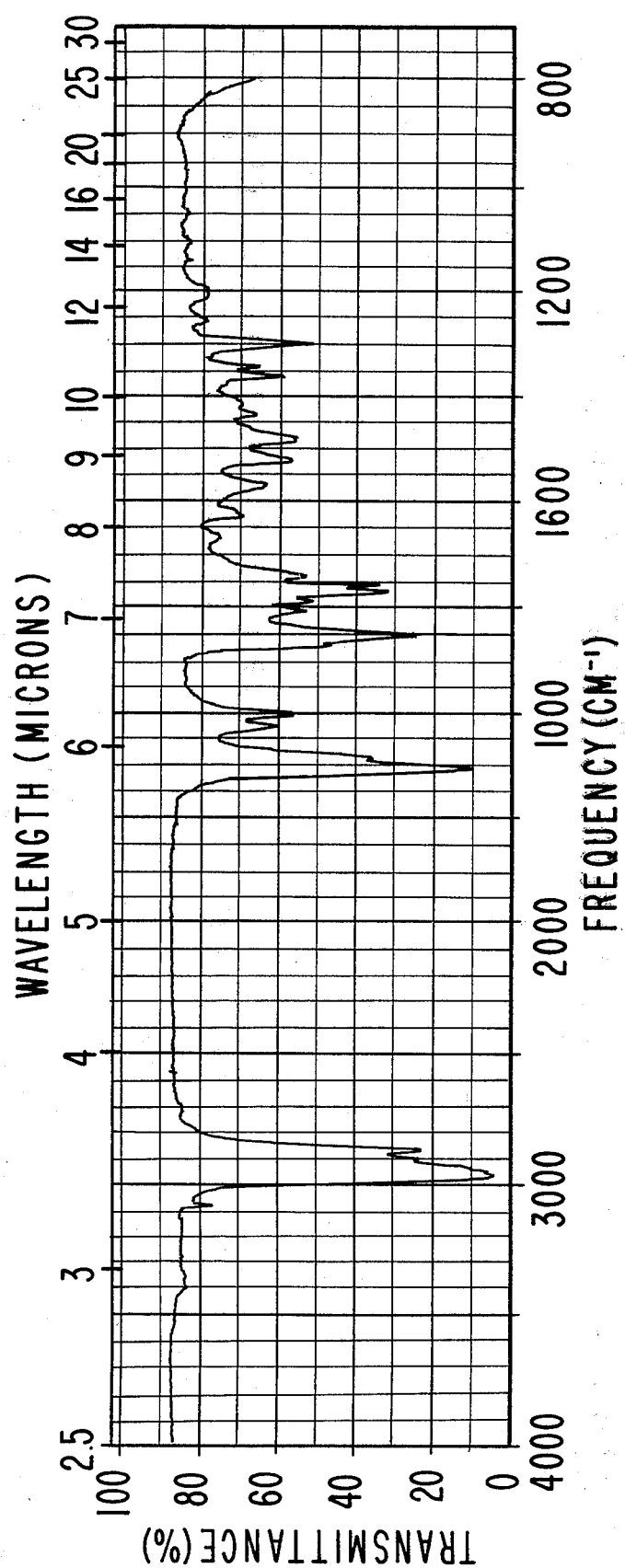

FIG. 4 represents the infra-red spectrum for the product produced according to Example II containing the compounds having the structures:

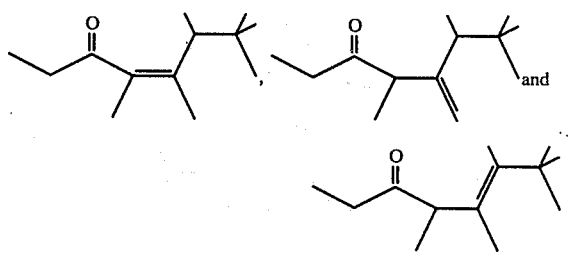

Figure 5:
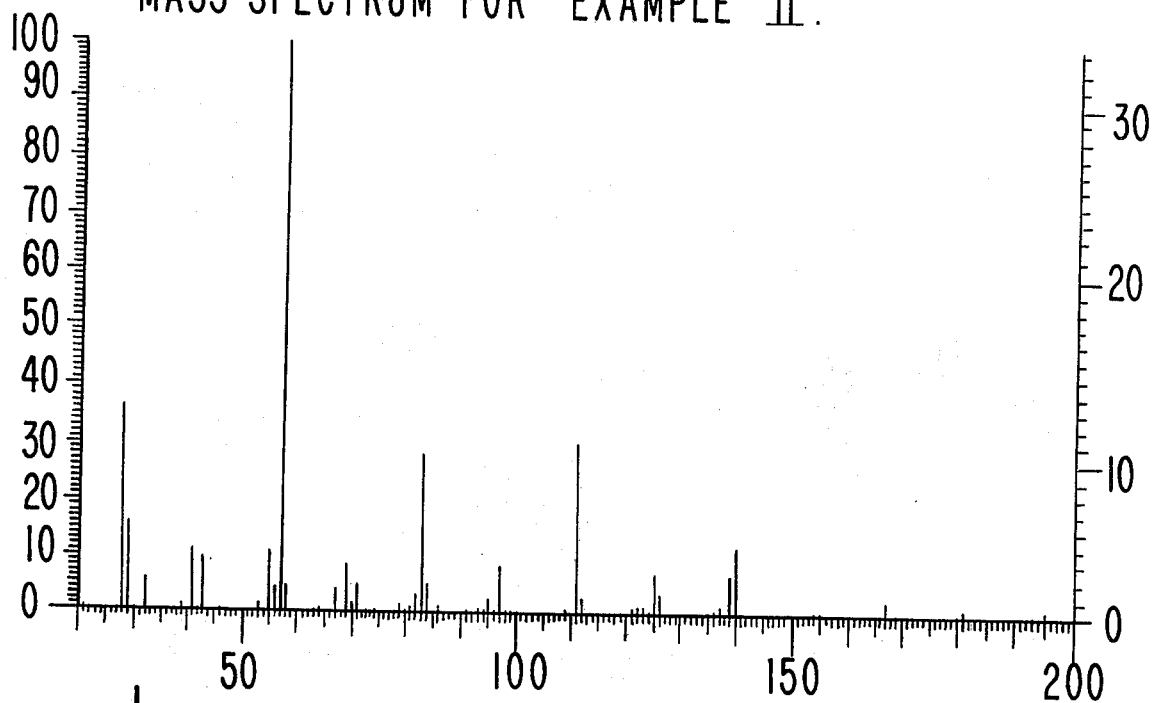

FIG. 5 represents the mass spectrum for the reaction product of Example II, containing the compounds having the structures:

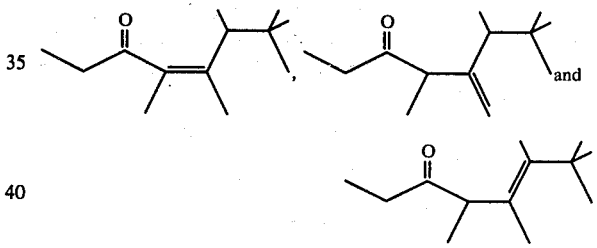

Figure 6:
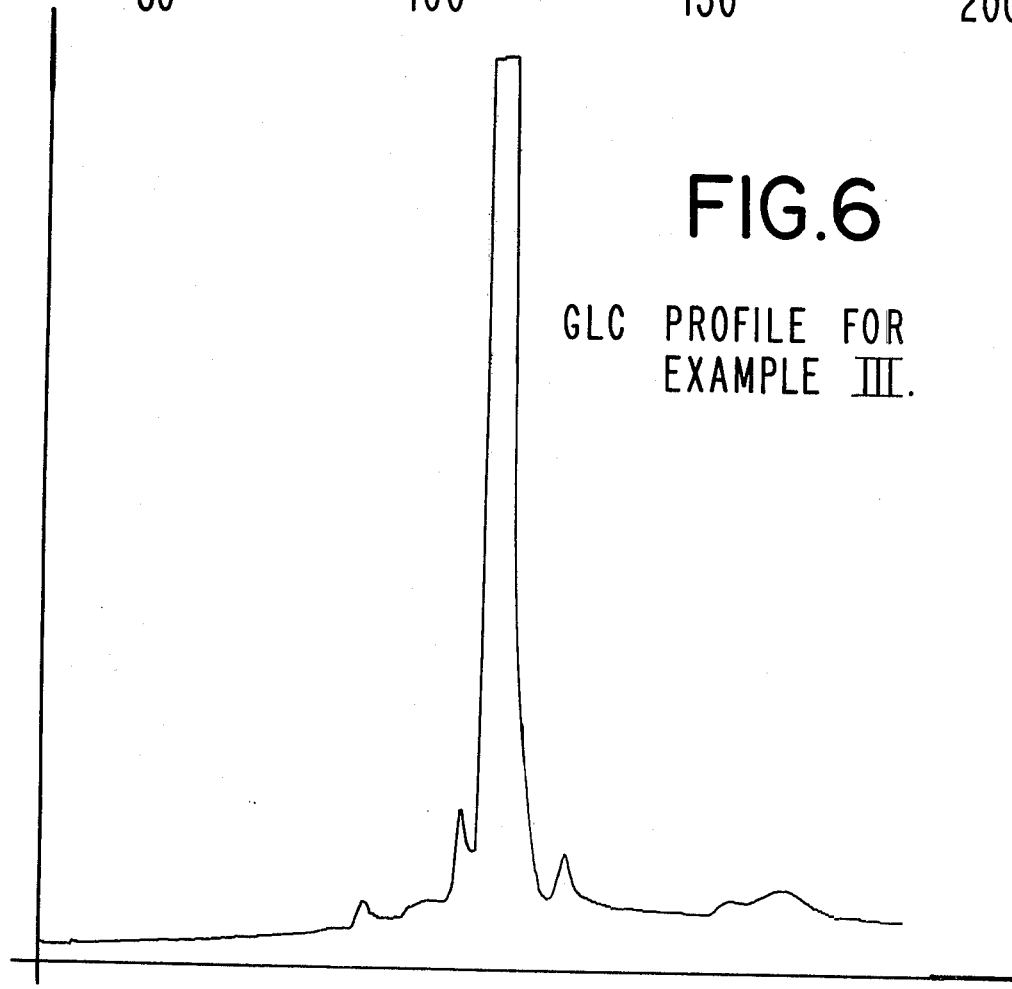

FIG. 6 represents the GLC profile for the reaction product of Example III containing compounds defined according to the generic structure:

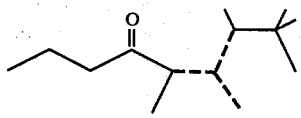

wherein in each of the molecules of the mixture, one of the dashed lines represents a carbon-carbon double bond and the other of the dashed lines represent carbon-carbon single bonds.

Figure 7:
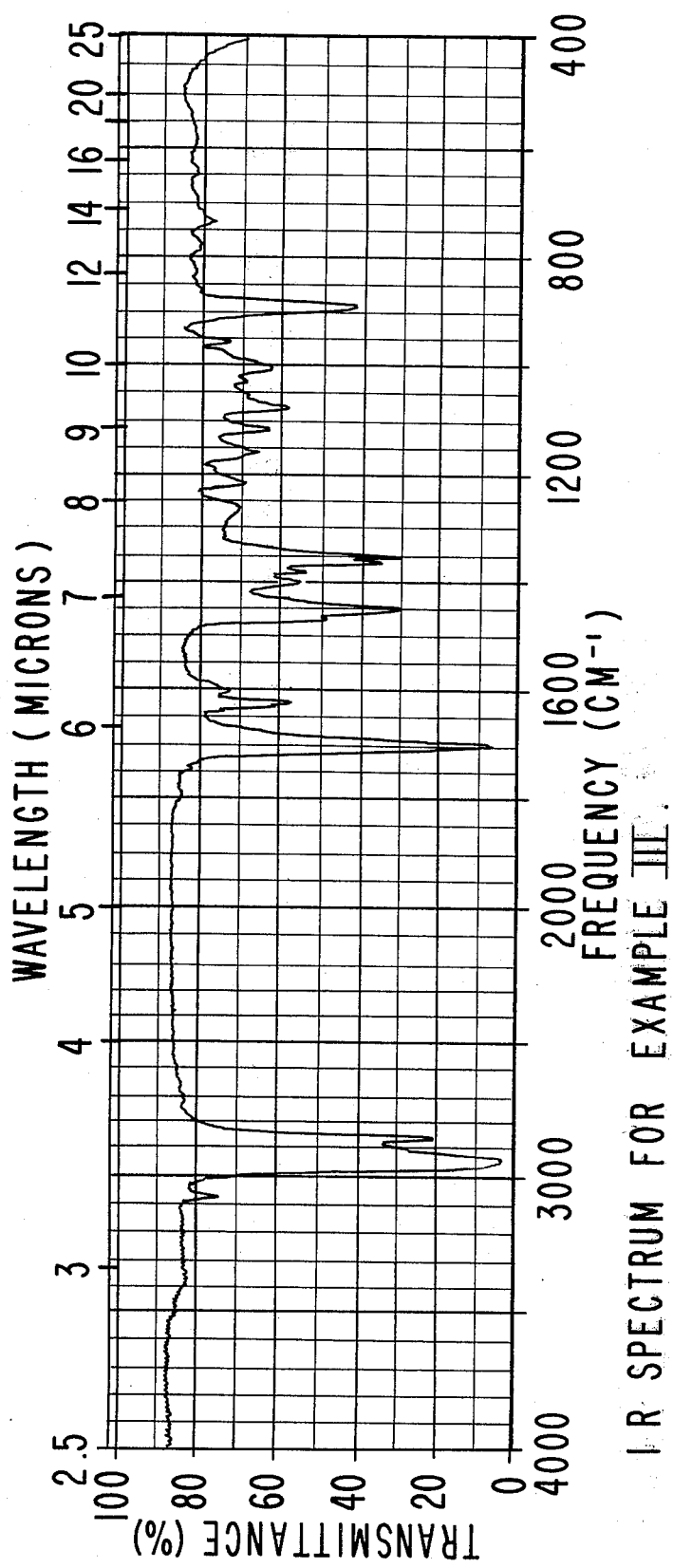

FIG. 7 represents the infra-red spectrum for the reaction product of Example III containing the compounds having the structures:

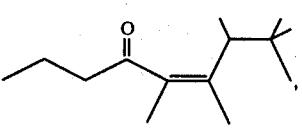

-continued

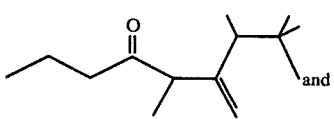

5

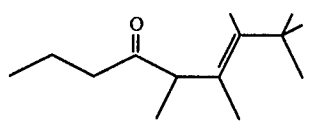

10

Figure 8:
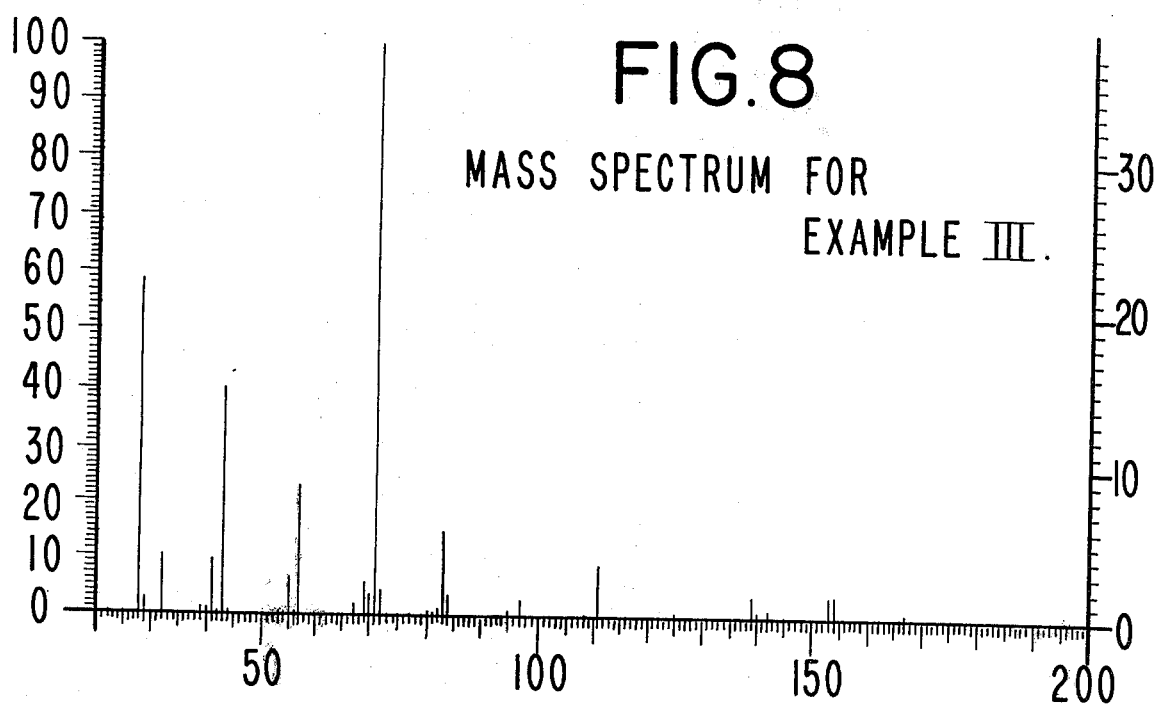

FIG. 8 represents the mass spectrum for the reaction product of Example III containing the compounds having the structures:

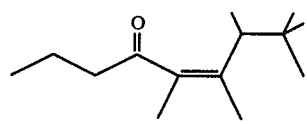

20

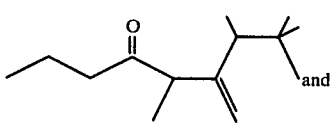

25

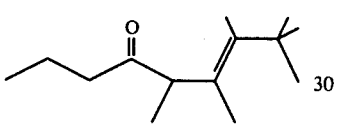

30

Figure 9:
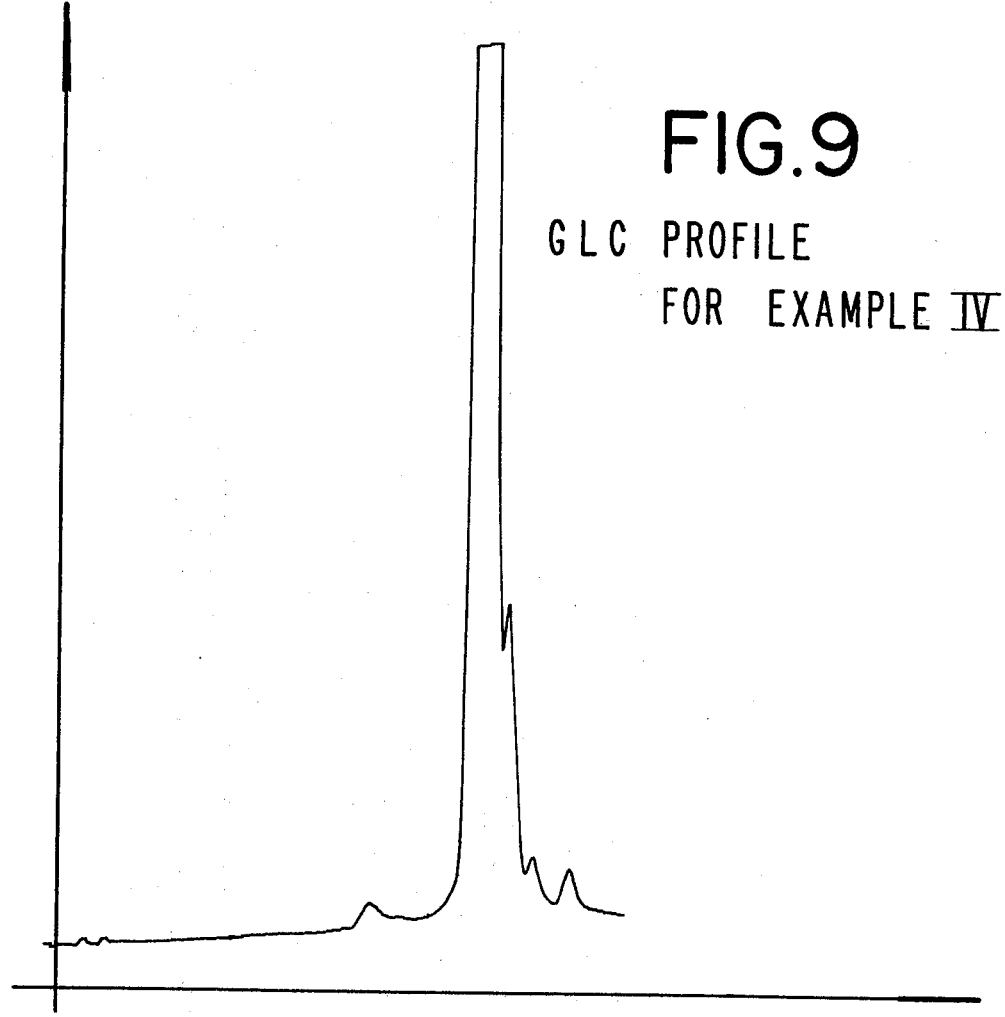

FIG. 9 represents the GLC profile for the reaction product of Example IV, containing a mixture of compounds, each of which is defined according to the generic structure:

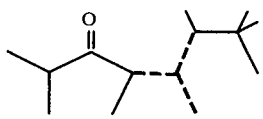

40 wherein in each of the molecules, one of the dashed lines represents a carbon-carbon double bond and each of the other of the dashed lines represent carbon-carbon single bonds.

Figure 10:
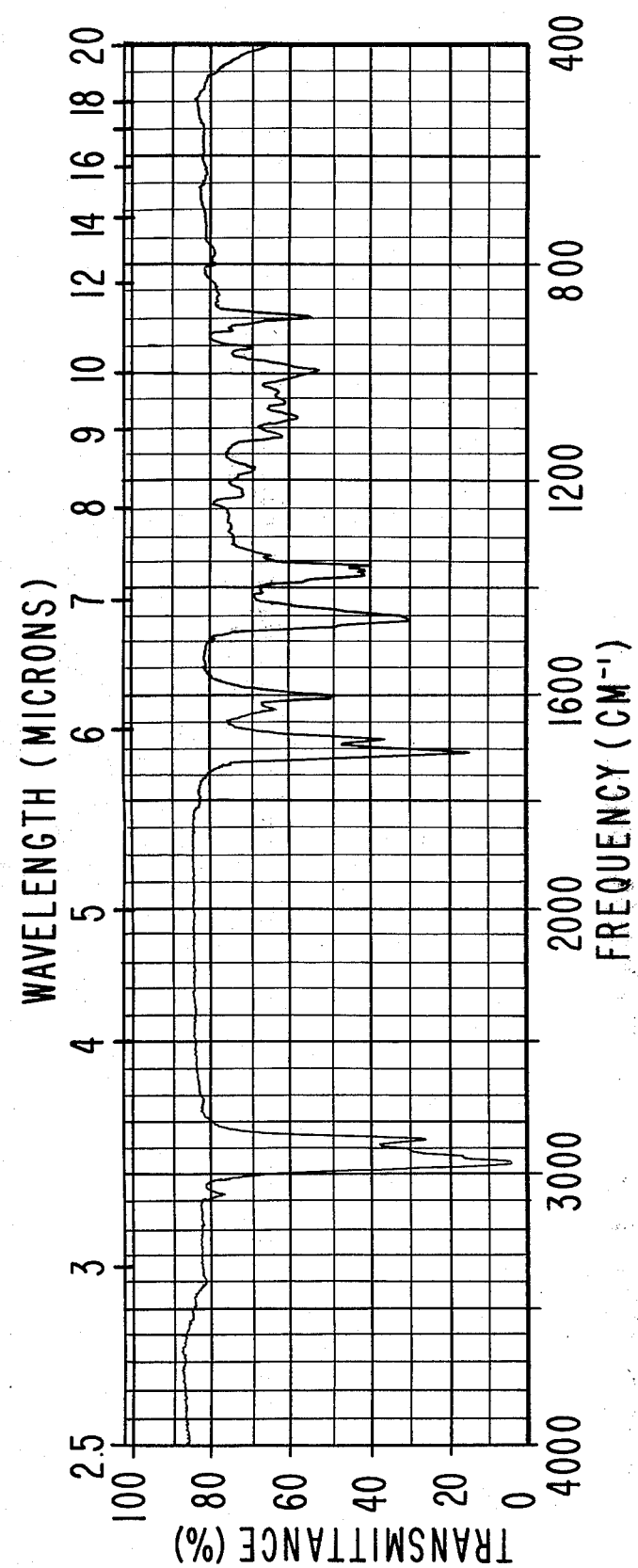

FIG. 10 represents the infra-red spectrum for the reaction product of Example IV containing the compounds having the structures:

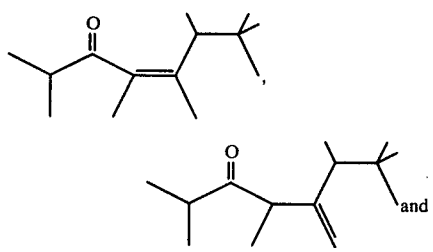

and

Figure 11:
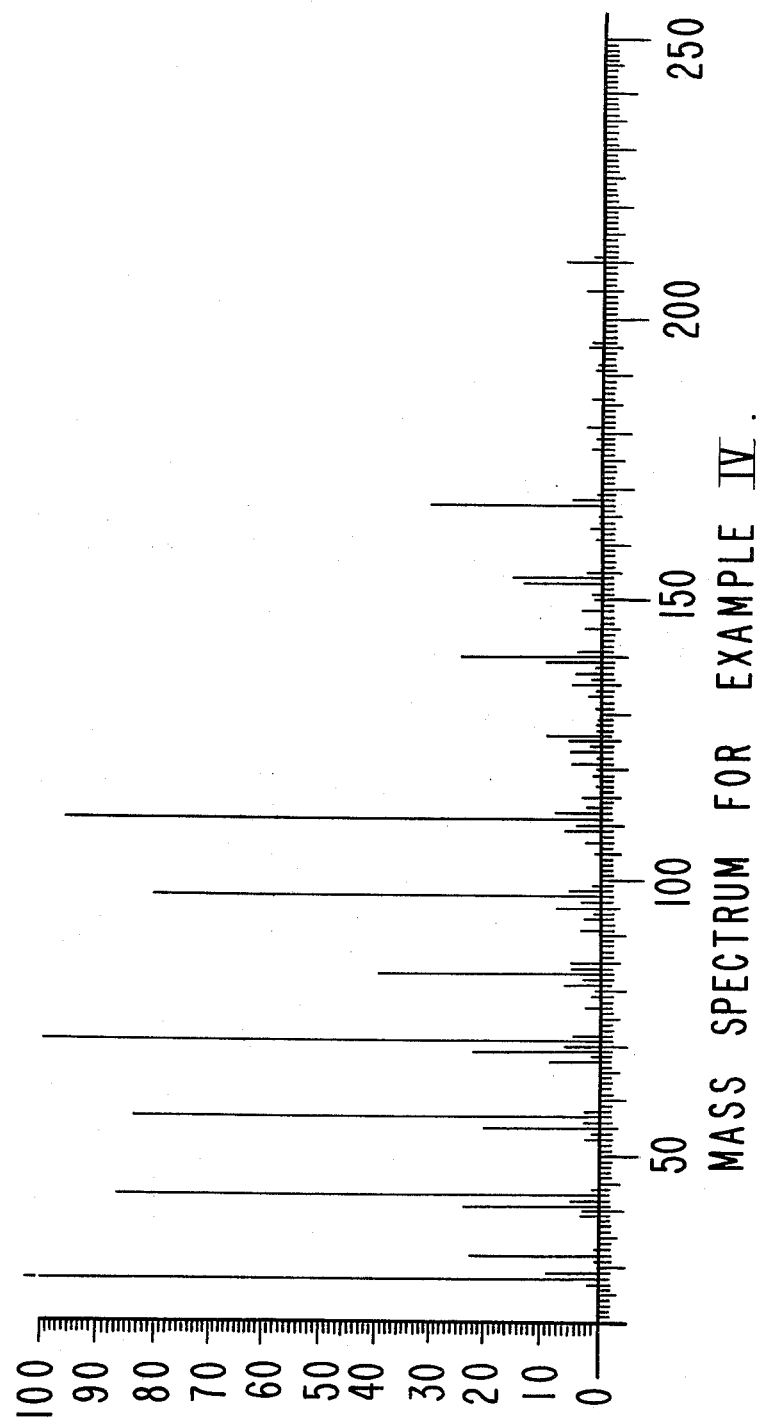

FIG. 11 represents the mass spectrum for the reaction product of Example IV containing the compounds having the structures:

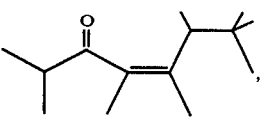

,

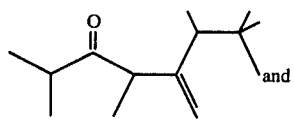

and

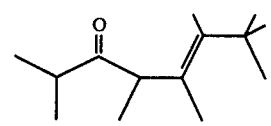

Figure 12:
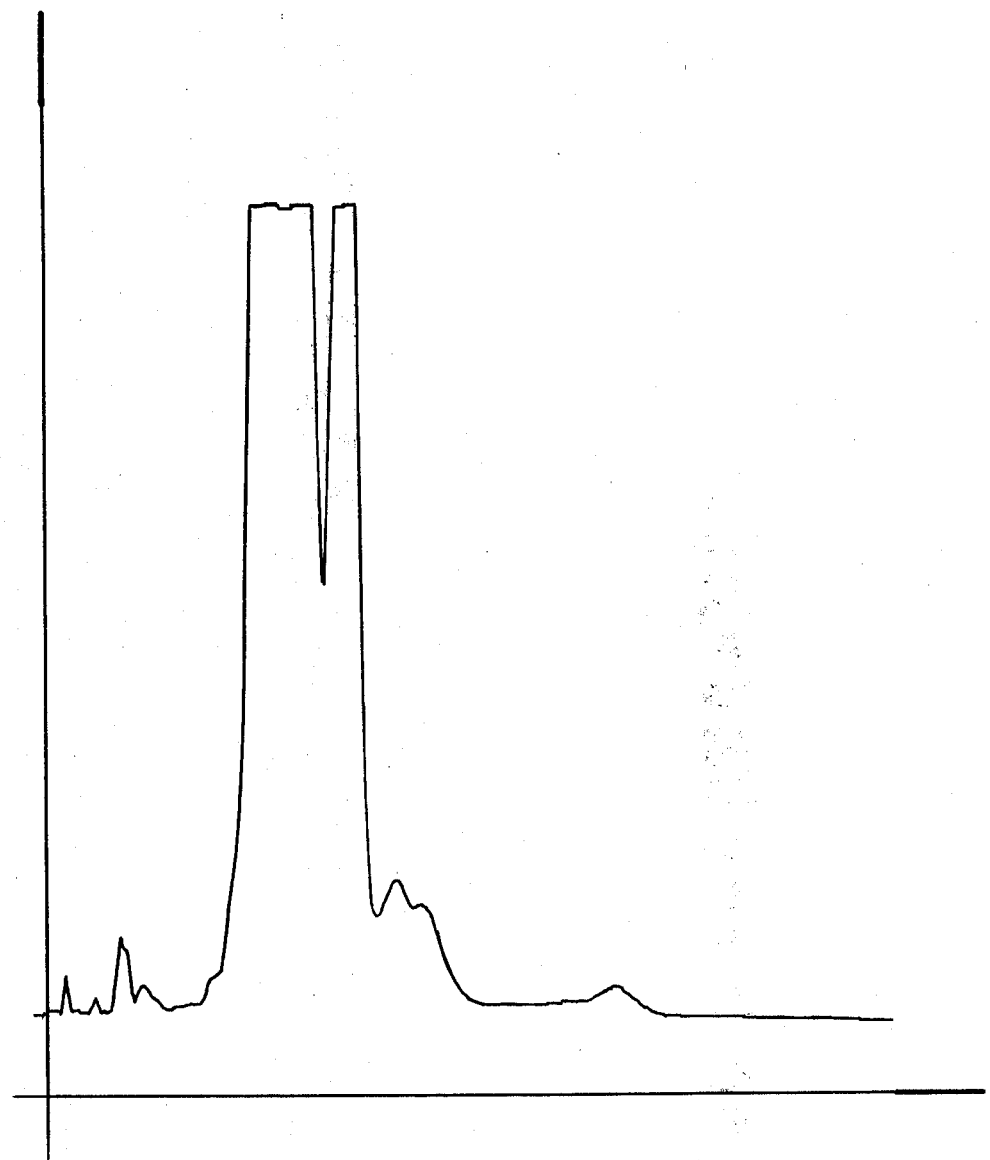

FIG. 12 represents the GLC profile for the reaction product of Example VA containing structures defined according to the genus having the structure:

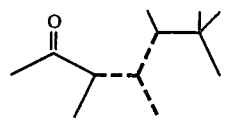

wherein in each of the molecules of the mixture, one of the dashed lines represents a carbon-carbon double bond and each of the other of the dashed lines represent carbon-carbon single bonds.

Figure 13:
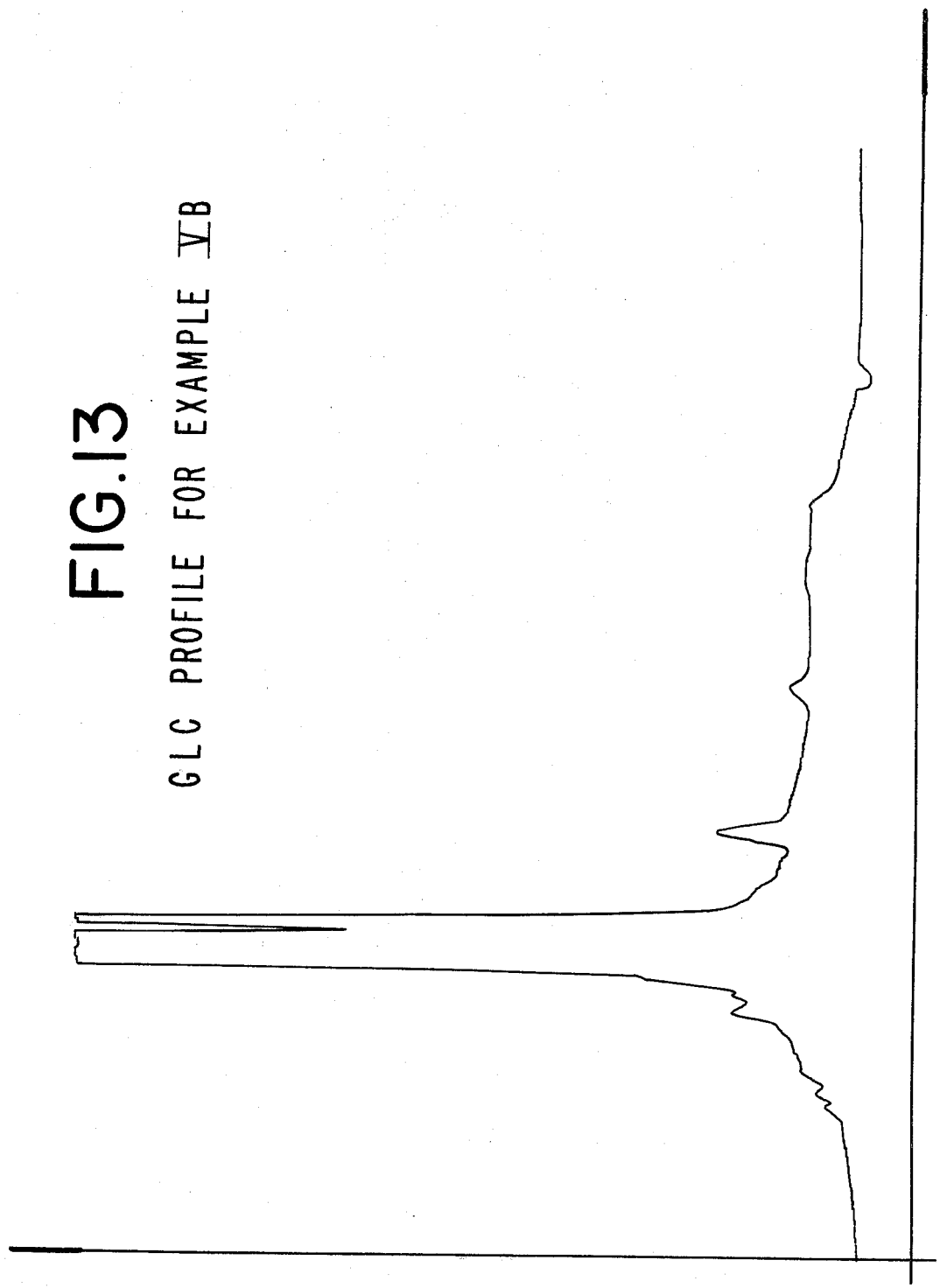

FIG. 13 represents the GLC profile for the reaction product of Example VB containing a mixture of compounds defined according to the structure:

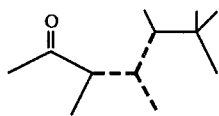

wherein in each of the molecules of the mixture, one of the dashed lines represents a carbon-carbon double bond and each of the other of the dashed lines represent carbon-carbon single bonds.

Figure 14:
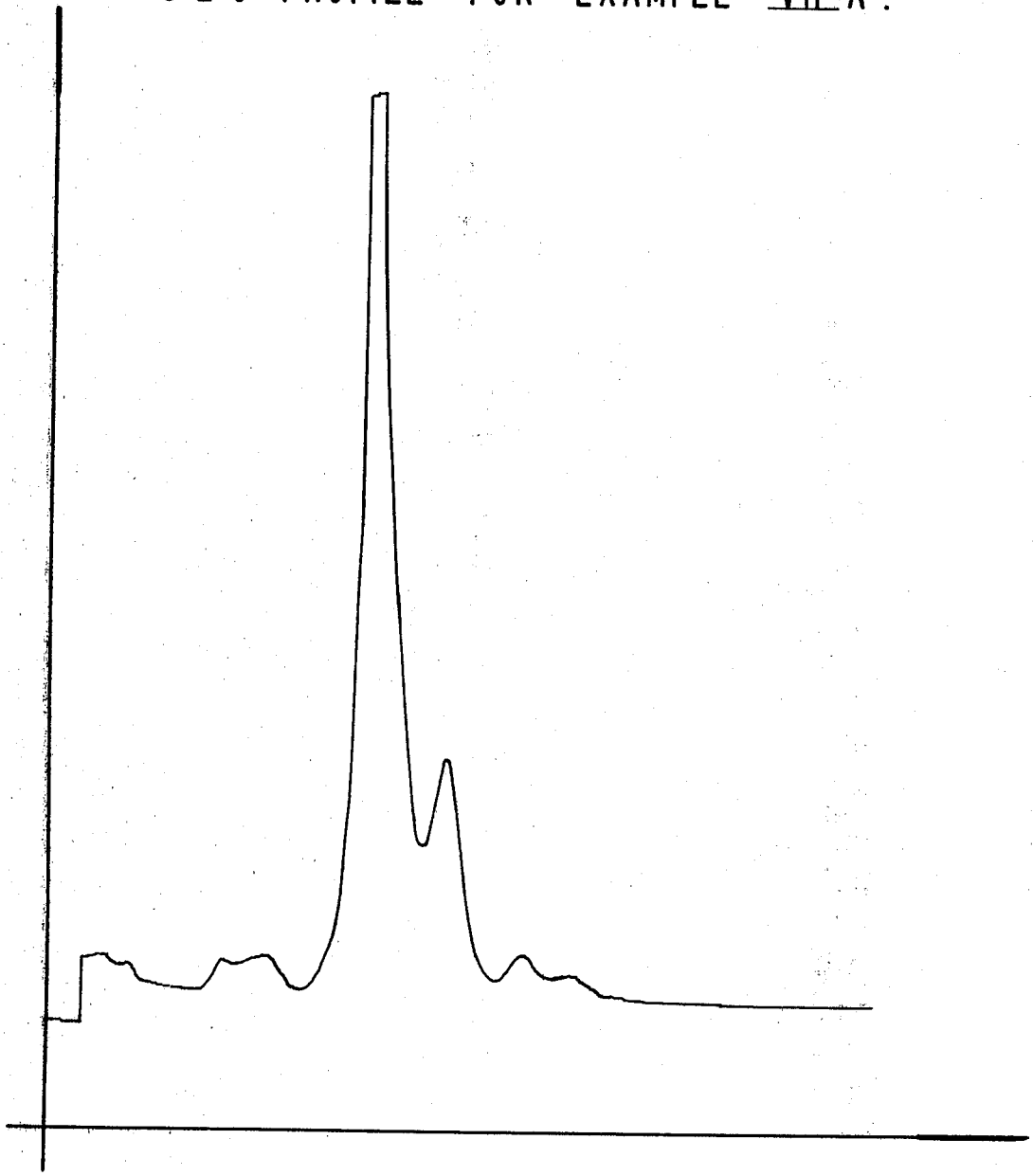

FIG. 14 represents the GLC profile for the reaction product of Example VIIA containing a mixture of compounds defined according to the genus having the structure:

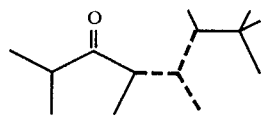

wherein in each of the molecules of the mixture, one of the dashed lines represents a carbon-carbon double bond and each of the other of the dashed lines represents carbon-carbon single bonds.

THE INVENTION

As discussed in Application for U.S. Pat. No. 160,788 filed on June 19, 1980 now U.S. Pat. No. 4,287,084 issued on Sept. 1, 1981, it has been recently ascertained that isoamylene may be dimerized to provide an inexpensive, highly useful, hydrocarbon material having commercially useful and commercially significant organoleptic properties in the field of perfumery. Thus, when isoamylene is dimerized, the following reaction takes place:

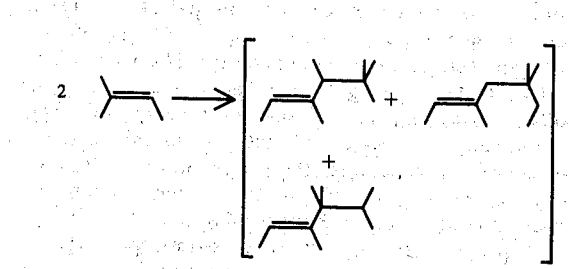

yielding the products having the structures:

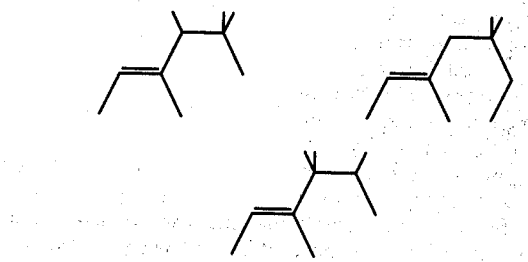

The compounds having the structures:

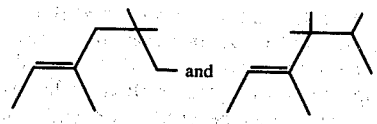

depolymerize to form t-amylene, which, in turn, repolymerizes to form the compound having the structure:

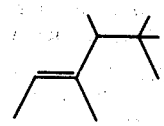

Thus, the dimerization product of diisoamylene is further reacted to form other significantly useful perfumery products, food flavor products and other organoleptically useful materials by means of acylation with either an acyl halide, or an acyl-anhydride according to the generic reaction:

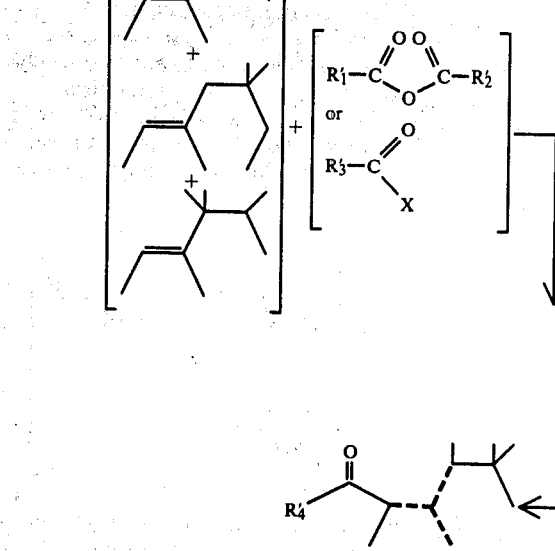

wherein $R_4'$ represents $C_1$-$C_3$ alkyl; wherein $R_1'$, $R_2'$ and $R_3'$ are the same or different and each represents $C_1$-$C_3$ alkyl; and wherein X is halogen selected from the group consisting of chloro or bromo; and wherein in each of the molecules, one of the dashed lines represents a carbon-carbon double bond and the other dashed lines represent carbon-carbon single bonds.

Thus, it has now been discovered that novel solid and liquid foodstuff, chewing gum, medicinal products, toothpastes and chewing tobacco compositions, and flavoring compositions therefor having woody, citrus, floral, ionone-like, incense-like, oriental, grapefruit-like, piney, fruity and rosin-like aroma nuances as well as woody, citrus, floral, ionone-like, oriental, grapefruit-like, piney, fruity and rosin-like taste nuances with bitter undertones; as well as novel tobacco and tobacco flavoring compositions having sweet, woody, oriental, camphoraceous, fruity and spicey aroma and taste nuances prior to smoking, and woody, peppery and oriental-like aroma and taste nuances on smoking, in both the mainstream and the sidestream; as well as novel perfume compositions, colognes and perfumed articles (e.g. solid or liquid anionic, cationic, nonionic and zwitterionic detergents; cosmetic powders, hair preparations; fabric softener compositions; and dryer-added fabric softener articles) having an intense and long-lasting sweet, rich, warm woody, fruity, amber, rum/cognac-like, sandalwood, sweet floral and vetiver-like aroma nuances with patchouli top-notes as well as minty undertones, may be provided by the utilization of one or more branched acyclic, unsaturated ketone derivatives, defined according to the generic structure:

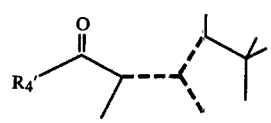

wherein $R_4'$ represents $C_1$-$C_3$ lower alkyl; wherein in each molecule, one of the dashed lines represents a carbon-carbon double bond and the other of the dashed lines represent carbon-carbon single bonds.

Unless otherwise specified, representation herein of carbon-carbon double bonds are intended to indicate a "cis" isomer, a "trans" isomer, or a mixture of "cis" and "trans" isomers with respect to that carbon-carbon double bond in the event that the carbon-carbon double bond is susceptible of such "cis-trans" isomerism.

The novel branched, unsaturated ketones of our invention may be prepared by first preparing diisoamylene as by dimerizing isoamylene according to the reaction:

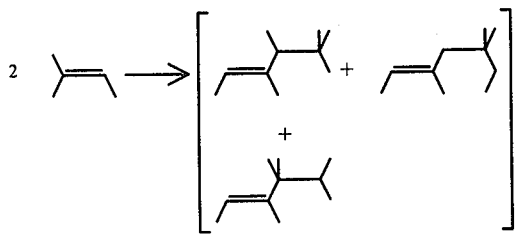

The resulting diisoamylene material thus produced, is used "as is" in the subsequent acylation reaction. Thus, for example, the subsequent acylation reaction may be carried out on the mixture of diisoamylene molecules according to the reaction:

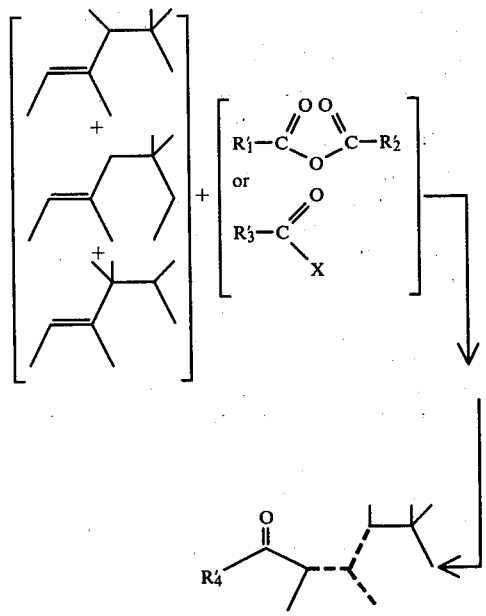

wherein the acylation is carried out using an organic acid anhydride or a mixed anhydride, or an acyl halide.

In the foregoing reaction, $R_1'$, $R_2'$ and $R_3'$ represent the same or different $C_1$–$C_3$ alkyl, methyl, ethyl, n-propyl or i-propyl; and X represents chloro or bromo; and one of the dashed lines in the reaction product represents a carbon-carbon double bond, and each of the other of the dashed lines represent carbon-carbon single bonds. This reaction is carried out in the presence of an acid catalyst, which may be either a Lewis acid or a mineral acid. When using Lewis acids, such as boron trifluoride etherate, zinc chloride, aluminum chloride, zinc bromide, diethyl aluminum chloride, ethyl aluminum dichloride, stannic chloride or zinc bromide, the temperature of reaction may vary between 0° C. and 80° C., with a preferred reaction temperature of between 10° C. and 50° C. When using a mineral acid, such as, methane sulfonic acid, sulfuric acid, phosphoric acid, polyphosphoric acid, or a mixture of methane sulfonic acid and phosphorous pendoxide, the temperature of reaction may vary between 25° C. and 150° C. with a preferred reaction temperature of between 40° C. and 110° C.

The mole ratio of dimer of isoamylene:acylating agent (e.g., acyl anhydride) may vary between 1:1.1 and 2:1.0, with a preferable mole ratio of diisoamylene dimer:acylating agent being about 1:0.7. Various acyl anhydrides or acyl halides may be used, for example:

Acetic anhydride
Propionic anhydride
n-butyric anhydride
i-Butyric anhydride
Acetic propionic anhydride
Acetic n-butyric anhydride
Acetic i-butyric Anhydride
Propionic i-butyric anhydride
Propionic n-butyric anhydride The concentration of catalysts in the reaction mass may vary from 2.5 weight percent to 150 weight percent with a preferred concentration (Lewis acid or mineral acid) being between 5 and 10% by weight of the reaction mass.

Although an inert solvent may be used in the reaction mass (e.g., benzene, toluene, xylene, dichloromethane or 1,2-dichlorobenzene) it is preferred that no solvents be used, and that the reaction mass be carried out in the absence of solvent.

Although pressures greater than or less than atmospheric pressure may be used, no specific advantages are seen in using higher or lower pressures insofar as conversion, yield or time of reaction is concerned.

Accordingly, it is most preferred to use atmospheric pressure as a reaction condition.

The following table sets forth specific reaction products contemplated within the scope of our invention, and their individual organoleptic properties; that is insofar as smoking tobacco aroma and taste are concerned, food flavor is concerned, and perfume aroma is concerned:

TABLE I

| Structure of Reaction Product | Fragrance Properties | Foodstuff Flavor Properties | Smoking Tobacco Flavor & Aroma Properties |
|---|---|---|---|
| 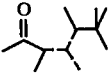 prepared according to Ex. V(B) infra (mixture of compounds | Fruity, woody, and amber aroma | Woody, citrus floral aroma with a woody, citrus, floral taste | |

TABLE I-continued

| Structure of Reaction Product | Fragrance Properties | Foodstuff Flavor Properties | Smoking Tobacco Flavor & Aroma Properties |
|---|---|---|---|
| wherein one of the dashed lines in one of the molecules represents a carbon-carbon double bond and each of the other of the dashed lines in that molecule represents a carbon-carbon single bond) | | | |
| 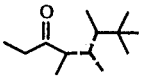 prepared according to Ex. II, infra | Sweet, fruity floral, woody amber aroma | | |
| 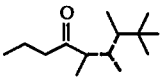 prepared according to Ex. III, infra | A fruity, woody aroma | A woody, piney, fruity rosin-like aroma and taste | A fruity, spicey aroma and taste, both prior to and on smoking, in the mainstream and the sidestream |
| 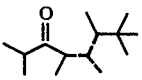 prepared according to Ex. IV, infra | A long-lasting, sweet, rich, warm woody, vetiver-like fruity aroma | A floral, citrusy, grapefruit-like aroma and taste profile | A sweet, woody, oriental, camphoraceous aroma prior to smoking and a woody peppery aroma and taste on smoking, in both the mainstream and the side-stream |
| 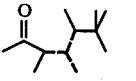 prepared according to Ex. I, infra | A warm, woody amber aroma with a patchouli topnote and a minty undertone | A floral, ionone, incense-like and oriental aroma with an ionone and oriental-like flavor profile | |
| 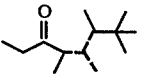 prepared according to Ex. VI, infra | A rum/cognac-like, amber, woody, (sandalwood-like) aroma | An ionone-like and oriental-like aroma and taste profile, with bitter nuances | |
| 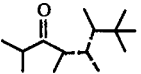 prepared according to Ex. VII, infra | A sweet, woody, fruity, vetiver-like aroma with a pleasant, charred or burnt sugar-like nuance | A burnt sugar-like pineapple aroma and taste profile | |
| 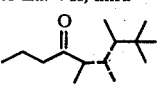 | A full-bodied long-lasting powerful, woody aroma. | | |

As used herein, the term "medicinal product" includes both solids and liquids which are ingestible non-toxic materials which have medicinal value such as cough syrups, cough drops, aspirin and chewable medicinal tablets.

The term "chewing gum" is intended to mean a composition which comprises a substantially water-insoluble, chewable plastic gum base such as chicle, or substitutes therefor, including jelutong, guttakay, rubber or certain cosmetible natural or synthetic resins or waxes. Incorporated with the gum base in admixture therewith may be plasticizers or softening agents, e.g., glycerine; and a flavoring composition which incorporates one of the unsaturated branched-chain ketones of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole(mixture of 2- and 3-tertiary-butyl-4-hydroxyanisole), butylated hydroxytoluene (2,6-di-tertiary-butyl-4-methylphenol), propyl gallate and the like and sequestrants, e.g., citric acid.

Thickener compounds include carriers, binders, protective colloids, suspending agents, emulsifiers and the like, e.g., agar agar, carrageenan, cellulose and cellulose derivatives such as carboxymethyl cellulose and methyl cellulose; natural and synthetic gums such as gum arabic, gum tragacanth; gelatin, proteinaceous materials; lipids, carbohydrates; starches, pectins, and emulsifiers, e.g., mono and diglycerides of fatty acids, skim milk powder, hexoses, pentoses, disaccharides, e.g., sucrose, corn syrup and the like.

Surface active agents include emulsifying agents, e.g., fatty acids such as capric acid, caprylic acid, palmitic acid, myristic acid and the like, mono and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anticaking agents, e.g., aluminum calcium sulfate and tribasic calcium phosphate; enzymes; yeast foods, e.g. calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include aldehydes, esters, natural oils, alcohols, sulfides, ketones, lactones, carboxylic acids and hydrocarbons such as heliotropin, terpineol-4, benzaldehyde, anisaldehyde, phenyl acetaldehyde, benzyl formate, benzyl acetate, cis-3-hexenyl benzoate, methyl hexanoate, hexanal, eucalyptol, eugenol, acetaldehyde, ethyl acetate, ethyl butyrate, turpentine gum oil, limonene, gum camphor, isobornyl acetate, borneol, cinnamic aldehyde, cuminic aldehyde, furfural, methyl cinnamate, cassia oil, vanillin, maltol, parahydroxybenzyl acetone, dimethyl sulfide, alpha-ionone, acetic acid, isobutyl acetate, acetone, butyric acid, formic acid, valeric acid, amyl acetate, amyl butyrate, anethol, benzyl salicylate, diacetyl, dimethyl anthranilate, ethyl methylphenylglycidate, ethyl succinate, ethyl valerate, geraniol, cis-3-hexen-1-ol, 2-hexenyl acetate, 2-hexenyl butyrate, 4-(p-hydroxyphenyl)-2-butanone, beta-ionone, isobutyl cinnamate, jasmine, lemon essential oil, methyl butyrate, methyl caproate, methyl disulfide, methyl p-naphthyl ketone, orris butter, rose absolute, terpenyl acetate, gammaundecalactone, vanilla and alcohol.

The specific flavoring adjuvant selected for use may be either solid or liquid depending upon the desired physical form of the ultimate product, i.e., foodstuff, whether simulated or natural, should, in any event, (i) be organoleptically compatible with the unsaturated branched-chain ketone derivatives of our invention by not covering or spoiling the organoleptic properties (aroma and/or taste) thereof; (ii) be nonreactive with the unsaturated branched-chain ketone derivatives of our invention and (iii) be capable of providing an environment in which the unsaturated branched-chain ketone derivatives can be dispersed or admixed to provide homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g. simulated foodstuffs, ingredients capable of provuding normally solid compositions should be selected such as various cellulose derivatives.

As will be appreciated by those skilled in the art, the amount of unsaturated branched-chain ketones employed in a particular instance can vary over a relatively wide range, depending upon the desired organoleptic effects to be achieved Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e., sufficient to alter, modify or enhance the organoleptic characteristics of the parent composition, whether foodstuff per se, chewing gum, per se, medicinal product per se, toothpaste per se, or flavoring composition.

The use of insufficient quantities of unsaturated branched-chain ketones will, of course, substantially vitiate any possibility of obtaining the desired results while excess quantities prove needlessly costly and, in extreme cases, may disrupt the flavor-aroma balance, thus proving self defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of unsaturated branched-chain ketones ranging from a small, but effective amount, 0.05 parts per million up to about 100 parts per million based on total composition are suitable. Concentrations in excess of the maximum quantity stated are not normally recommended, since they fail to prove commensurate enhancement of organoleptic properties. In those instances, wherein the unsaturated branched-chain ketones are added to the foodstuff as an integral component of a flavoring composition, it is, of course, essential that the total quantity of flavoring composition employed be sufficient to yield an effective unsaturated branched-chain ketones concentration in the foodstuff product.

Food flavoring compositions prepared in accordance with the present invention preferably contain the unsaturated branched-chain ketones in concentrations ranging from about 0.1% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency. homogeneity of dispersion, etc. Alternatively, flavoring compositions in the form of particulate solids can be conveniently prepared by mixing the unsaturated branched-chain ketones with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix are obtained by mixing the dried solid components, e.g., starch, sugar and the like and the unsaturated branched-chain ketones in a dry blender until the requisite degree of uniformity is achieved.

It is presently preferred to combine with the unsaturated branched-chain ketones of our invention, the following adjuvants:
Heliotropin;
Terpineol-4;
Benzaldehyde;
Anisaldehyde;
Phenyl acetaldehyde;
Benzyl formate;
Benzyl acetate;
Cis-3-hexenyl benzoate;
Methyl Hexanoate;
Hexanal;
Eucalyptol;
Eugenol;
Acetaldehyde;
Ethyl acetate;
Ethyl butyrate;
Turpentine gum oil;
Limonene;
Gum camphor;
Isobornyl acetate;
Borneol;
Cinnamic aldehyde;
Cuminic aldehyde;
Furfural;
Methyl cinnamate;
Cassia oil;
Vanillin;
Maltol;
Parahydroxybenzylacetone;
Dimethyl sulfide;
Alpha-ionone;
Acetic acid;
Isobutyl acetate;
Acetone;
Butyric acid;
Formic acid;
Valeric acid;
Amyl acetate
Amyl butyrate;
Anethol;
Benzyl salicylate;
Diacetyl;
Dimethyl anthranilate;
Ethyl methylphenylglycidate;
Ethyl succinate;
Ethyl valerate;
Geraniol;
Cis-3-hexen-1-ol;
2-Hexenyl acetate;
2-Hexenyl butyrate;
Hexyl butyrate;
4-(p-Hydroxyphenyl)-2-butanone;
Beta-ionone;
Isobutyl cinnamate;
Jasmine;
Lemon essential oil;
Methyl butyrate;
Methyl capronate;
Methyl disulfide;
Methyl p-naphthyl ketone;
Orris butter;
Rose absolute;
Terpenyl acetate;
Gamma-undecalactone;
Vanilla; and
Alcohol.

An additional aspect of our invention provides an organoleptically improved smoking tobacco product and additives therefor, as well as methods of making the same which overcome problems heretofore encountered in which specific desired sweet, woody, oriental, spicey and fruity flavor characteristics of natural "Turkish-like" tobacco (prior to smoking and, on smoking, in the mainstream and in the sidestream) are created or enhanced or modified or augmented and may be readily controlled and maintained at the desired uniform level regardless of variations in the tobacco components of the blend.

This invention further provides improved tobacco additives and methods whereby various desirable natural aromatic tobacco flavoring characteristics with sweet, woody, oriental type, camphoraceous, fruity and spicey, as well as peppery taste and aroma nuances may be imparted to smoking tobacco products, and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient one or more unsaturated branched-chain ketones of our invention.

In addition to the unsaturated branched-chain ketones of our invention other flavoring and aroma additives may be added to the smoking tobacco material or substitute therefor either separately or in mixture with the unsaturated branched-chain ketones as follows:

I. Synthetic Materials

Beta-ethyl-cinnamaldehyde;
Eugenol;
Dipentene;
Damascenone;
Maltol;
Ethyl maltol;
Delta undecalactone;

Delta decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropylacetophenone;
2-Hydroxy-2,5,5,8a-tetramethyl-1-(2-hydroxyethyl)-decahydronaphthalene;
Dodecahydro-3a6,6,9a-tetramethyl-naphtho-(2,1furan
4-Hydroxyhexanoic acid, gamma lactone; and
Polyisoprenoid hydrocarbons defined in Example V of U.S. Pat. No. 3,589,372 issued on June 29, 1971.

II. Natural Oils

Celery seed oil;
Coffee extract;
Bergamot Oil;
Cocoa extract;
Nutmeg Oil; and
Origanum oil.

An aroma and flavoring concentrate containing one or more unsaturated branched-chain ketones of our invention and, if desired, one or more of the above indicated additional flavoring additives may be added to the smoking tobacco material, to the filter or to the leaf or paper wrapper. The smoking tobacco material may be shredded, cured, cased and blended tobacco material or tobacco substitutes (e.g., lettuce leaves) or mixtures thereof. The proportions of flavoring additives may e varied in accordance with taste but insofar as enhancement or the imparting of natural and/or sweet notes and/or woody notes and/or oriental-like notes and/or camphoraceous notes and/or fruity notes and-/or spicey notes and/or peppery notes, we have found that satisfactory results are obtained in the proportion by weight of the sum total of unsaturated branched-chain ketone derivative(s) to smoking tobacco material is between 50 ppm and 1,500 ppm (0.015%–0.15%). We have further found that satisfactory results are obtained if the proportion by weight of the sum total of unsaturated branched-chain ketone derivatives used to flavoring material is between 1,500 and 15,000 ppm (0.15%–1.5%).

Any convenient method for incorporating the unsaturated branched-chain ketone derivative(s) into the tobacco product may be employed. Thus, the unsaturated branched-chain ketone derivative(s) taken alone or along with other flavoring additives may be dissolved in a suitable solvent such as ethanol, diethyl ether and/or volative organic solvents and the resulting solution may either be spread on the cured, cased and blended tobacco material or the tobacco material may be dipped into such solution. Under certain circumstances, a solution of the unsaturated branched-chain ketone derivative(s) taken alone or taken further together with other flavoring additives as set forth above, may be applied by means of a suitable applicator such as a brush or roller on the paper or leaf wrapper for the smoking product, or it may be applied to the filter by either spraying or dipping, or coating.

Furthermore, it will be apparent that only a portion of the tobacco or substitute therefor need be treated and the thus treated tobacco may be blended with other tobaccos before the ultimate tobacco product is formed. In such cases, the tobacco treated may have the unsaturated branched-chain ketone derivative(s) in excess of the amounts or concentrations above indicated so that when blended with other tobaccos, the final product will have the percentage within the indicated range.

In accordance with one specific example of our invention, an aged, cured and shredded domestic burley tobacco is sprayed with a 20% ethyl alcohol solution of the compound having the structure:

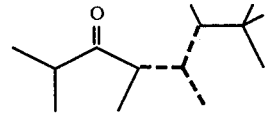

in an amount to provide a tobacco composition containing 800 ppm by weight of said compound on a dry basis. Thereafter, the alcohol is removed by evaporation and the tobacco is manufactured into cigarettes by the usual techniques. The cigarette, when treated as indicated has a desired and pleasing aroma which is defined as woody and peppery with oriental and fruity and spicey undertones detectable in the main and the sidestreams when the cigarette is smoked. This aroma is described as being sweeter, more aromatic, more Turkish tobacco-like and having sweet, fruity, peppery, woody and oriental nuances which cause the burley tobacco to equate Turkish-like.

While our invention is particularly useful in the manufacture of smoking tobacco, such as cigarette tobacco, cigar tobacco and pipe tobacco, other tobacco products, formed from the sheeted tobacco dust or fines may also be used. Likewise, the unsaturated branched-chain ketone derivative(s) of our invention can be incorporated with materials such as filter tip materials (e.g., cellulose acetate filte-s wherein sweet, woody, oriental, spicey and/or fruity effects are desired), seam paste, packaging materials and the like which are used along with tobacco to form a product adapted for smoking. Furthermore, the unsaturated branched-chain ketone derivative(s) can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco of tobacco plant parts or substitute materials or both.

The unsaturated branched-chain ketone derivative(s) and one or more auxiliary perfume ingredients, including, for example, hydrocarbons, alcohols, ketones, aldehydes, nitriles, esters, lactones or cyclic ester, synthetic essential oils and natural essential oils, may be admixed so that the combined odors of the individual components produce a pleasant and desired fragrance, particularly and preferably in the woody, sandalwood-like, patchouli-like, amber and/or vetiver and/or fruity fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume composition, it is the individual components which contribute to their particular olfactory characteristics, however the over-all sensory effect of the perfume composition will be at least the sum total of the effects of each of the ingredients. Thus, one or more of the unsaturated branched-chain ketone derivative(s) of our invention can be used to alter, modify or enhance the aroma characteristics of a perfume composition, for example, by utilizing or moderating the olfactory reaction contributed by another ingredient in the composition.

The amount of unsaturated branched-chain ketone derivative(s) of our invention which will be effective in perfume compositions as well as in perfumed articles and colognes depends on many factors, including the other ingredients, their amounts and the effects which are desired. It has been found that perfume compositions containing as little as 0.01% of unsaturated branched-chain ketone derivative(s) or even less (e.g., 0.005%) can be used to impart a sweet, rich, warm woody, fruity, amber, rum/cognac-like, sandalwood-like, sweet, floral, long-lasting vetiver-like aromas with patchouli top-notes and minty undertones to soaps, cosmetics, detergents (including anionic, nonionic and cationic detergents) or other products. The amount employed can range up to 70% of the fragrance components and will depend on considerations of cost, nature of the end product, the effect desired on the finished product and the particular fragrance sought.

The unsaturated branched-chain ketone derivative(s) of our invention are useful (taken alone or together with other ingredients in perfume compositions) in detergents and soaps, space odorants and deodorants, perfumes, colognes, toilet water, bath preparations, such as lacquers, brillantines, pomades and shampoos; cosmetic preparations, such as creams, deodorants, hand lotions and sun screens; powders, such as talcs, dusting powders, face powders and the like. As little as 1% of the unsaturated branched-chain ketone derivative(s) will suffice to impart an intense piney note to woody perfume formulations. Generally, no more than 3% of the unsaturated branched-chain ketone derivative(s) based on the ultimate end product, is required in the perfume composition.

In addition, the perfume composition or fragrance composition of our invention can contain a vehicle, or carrier for the unsaturated branched-chain ketone derivative(s). The vehicle can be a liquid such as a non-toxic alcohol, a non-toxic glycol, or the like. The carrier can also be an absorbent solid, such as a gum (e.g., gum arabic), or components for encapsulating the composition (such as gelatin).

It will thus be apparent that the unsaturated branched-chain ketone derivative(s) of our invention can be utilized to alter, modify or enhance sensory properties, particularly organoleptic properties, such as flavor(s) and/or fragrance(s) of a wide variety of consumable materials.

The following Example A sets forth procedures for preparing precursors of the compounds of our invention, the unsaturated branched-chain ketones.

The following Examples I–VIII set forth procedures for preparing the unsaturated branched-chain ketones of our invention.

The remainder of the examples set forth the uses of the unsaturated branched-chain ketones of our invention for their organoleptic properties.

It will be understood that these examples are illustrative and that the invention is to be considered restricted thereto, only as indicated in the appended claims.

All parts and percentages given herein are by weight, unless otherwise specified.

EXAMPLE A

PREPARATION OF DI-ISOAMYLENE DERIVATIVES

Reaction:

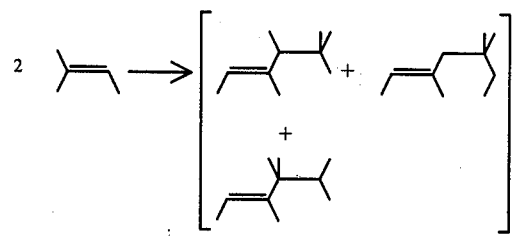

(wherein in each of the molecules indicated, one of the dashed lines is a carbon-carbon double bond and the other of the dashed lines are carbon-carbon single bonds).

Di-isoamylene is prepared according to one of the procedures set forth in the following references:

i - Murphy & Lane, Ind. Eng. Chem., Prod. Res. Dev., Vol. 14, No. 3, 1975 p. 167 (Title: Oligomerization of 2-Methyl-2-Butene in Sulfuric and Sulfuric-Phosphoric Acid Mixtures).

ii - Whitmore & Mosher, Vol. 68, J. Am. Chem. Soc., February, 1946, p. 281 (Title: The Depolymerization of 3,4,5,5-Tetramethyl-2-hexene and 3,5,5-Trimethyl-2-heptene in Relation to the Dimerization of Isoamylenes)

The resulting material was distilled in a fractionation column in order to separate the di-isoamylene from the higher molecular weight polymers, which are formed during the reaction as by-products.

BRIEF DESCRIPTION OF THE DRAWINGS

Figure AA represents the GLC profile for the reaction product of Example A using a 70% sulfuric acid catalyst at 35%C.

Figure AB represents the GLC profile for the reaction product of Example A using an Amberlyst ® 15 acidic ion exchange resin catalyst at a temperature of 150° C.

Figure AC represents the GLC profile for the reaction product of Example A, using an Amberlyst ® 15 catalyst at 100° C.

Figure AD represents the GLC profile for the reaction product of Example A, using a sulfuric acid catalyst and an alpha-methylstyrene diluent at 35° C. according to the conditions of United Kingdom Pat. No. 796,130 (crude reaction product).

Figure AE represents the GLC profile for the reaction product of Example I, using a sulfuric acid catalyst, at 35° C. and an alpha-methyl styrene diluent according to the conditions of United Kingdom Pat. No. 796,130 (distilled reaction product).

Figure BA represents the NMR spectrum for Peak 1 of the GLC profile of Figure AE.

Figure BB represents the infra-red spectrum for Peak 1 of the GLC profile of Figure AE.

Figure CA represents the NMR spectrum for Peak 2 of the GLC profile of Figure AE.

Figure CB represents the infra-red spectrum for Peak 2 of the GLC profile of Figure AE.

Figure D represents the NMR spectrum for Peak 2 of the GLC profile of Figure AB.

EXAMPLE I

PREPARATION OF ACETYL DERIVATIVE OF DIISOAMYLENE

Reaction:

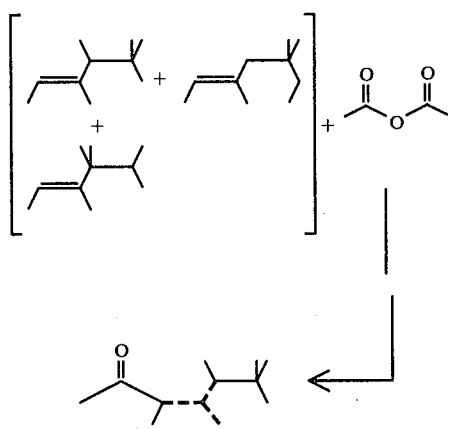

wherein in each of the structures containing dashed lines, these structures represent mixtures of molecules wherein in each of the molecules, one of the dashed lines represents a carbon-carbon double bond and each of the other of the dashed lines represent carbon-carbon single bonds.

Into a 2-liter reaction flask equipped with stirrer, thermometer, reflex condenser and heating mantle, is placed 1000 g of acetic anhydride and 80 g of boron trifluoride diethyl etherate. The resulting mixture is heated to 80° C. and, over a period of 40 minutes, 690 g of diisoamylene prepared according to the illustration in Example A, supra is added. The reaction mass is maintained at 82°–85° C. for a period of 5.5 hours, whereupon it is cooled to room temperature. The reaction mass is then added to one liter of water and the resulting mixture is stirred thereby yielding two phases; an organic phase and an aqueous phase. The organic phase is separated from the aqueous phase and neutralized with two liters of 12.5% sodium hydroxide followed by one liter of saturated sodium chloride solution. The resulting organic phase is then dried over anhydrous sodium sulfate and distilled in a one plate distillation column, yielding the following fractions:

| Fraction No. | Vapor Temp. (°C.) | Liquid Temp. (°C.) | mm/Hg Pressure | Weight of Fraction (g.) |
|---|---|---|---|---|
| 1 | 33/68 | 62/77 | 8/8 | 161 |
| 2 | 69 | 79 | 4 | 100 |
| 3 | 72 | 86 | 3.0 | 191 |
| 4 | 88 | 134 | 3.0 | 189 |

The resulting material is then distilled on a multi-plate fractionation column, yielding the following fractions at the following reflux ratios:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 30/65 | 62/83 | 5/5 | 9:1 | 30.8 |
| 2 | 68 | 84 | 5 | 9:1 | 52.8 |
| 3 | 68 | 85 | 5 | 9:1 | 34 |
| 4 | 69 | 87 | 5 | 9:1 | 43 |
| 5 | 69 | 87 | 5 | 9:1 | 34 |
| 6 | 71 | 88 | 4 | 4:1 | 41 |
| 7 | 70 | 88 | 5 | 4:1 | 36.5 |
| 8 | 71 | 91 | 5 | 4:1 | 42 |
| 9 | 73 | 95 | 3 | 4:1 | 42.5 |
| 10 | 80 | 106 | 3 | 4:1 | 39 |
| 11 | 80 | 142 | 3 | 4:1 | 50.8 |
| 12 | 80 | 220 | 3 | 4:1 | 24 |

GLC, NMR, IR and mass spectral analyses yield the information that the resulting material is a mixture of cis and trans isomers having a generic structure:

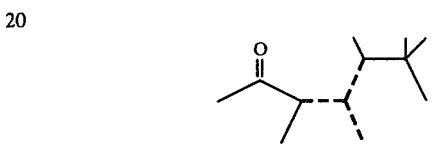

wherein in each of the molecules, one of the dashed lines is a carbon-carbon double bond and the other of the dashed lines is a carbon-carbon single bond and, primarily, this mixture contains the molecular species (cis and trans isomers) as follows:

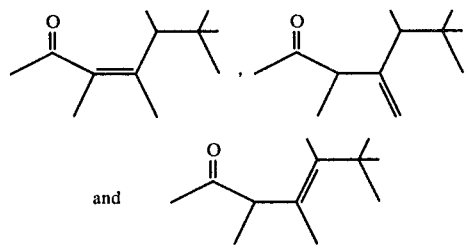

and

FIG. 1 sets forth the GLC profile for the reaction product of Example I, containing compounds defined according to the structure:

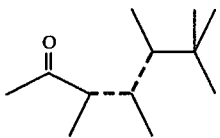

wherein in each molecule of the mixture, one of the dashed lines is a carbon-carbon double bond and the other of the dashed lines are carbon-carbon single bonds.

FIG. 2A represents the infra-red spectrum of Peak 3 of the GLC profile of FIG. 1.

FIG. 2B represents the infra-red spectrum of Peak 4 of the GLC profile of FIG. 1.

FIG. 2C represents the infra-red spectrum for Peak 5 of the GLC profile of FIG. 1.

FIG. 2D represents the infra-red spectrum for Peak 7 of the GLC profile of FIG. 1.

FIG. 2E represents the infra-red spectrum for Peak 7 of the GLC profile of FIG. 1.

FIG. 2F represents the infra-red spectrum for Peak 8 of the GLC profile of FIG. 1.

FIG. 2G represents the infra-red spectrum for Peak 9 of the GLC profile of FIG. 1. produced according to Example I.

FIG. 2K represents the NMR spectrum for the compound having the structure:

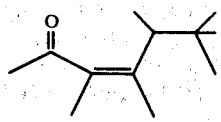

produced according to Example I.

FIG. 2L represents the NMR spectrum for the compound containing the structure:

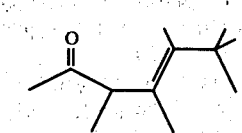

produced according to Example 1.

EXAMPLE II

PREPARATION OF PROPIONYL DERIVATIVE OF DIISOAMYLENES

Reaction:

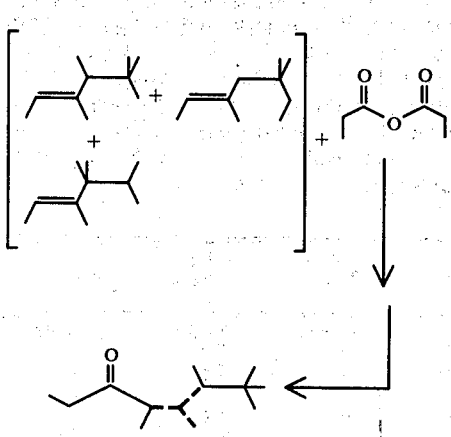

wherein in each of the structures containing dashed lines, these structures represent mixtures of molecules wherein in each of the molecules, one of the dashed lines represents a carbon-carbon double bond and each of the other of the dashed lines represent carbon-carbon single bonds.

Into a 5-liter reaction flask equipped with reflux condenser, addition funnel, thermometer, "Thermowatch", heating mantle and nitrogen purge accessory is placed 1000 g (7.45 moles) of propionic anhydride, 94% and 91.4 ml (0.745 moles) of boron trifluoride etherate. The resulting mixture is heated to 65° C. Over a twenty-five minute period, 1,501 ml (7.45 moles) of the diisoamylene prepared according to the illustration of Example A is added while maintaining the reaction mass at 65°-70° C. The reaction mass is then stirred for a period of thirty minutes at 65° C. whereupon it is cooled and poured into a 3 liter separatory funnel. 75 ml water is then added, followed by 75 ml 50% aqueous sodium hydroxide and another 25 ml water. The reaction mass is then poured into a 4 liter beaker and cooled to room temperature using a dry ice-isopropyl alcohol bath. The reaction mass is then added to a 5-liter separatory funnel and the lower aqueous layer is removed. The upper organic phase is washed with 500 cc of saturated sodium chloride. The organic phase is then washed with 500 cc 5% sodium hydroxide followed by 500 cc saturated sodium chloride, followed by 500 cc of 5% sodium hydroxide. The pH of the oil is now in a range of 6-7. The oil is then again washed with 500 cc saturated sodium chloride.

The aqueous phase is extracted with 400 ml diethyl ether. The resulting material is then distilled on a two inch splash column yielding the following fractions:

| Fraction No. | Vapor Temp. (°C.) | Liquid Temp. (°C.) | mm/Hg Pressure | Weight of Fraction (g.) |
|---|---|---|---|---|
| 1 | 25/75 | 60/85 | 50/50 | 144 |
| 2 | 74 | 87 | 38 | 184 |
| 3 | 34 | 40 | 4 | 186 |
| 4 | 55 | 78 | 3 | 212 |
| 5 | 87 | 94 | 3 | 181 |
| 6 | 95 | 114 | 3 | 210 |
| 7 | 170 | 155 | 3 | 80 |
| 8 | 160 | 225 | 3 | 42 |

Fractions 5, 6 and 7 are then bulked for redistillation and the bulked material is distilled on a one-inch Goodloe Silver Mirror Column, yielding the following fractions:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 17/60 | 81/90 | 3/1.4 | 1:4 | 42 |
| 2 | 58 | 89 | 1.0 | 4:1 | 48 |
| 3 | 63 | 93 | 1.0 | 4:1 | 37 |
| 4 | 68 | 94 | 1.0 | 4:1 | 48 |
| 5 | 70 | 94 | 1.0 | 4:1 | 43 |
| 6 | 72 | 95 | 1.8 | 2:1 | 39 |
| 7 | 72 | 94 | 1.7 | 2:1 | 87 |
| 8 | 74 | 108 | 1.6 | 2:1 | 48 |
| 9 | 82 | 135 | 1.6 | 2:1 | 48 |
| 10 | 110 | 220 | 1.0 | 2:1 | 37 |

Fractions 2-10 are then bulked and redistilled on a 1-foot Goodloe Silver Mirror Column, again yielding the following fractions:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 52/58 | 83/85 | 1.4/1.2 | 4:1 | 46 |
| 2 | 59 | 86 | 1.1 | 4:1 | 50 |
| 3 | 61 | 89 | 1.1 | 4:1 | 53 |
| 4 | 61 | 89 | .9 | 4:1 | 57 |
| 5 | 61 | 91 | .8 | 4:1 | 44 |
| 6 | 61 | 91 | .8 | 4:1 | 41 |
| 7 | 65 | 101 | .8 | 4:1 | 42 |
| 8 | 68 | 115 | .8 | 4:1 | 49 |
| 9 | 74 | 135 | .8 | 4:1 | 17 |
| 10 | 88 | 230 | .8 | 4:1 | 17 |

The resulting material is analyzed using GLC, IR, mass spectral and NMR analyses, yielding information that the resulting material is a mixture of compounds defined according to the generic structure:

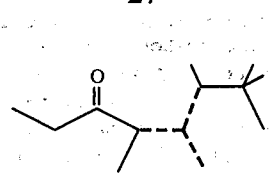

wherein in each molecule of the mixture, one of the dashed lines is a carbon-carbon double bond and each of the other of the dashed lines are carbon-carbon single bonds.

FIG. 3 represents the GLC profile for the reaction product of Example II containing a mixture of compounds, each of which is defined according to the generic structure:

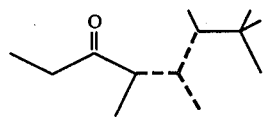

wherein in each molecule one of the dashed lines is a carbon-carbon double bond and each of the other of the dashed lines are carbon-carbon single bonds.

FIG. 4 represents the infra-red spectrum for the product produced according to Example II containing the compounds having the structures:

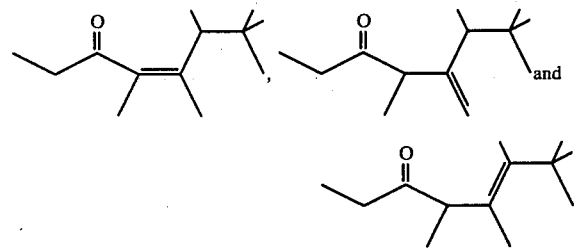

FIG. 5 represents the mass spectrum for the reaction product of Example II, containing the compounds having the structures:

EXAMPLE III

PREPARATION OF n-BUTYRYL DERIVATIVE OF DIISOAMYLENE

Reaction:

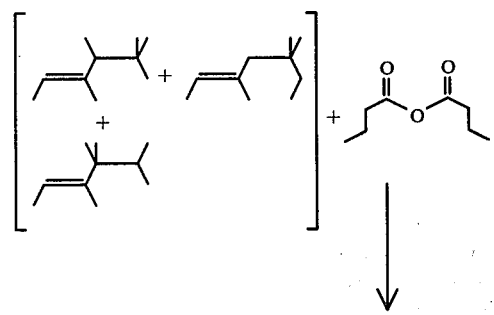

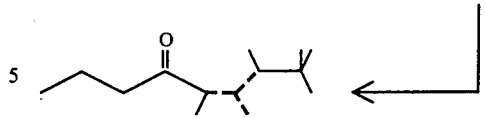

wherein in each of the structures containing dashed lines, these structures represent mixtures of molecules wherein in each of the molecules, one of the dashed lines represents a carbon-carbon double bond and each of the other of the dashed lines represent carbon-carbon single bonds.

Into a 5-liter reaction flask equipped with electric stirrer, heating mantle, thermometer, 24/40 "Y" joint, addition funnel and reflux condenser is added 960 g of n-butyric anhydride, followed by 105 ml boron trifluoride. The resulting mixture is heated to 65° C. and a Thermowatch is attached (reaction must not exceed a pot temperature of 65° C.).

The reaction mass is heated to 65° C. and dropwise addition of 1,725 ml of diisoamylene, prepared according to the illustration of Example A is added over a period of 3.5 hours while maintaining the reaction mass at a temperature of 65° C.

At the end of the addition, the reaction mass is cooled to 38° C. and then transferred to a 5-liter separatory funnel. 75 ml of 50% aqueous sodium hydroxide and 100 ml water are then added to the reaction mass. The reaction mass now exists in two phases; an aqueous phase and an organic phase. The organic phase is washed with one liter of saturated sodium chloride solution thereby creating a pH 4–5. The reaction mass is then washed with 1-liter of 12.5% sodium hydroxide, stirred for fifteen minutes, and then separated. The resulting organic phase is then dried over anhydrous magnesium sulfate and distilled on a 1-inch Stone column yielding the following fractions:

| Fraction No. | Vapor Temp. (°C.) | Liquid Temp. (°C.) | mm/Hg Pressure |
|---|---|---|---|
| 1 | 40/46 | 63/65 | 30/20 |
| 2 | 66 | 77 | 40 |
| 3 | 66 | 77 | 35 |
| 4 | 66 | 87 | 33 |
| 5 | 69 | 90 | 20 |
| 6 | 64 | 100 | 15 |
| 7 | 95 | 110 | 2 |
| 8 | 97 | 110 | 2 |
| 9 | 125 | 160 | 2 |

The resulting fractions 7, 8 and 9 are bulked and redistilled on a 2 foot stainless steel column yielding the following fractions:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 47/74 |  | 1.8 | 4:1 | 53 |
| 2 | 74 | 105 | 1.4 | 4:1 | 85 |
| 3 | 74 | 107 | 1.4 | 4:1 | 96 |
| 4 | 74 | 107 | 1.4 | 4:1 | 89 |
| 5 | 70 | 105 | 1.0 | 4:1 | 66 |
| 6 | 75 | 110 | 1.0 | 4:1 | 44 |
| 7 | 84 | 165 | 1.0 | 4:1 | 66 |
| 8 | 80 | 220 | 1.0 | 4:1 | 12 |

FIG. 6 represents the GLC profile for the reaction product of Example III containing compounds defined according to the generic structure:

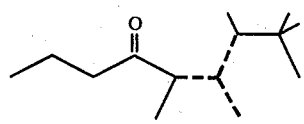

wherein in each of the molecule of the mixture, one of the dashed lines represents a carbon-carbon double bond and the other of the dashed lines represents carbon-carbon single bonds.

FIG. 7 represents the infra-red spectrum for the reaction product of Example III containing the compounds having the structures:

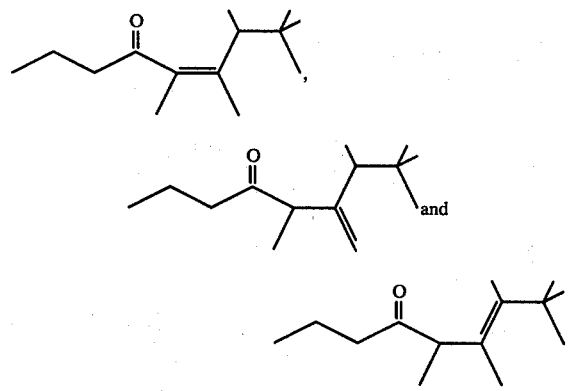

FIG. 8 represents the mass spectrum for the reaction product of Example III containing the compound having the structures:

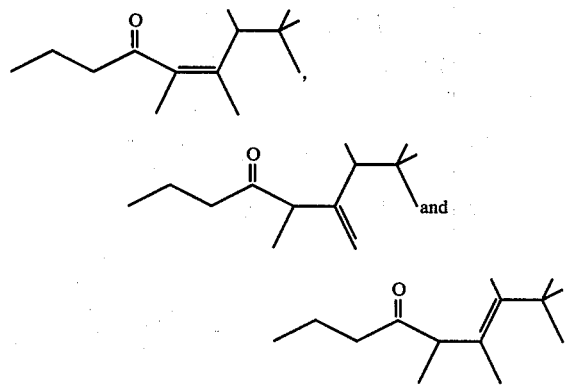

EXAMPLE IV

PREPARATION OF ISOBUTYRYL DERIVATIVE OF DIISOAMYLENE

Reaction:

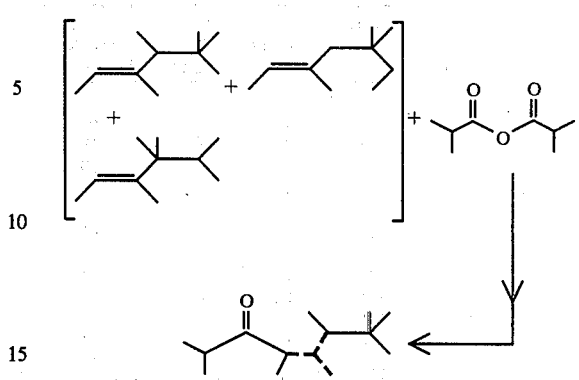

wherein in each of the structures containing dashed lines, these structures represent mixtures of molecules wherein in each of the molecules, one of the dashed lines represents a carbon-carbon double bond and each of the other of the dashed lines represent carbon-carbon single bonds.

Into a 5-liter reaction flask, equipped with reflux condenser, addition funnel, thermometer, Thermowatch, heating mantle and nitrogen purge accessory is placed 1361 g (8.6 moles) of isobutyric anhydride. 105 ml (0.86 moles) of boron trifluoride etherate is then added to the isobutyric anhydride. The resulting mixture is then heated to 65° C. Over a period of 4 hours, 1725 g (8.6 moles) of diisoamylene prepared according to the illustration of Example A is added to the reaction mass, while maintaining the reaction mass at a temperature of 83°-85° C.

The reaction mass is then cooled to room temperature and is added to a 5-liter separatory funnel. 75 ml of 50% sodium hydroxide (aqueous) and 100 ml water is then added to the reaction mass thus yielding two phases, an aqueous phase and an organic phase. The lower aqueous phase is removed and the organic phase is washed as follows:

A—1 liter saturated sodium chloride
B—1 liter 5% aqueous sodium hydroxide
C—1 liter saturated sodium chloride
D—1 liter 12.5% sodium hydroxide
E—1 liter 12.5% sodium hydroxide The reaction mass is then distilled on a two inch splash column packed with stones yielding the following fractions:

| Fraction No. | Vapor Temp. (°C.) | Liquid Temp. (°C.) | mm/Hg Pressure | Weight of Fraction (g.) |
|---|---|---|---|---|
| 1 | 29/54 | 54/68 | 29/24 | Starting Material |
| 2 | 51 | 68 | 14 | " |
| 3 | 90 | 68 | 11 | " |
| 4 | 64 | 98 | 11 | " |
| 5 | 92/94 | 102/108 | 7/5 | 378 |
| 6 | 135 | 165 | 5 | 257 |

Fractions 5 and 6 of the resulting distillate are then bulked and redistilled yielding the following fractions:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 15/45 | 88/92 | 3/2.5 | 4:1 | 21 |
| 2 | 60 | 99 | 2.4 | 4:1 | 13 |

-continued

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 3 | 67 | 98 | 2.4 | 4:1 | 35 |
| 4 | 69 | 97 | 2.2 | 4:1 | 49 |
| 5 | 70 | 99 | 2.2 | 4:1 | 59 |
| 6 | 70 | 101 | 2.2 | 4:1 | 50 |
| 7 | | 101 | 2.0 | 4:1 | 37 |
| 8 | 84 | 112 | 1.7 | 4:1 | 33 |
| 9 | 84 | 112 | 1.7 | 4:1 | 63 |
| 10 | 78 | 119 | 1.8 | 4:1 | 37 |
| 11 | 84 | 122 | 1.7 | 4:1 | 51 |
| 12 | 92 | 121 | 1.7 | 4:1 | 43 |
| 13 | 101 | 156 | 1.6 | 4:1 | 27 |
| 14 | 121 | 178 | 1.6 | 4:1 | 85 |
| 15 | 110 | 220 | 1.6 | 4:1 | 33 |

Fractions 3–9 of this distillation are then rebulked and redistilled on a 12 inch Goodloe Silver Mirror column yielding the following fractions:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 47/60 | 84/92 | 1.6/1.2 | 4:1 | |
| 2 | 67 | 93 | 1.2 | 4:1 | 50 |
| 3 | 67 | 94 | 1.2 | 4:1 | 50 |
| 4 | 67 | 95 | 1.2 | 4:1 | 52 |
| 5 | 67 | 95 | 1.2 | 4:1 | 50 |
| 6 | 67 | 98 | 1.2 | 4:1 | 57 |
| 7 | 67 | 101 | 1.2 | 4:1 | 57 |
| 8 | 72 | 212 | 1.2 | 4:1 | 42 |

The resulting reaction product is analyzed by means of GLC, NMR, IR and mass spectral analyses and this confirms that the reaction product is a mixture of compounds defined according to the generic structure:

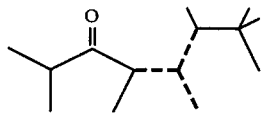

wherein in each of the molecules, one of the dashed lines is a carbon-carbon double bond and the other two of the dashed lines represent carbon-carbon single bonds. The major components of this mixture are compounds having the structures:

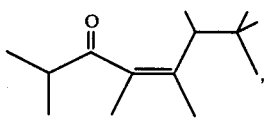

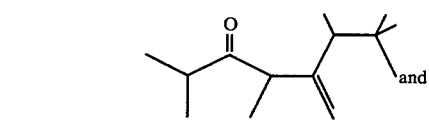

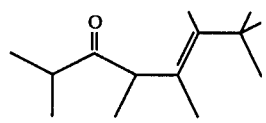

FIG. 9 represents the GLC profile for the reaction product of Example IV, containing a mixture of compounds, each of which is defined according to the generic structure:

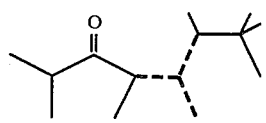

wherein in each of the molecules, one of the dashed lines represents a carbon-carbon double bond and each of the other of the dashed lines represent carbon-carbon single bonds.

FIG. 10 represents the infra-red spectrum for the reaction product of Example IV containing the compounds having the structures:

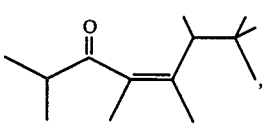

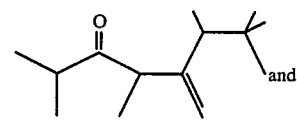

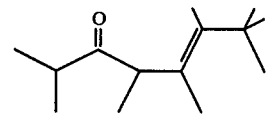

FIG. 11 represents the mass spectrum for the reaction product of Example IV containing the compounds having the structures:

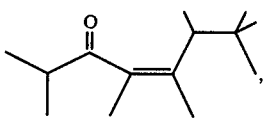

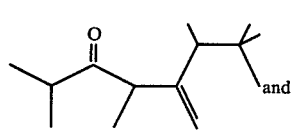

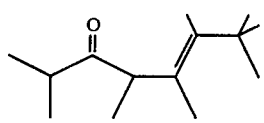

EXAMPLE V

PREPARATION OF ACETYL DERIVATIVE OF DIISOAMYLENE

Reaction:

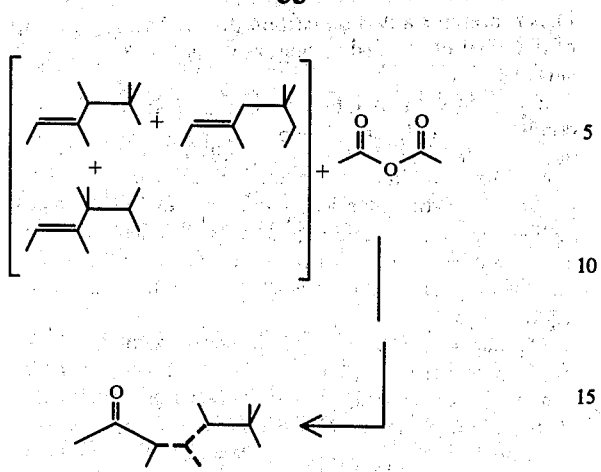

EXAMPLE VA

Into a 5-liter reaction flask equipped with electric stirrer, thermometer, addition funnel, 24/42 y-tube, condenser, heating mantle and nitrogen purge accessories are added 41 ml of 70% methane sulfonic acid followed by 30 g of phosphorous pentoxide. The resulting mixture exotherms to 60° C.

Over a period of 7 minutes, 235 ml acetic anhydride is added to the reaction mass while maintaining same at a temperature of 65° C. Over a period of 30 minutes while maintaining the reaction temperature at 80° C., 516 ml of diisoamylene prepared according to the illustration of Example A is added dropwise to the reaction mass. At the end of the addition of the diisoamylene, GLC analysis indicates 42% product.

The reaction mass is added to a 5 gallon open head separatory flask containing 1 liter of water.

The resulting mixture is washed with 1 liter of 12% sodium hydroxide followed by 1 liter of saturated sodium chloride solution. 100 ml toluene is added to help separation.

GLC, NMR, IR and mass spectral analyses yield the information that the resulting organic phase is a mixture of compounds defined according to the generic structure:

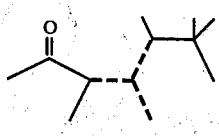

wherein in each of the molecules one of the dashed lines is a carbon-carbon double bond and the other two of the dashed lines represent carbon-carbon single bonds.

The resulting reaction product is then dried over anhydrous magnesium sulfate and distilled on a 3-inch stone column yielding the following fractions:

| Fraction No. | Vapor Temp. (°C.) | Liquid Temp. (°C.) | mm/Hg Pressure |
|---|---|---|---|
| 1 | 65/65 | 103/92 | 113/35 |
| 2 | 60 | 80 | 1 |
| 3 | 52 | 89 | 1 |
| 4 | 61 | 134 | 1 |
| 5 | 73 | 140 | 1 |

Fraction 2, 3 and 4 are bulked and evaluated for their organoleptic properties.

FIG. 12 represents the GLC profile for the reaction product of Example VA containing structures defined according to the genus having the structure:

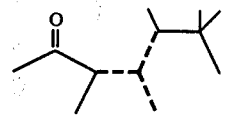

wherein in each of the molecules of the mixture, one of the dashed lines represents a carbon-carbon double bond and each of the other of the dashed lines represent carbon-carbon single bonds.

EXAMPLE VB

To a 500 ml reaction flask equipped with reflux condenser, addition funnel, thermometer, Thermowatch, heating mantle, cooling bath and nitrogne purge accessories, is added 406 ml of acetic anhydride and 30 ml boron trifluoride etherate. The reaction mass is heated to 60° C. and while maintaining the reaction mass at 60° over a period of 30 minutes, diisoamylene, prepared according to the illustration of Example A is added. The resulting reaction mass is then heated, with stirring at 60° C. for a period of 12 hours. At the end of the 12 hour period, the reaction mass is distilled yielding the following fractions:

| Fraction No. | Vapor Temp. (°C.) | Liquid Temp. (°C.) | mm/Hg pressure | Weight of Fraction (g.) |
|---|---|---|---|---|
| 1 | 50/58 | 60/70 | 2.5 | 330 |
| 2 | 67 | 87 | 1.4 | 329 |
| 3 | 71 | 88 | 3.0 | 65 |
| 4 | 90 | 115 | 3.0 | 195 |

The resulting mass, by GLC, IR, NMR and mass spectral analyses consist of compounds defined according to the generic structure:

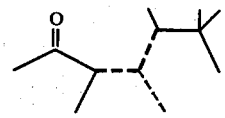

wherein in each of the molecules one of the dashed lines is a carbon-carbon double bond and the other two of the dashed lines represent carbon-carbon single bonds.

FIG. 13 sets forth the GLC profile for the reaction product of this Example VB.

EXAMPLE VI

PREPARATION OF PROPIONYL DERIVATIVE OF DIISOAMYLENE

Reaction:

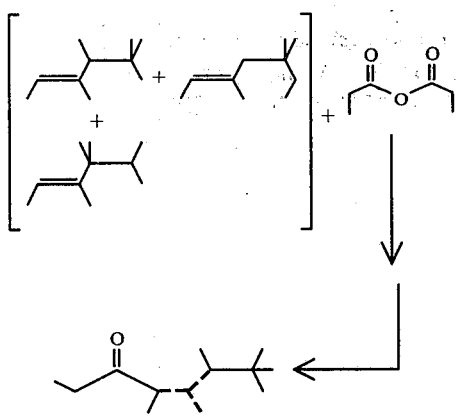

Into 5000 ml reaction flask equipped with reflux condenser, addition funnel, thermometer, Thermowatch, heating mantle, cooling bath and nitrogen purge accessory, is added 415 ml propionic anhydride, 11 g of methane sulfonic acid and 35 ml of boron trifluoride etherate. The reaction mass is heated to 60° C. and over a period of 30 minutes, 1850 ml of diisoamylene prepared according to the illustration of Example A is added. The reaction mass is then stirred at 60° C. for a period of 12 hours. At the end of the 12 hour period, the reaction mass is distilled on a Goodloe fractionation column to yield a mixture of compounds having the generic structure:

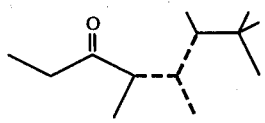

wherein in each of the molecules therein one of the dashed lines represents a carbon-carbon double bond and each of the other of the dashed lines represents a carbon-carbon single bond. The reaction structures are confirmed by GLC, NMR, IR and mass spectral analyses.

EXAMPLE VIIA

PREPARATION OF ISOBUTYRO DERIVATIVE OF DIISOAMYLENE

Reaction:

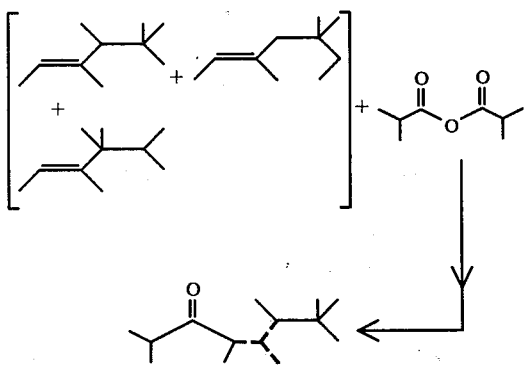

wherein in each of the structures containing dashed lines, these structures represent mixtures of molecules wherein in each of the molecules, one of the dashed lines represents a carbon-carbon double bond and each of the other of the dashed lines represent carbon-carbon single bonds.

Into a 5000 ml reaction flask equipped with reflux condenser, addition funnel, thermometer, Thermowatch, heating mantle, cooling bath and nitrogen gas purge accessory, is added 953 ml (6.0 moles) of isobutyric anhydride; 183 g of polyphosphoric acid and 135 ml 70% methane sulfonic acid. The reaction mass exotherms to 65° C.

Over a period of 20 minutes, while maintaining the reaction mass at 65° C. 1725 g (8.6 moles) of diisoamylene prepared according to the illustration of Example A is added to the reaction mass. The reaction mass is then heated to 85° C. and maintained at that temperature for a period of 10 hours. At the end of the 10 hour period, the reaction mass is cooled and 100 g of sodium acetate and 1 liter of water are added thereto. The resulting mixture is added to a 5 liter separatory funnel and the organic layer is then washed as follows:

A—1 liter 12.5% sodium hydroxide
B—2 liter 12.5% sodium hydroxide
C—1 liter of saturated sodium chloride The reaction mass is then distilled on a 1 foot Goodloe column yielding the following fractions:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 35/50 | 88/93 | 1.8/.08 | 4:1 | 41 |
| 2 | 63 | 100 | .8 | 4:1 | 48 |
| 3 | 63 | 105 | .6 | 4:1 | 73 |
| 4 | 66 | 114 | .6 | 4:1 | 44 |
| 5 | 100 | 145 | .6 | 4:1 | 42 |
| 6 | 101 | 225 | .6 | 4:1 | 29 |

GLC, NMR, IR and mass spectral analyses confirm the information that the resulting product is a mixture of compounds defined according to the generic structure:

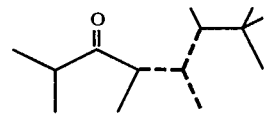

wherein in each molecule of the mixture, one of the dashed lines is a carbon-carbon double bond and the other two of the dashed lines represent carbon-carbon single bonds.

FIG. 14 sets forth the GLC profile for the reaction product of this Example VIIA. (Conditions: SF 96 column, six foot×¼ inch; operated at 180° C. isothermal).

EXAMPLE VIIB

Into a 5000 ml reaction flask equipped with reflux condenser, addition funnel, thermometer, Thermowatch, heating mantle, cooling bath and nitrogen gas purge accessory, is added 953 g (6.0 moles) of isobutyric anhydride and 105 ml (0.86 moles) of boron trifluoride etherate. The reaction mass is heated to 65° C. and over a period of 30 minutes 1725 ml (8.6 moles) of diisoamylene prepared according to the illustration of Example A is added. The reaction mass is then heated to 63°–65°

C. and maintained with stirring at that temperature for a period of 12 hours.

The reaction mass is then cooled to room temperature and 82 g of sodium acetate are added. The reaction mass is then poured into a 5 liter separatory funnel and washed as follows:

A—1 liter water
B—1 liter 12.5% aqueous sodium hydroxide
C—1 liter 12.5% aqueous sodium hydroxide
D—1 liter 12.5% aqueous sodium hydroxide
E—1 liter saturated sodium chloride The organic layer is then dried over anhydrous sodium sulfate and distilled on a 12 inch Goodloe column yielding the following fractions:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 55/67 | 85/92 | 2.4/1.5 | 4:1 | 50 |
| 2 | 72 | 95 | 1.5 | 4:1 | 72 |
| 3 | 73 | 98 | 1.5 | 4:1 | 83 |
| 4 | 75 | 104 | 1.4 | 4:1 | 69 |
| 5 | 80 | 112 | 1.4 | 4:1 | 69 |
| 6 | 80 | 112 | 1.4 | 4:1 | 12 |
| 7 | 108 | 140 | 1.4 | 2:3 | 69 |
| 8 | 116 | 180 | 1.4 | 2:3 | 61 |
| 9 | 110 | 225 | 1.4 | 2:3 | 9 |

GLC, NMR, IR and mass spectral analyses confirm that the resulting product is a mixture of compounds defined according to the generic structure:

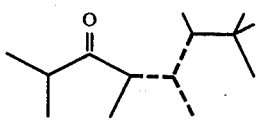

wherein in each of the molecules in the mixture one of the dashed lines represents a carbon-carbon double bond and the other of the dashed lines represent carbon-carbon single bonds.

EXAMPLE VIII

PREPARATION OF n-BUTYRO DIISOAMYLENE AND DERIVATIVES

Reaction:

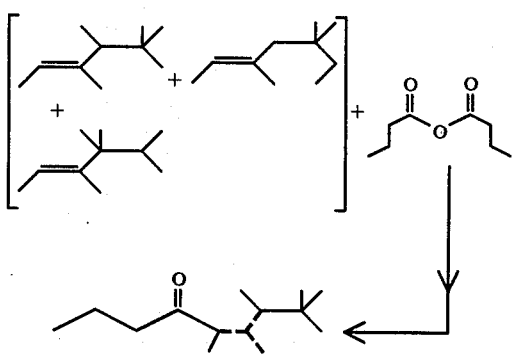

wherein in each of the structures containing dashed lines, these structures represent mixtures of molecules wherein in each of the molecules, one of the dashed lines represents a carbon-carbon double bond and each of the other of the dashed lines represent carbon-carbon single bonds.

Into a 5 liter reaction flask equipped with electric stirrer, thermometer, addition funnel "y" tube, condenser, heating mantle and nitrogen purge accessory are added 55 ml of 70% methane sulfonic acid and 30 g of phosphorous pentoxide. The reaction mass exotherms to 60° C. while maintaining the reaction mass at 65° C. over a period of 10 minutes, 400 ml n-butyric anhydride is added to the reaction mass. Over a period of 40 minutes while maintaining the reaction mass at 84° C., 400 ml of diisoamylene prepared according to the illustration of Example A is added to the reaction mass. The reaction mass is stirred for a period of 4 hours at 84° C.

The reaction mass is then transferred to a 5 gallon open head separatory flask containing 2 liters water. The reaction mass is washed as follows:

A—1 liter 12% sodium hydroxide
B—1 liter saturated sodium chloride solution

The reaction mass is then distilled on a 12 inch Goodloe Silver Mirror column to yield a mixture of compounds defined according to the generic structure:

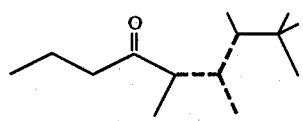

wherein in each of the molecules of the mixture, one of the dashed lines represents carbon-carbon double bond and the other of the dashed lines represent carbon-carbon single bonds. The foregoing is confirmed by GLC, NMR, IR and mass spectral analyses.

EXAMPLE IX

The unsaturated branched-chain ketones produced according to Examples I-VI have very long lasting sweet, rich, warm, woody, fruity, amber, rum/cognac-like, sandalwood-like, sweet floral, vetiver-like aroma nuances which may be utilized to a great extent in inexpensive, functional products. The following pine fragrance demonstrates the use of these materials in perfume compositions. In each of the cases the unsaturated branched-chain ketones are used in an amount of 47.9%:

|                                      | Parts by Weight Example |      |      |      |      |      |
|--------------------------------------|------|------|------|------|------|------|
| Ingredients                          | IXA  | IXB  | IXC  | IXD  | IXE  | IXF  |
| Isobornyl acetate                    | 100  | 100  | 100  | 100  | 100  | 100  |
| Camphor                              | 10   | 10   | 10   | 10   | 10   | 10   |
| Terpineol                            | 25   | 25   | 25   | 25   | 25   | 25   |
| Fir Balsam Absolute (50% in Diethyl Phthalate | 20 | 20 | 20 | 20 | 20 | 20 |
| Coumarin                             | 4    | 4    | 4    | 4    | 4    | 4    |
| Linalool                             | 30   | 30   | 30   | 30   | 30   | 30   |
| Anethol                              | 2    | 2    | 2    | 2    | 2    | 2    |
| Fenchyl Alcohol                      | 10   | 10   | 10   | 10   | 10   | 10   |
| Lemon Terpenes Washed                | 50   | 50   | 50   | 50   | 50   | 50   |
| Borneol                              | 5    | 5    | 5    | 5    | 5    | 5    |
| Galbanum Oil                         | 5    | 5    | 5    | 5    | 5    | 5    |
| Turpentine Russian                   | 150  | 150  | 150  | 150  | 150  | 150  |
| Pinus Pumilionus                     | 50   | 50   | 50   | 50   | 50   | 50   |
| Eucalyptol                           | 50   | 50   | 50   | 50   | 50   | 50   |
| 2,2,6-trimethyl-1-cyclo-hexene-1-carboxaldehyde | 5 | 5 | 5 | 5 | 5 | 5 |
| Maltol 1% in Diethyl Phthalate       | 5    | 5    | 5    | 5    | 5    | 5    |

Product produced according to Ex. I, a mixture of products defined by the structure:

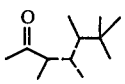

wherein in each of the molecules, one of the dashed lines is a carbon-carbon double bond and the other of the dashed lines is a carbon-carbon single bond.

| | 479 | 0 | 0 | 0 | 0 | 0 |

Product produced according to Ex. II containing the mixture of compounds defined according to the structure:

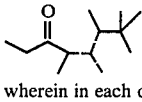

wherein in each of the molecules, one of the dashed lines is a carbon-carbon double bond and the other of the dashed lines is a carbon-carbon single bond.

| | 0 | 479 | 0 | 0 | 0 | 0 |

Product produced according to Ex. III, containing a mixture of compounds defined according to the structure:

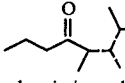

wherein in each of the molecules, one of the dashed lines is a carbon-carbon double bond and the other of the dashed lines is a carbon-carbon single bond.

| | 0 | 0 | 479 | 0 | 0 | 0 |

Product of Ex. IV, being a mixture defined according to the structure:

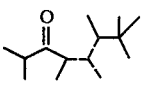

wherein in each of the molecules, one of the dashed lines is a carbon-carbon double bond and the -continued

| Ingredients | Parts by Weight Example | | | | | |
|---|---|---|---|---|---|---|
| | IXA | IXB | IXC | IXD | IXE | IXF |
| other of the dashed lines is a carbon-carbon single bond. | 0 | 0 | 0 | 479 | 0 | 0 |
| Product produced according to Ex. V, being a mixture defined according to the structure: 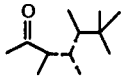 wherein in each of the molecules, one of the dashed lines is a carbon-carbon double bond and the other of the dashed lines is a carbon-carbon single bond. | 0 | 0 | 0 | 0 | 479 | 0 |
| Product produced according to Ex. VI, being a mixture of compounds defined according to the structure: 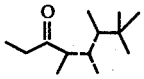 wherein in each of the molecules, one of the dashed lines is a carbon-carbon double bond and the other of the dashed lines is a carbon-carbon single bond. | 0 | 0 | 0 | 0 | 0 | 479 |

The presence of the various unsaturated branched-chain ketones of my invention, supports various notes as indicated below, and produces a considerable savings in the cost of the formulations.

| Example | Additional Nuances Added to the Piney, Herbaceous Aroma of the Fragrance |
|---|---|
| IXA | Fruity, woody and amber |
| IXB | Sweet, floral, fruity and woody/amber |
| IXC | Fruity and woody |
| IXD | A long-lasting sweet, rich warm woody, vetiver-like, fruity aroma |
| IXE | A warm woody, amber aroma with patchouli top-notes and minty undertones |
| IXF | A rum/cognac-like, amber, woody, sandalwood-like aroma |

EXAMPLE X

PREPARATION OF A COSMETIC POWDER PREPARATION

A cosmetic powder is prepared by mixing in a ball mill, 100 g. of talcum powder with 0.25 g of one of the substances set forth in Table II below. The resulting cosmetic powder has a pleasant aroma as set forth in Table II below.

TABLE II

| Structure | |
|---|---|

TABLE II-continued

| of Reaction Product | Fragrance Properties |
|---|---|
| 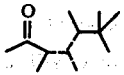 prepared according to Ex. V(B) (mixture of compounds wherein one of the dashed lines in one of the molecules represents a carbon-carbon double bond and each of the other of the dashed lines in that molecule represents a carbon-carbon single bond) | Fruity, woody, and amber aroma |
| 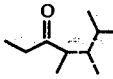 prepared according to Ex. II, | Sweet, fruity floral, woody amber aroma |
| 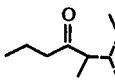 prepared according to Ex. III, | A fruity, woody aroma |

TABLE II-continued

| | | |
|---|---|---|
| prepared according to Ex. IV, | A long-lasting, sweet, rich, warm woody, vetiver-like fruity aroma | |
| prepared according to Ex. I, | A warm, woody amber aroma with a patchouli top-note and a minty undertone | |
| prepared according to Ex. VI, | A rum/cognac-like, amber, woody, (sandalwood-like) aroma | |

| Substance | Fragrance Profile |
|---|---|
| Fragrance composition of Example IXA | A piney, herbaceous aroma with fruity, woody, amber nuances |
| Fragrance composition of Example IXB | A piney, herbaceous aroma with sweet, floral, fruity and woody/amber top-notes |
| Fragrance composition of Example IXC | A piney, herbaceous aroma with fruity and woody top-notes |
| Fragrance composition of Example IXD | An intense piney, vetiver-like aroma with sweet, rich, warm, precious woody undertones, and a fruity top-note |
| Fragrance composition of Example IXE | A piney and herbaceous aroma with woody, amber and patchouli top-notes and a minty undertone |
| Fragrance composition of Example IXF | A piney, ambery, woody aroma with a rum/cognac undertone and a sandalwood top-note |

EXAMPLE XI

PERFUMED LIQUID DETERGENT

Concentrated liquid detergents (Lysine salt of n-dodecylbenzene sulfonic acid as more specifically described in U.S. Pat. No. 3,948,818, issued on Apr. 6, 1976) with fragrance profiles as defined in Table III below are prepared containing 0.10%, 0.15%, 0.20%, 0.25%, 0.30% and 0.35% of the substance as set forth in Table III below. They are prepared by adding and homogeneously mixing the appropriate quantity of substance as set forth in Table III below in the liquid detergent. The detergents all possess excellent intense aromas as defined according to the profiles of Table III below, the intensity increasing with greater concentrations of said substance as set forth below in Table III:

TABLE III

| Structure of Reaction Product | Fragrance Properties |
|---|---|
| prepared according to Ex. V(B) (mixture of compounds wherein one of the dashed lines in one of the molecules represents a carbon-carbon double bond and each of the other of the dashed lines in that molecule represents a carbon-carbon single bond) | Fruity, woody, and amber aroma |
| prepared according to Ex. II, | Sweet, fruity floral, woody amber aroma |
| prepared according to Ex. III, | A fruity, woody aroma |
| prepared according to Ex. IV, | A long-lasting, sweet, rich, warm woody, vetiver-like fruity aroma |
| prepared according to Ex. I. | A warm, woody amber aroma with a patchouli top-note and a minty undertone |
| prepared according to Ex. VI, infra | A rum/cognac-like, amber, woody, (sandalwood-like) aroma |

| Substance | Fragrance Profile |
|---|---|
| Fragrance composition of Example IXA | A piney, herbaceous aroma with fruity, woody, amber nuances |
| Fragrance composition of Example IXB | A piney, herbaceous aroma with sweet, floral, fruity and woody/amber nuances |
| Fragrance composition of Example IXC | A piney, herbaceous aroma with fruity and woody top-notes |
| Fragrance composition of Example IXD | An intense piney, vetiver-like aroma with sweet, rich, warm, precious woody undertones, and a fruity top-note |
| Fragrance composition of Example IXE | A piney and herbaceous aroma with woody, amber and patchouli top-notes and a minty undertone |
| Fragrance composition of Example IXF | A piney, ambery, woody aroma with a rum/cognac undertone and a sandalwood top-note |

EXAMPLE XII

PREPARATION OF A COLOGNE AND HANDKERCHIEF PERFUME

Substances set forth in Table IV below are each individually incorporated into colognes at concentrations of 2.0%, 2.5%, 3.0%, 3.5%, 4.0%, 4.5% and 5.0% in (75%, 80%, 85% and 90%, aqueous food grade ethanol); and into handkerchief perfumes at concentrations of 15%, 20%, 25% and 30% (in 95% aqueous food grade ethanol). Distinctive and definitive long-lasting warm aromas as defined according to Table IV below are all imparted to the cologne and to the handkerchief perfumes at all levels as indicated above:

TABLE IV

| Structure of Reaction Product | Fragrance Properties |
|---|---|
| 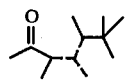<br>prepared according to Ex. V(B) (mixture of compounds wherein one of the dashed lines in one of the molecules represents a carbon-carbon double bond and each of the other of the dashed lines in that molecule represents a carbon-carbon single bond) | Fruity, woody and amber aroma |
| 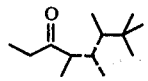<br>prepared according to Ex. II, | Sweet, fruity floral, woody amber aroma |
| 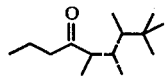<br>prepared according to Ex. III, | A fruity, woody aroma |
| 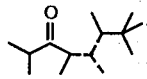<br>prepared according to Ex. IV, | A long-lasting, sweet, rich, warm woody, vetiver-like fruity aroma |
| 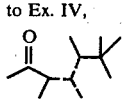<br>prepared according to Ex. I, | A warm, woody amber aroma with a patchouli top-note and a minty undertone |
| 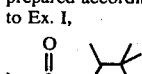<br>prepared according to Ex. VI, infra | A rum/cognac-like, amber, woody, (sandalwood-like) aroma |

| Substance | Frangrance Profile |
|---|---|
| Fragrance composition of Example IXA | A piney, herbaceous aroma with fruity, woody, amber nuances |
| Fragrance composition of Example IXB | A piney, herbaceous aroma with sweet, floral, fruity and woody/amber top-notes |
| Fragrance composition of Example IXC | A piney, herbaceous aroma with fruity and woody top-notes |

TABLE IV-continued

| Fragrnace composition of Example IXD | An intense piney, vetiver-like aroma with sweet, rich, warm, precious woody undertones, and a fruity top-note |
|---|---|
| Fragrance composition of Example IXE | A piney and herbaceous aroma with woody, amber and patchouli top-notes and a minty undertone |
| Fragrance composition of Example IXF | A piney, ambery, woody aroma with a rum/cognac undertone and a sandalwood top-note |

EXAMPLE XIII

PREPARATION OF SOAP COMPOSITION

One hundred grams of soap chips (IVORY®, produced by the Procted & Gamble Company, Cinncinati, Ohio) are admixed with one gram of the substance as set forth in Table V below until homogeneous compositions are obtained. In each of the cases, the homogeneous compositions are heated under three atmospheres pressure at 180° C. for a period of three hours and the resulting liquids are placed into soap molds. The resulting soap cakes, on cooling, manifest excellent, long-lasting, warm aromas as set forth in Table V below:

TABLE V

| Structure of Reaction Product | Fragrance Properties |
|---|---|
| 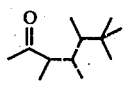<br>prepared according to Ex. V(B) (mixture of compounds wherein one of the dashed lines in one of the molecules represents a carbon-carbon double bond and each of the other of the dashed lines in that molecule represents a carbon-carbon single bond) | Fruity, woody, and amber aroma |
| 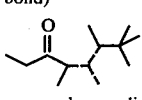<br>prepared according to Ex. II, | Sweet, fruity floral, woody amber aroma |
| 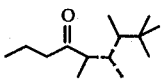<br>prepared according to Ex. III, infra | A fruity, woody aroma |
| 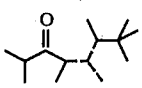<br>prepared according to Ex. IV, infra | A long-lasting, sweet, rich, warm woody, vetiver-like fruity aroma |

TABLE V-continued

| | | |
|---|---|---|
| 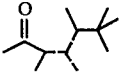<br>prepared according<br>to Ex. I | A warm, woody<br>amber aroma<br>with a pat-<br>chouli top-<br>note and a<br>minty under-<br>tone | |
| 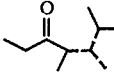<br>prepared according<br>to Ex. VI, infra | A rum/cognac-<br>like, amber,<br>woody, (sandal-<br>wood-like) aroma | |

| Substance | Fragrance Profile |
|---|---|
| Fragrance composition of Example IXA | A piney, herbaceous aroma with fruity, woody, amber nuances |
| Fragrance composition of Example IXB | A piney, herbaceous aroma with sweet, floral, fruity and woody/amber top-notes |
| Fragrance composition of Example IXC | A piney, herbaceous aroma with fruity and woody top-notes |
| Fragrance composition of Example IXD | An intense piney, vetiver-like aroma with sweet, rich, warm, precious woody undertones, and a fruity top-note |
| Fragrance composition of Example IXE | A piney and herbaceous aroma with woody, amber and patchouli top-notes and a minty undertone |
| Fragrance composition of Example IXF | A piney, ambery, woody aroma with a rum/cognac undertone and a sandalwood top-note |

EXAMPLE XIV

PREPARATION OF SOLID DETERGENT COMPOSITIONS

Detergents are prepared from the following ingredients according to Example I of Canadian Patent No. 1,007,948:

| Ingredient | Percent by Weight |
|---|---|
| Neodol ® 45-11 (a C$_{14}$-C$_{15}$ Alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of said detergent is admixed with 0.10, 0.15, 0.20 and 0.25 grams of the substance as set forth in Table VI below. Each of the detergent samples have excellent, warm aromas as indicated in Table VI below:

TABLE VI

| Structure of Reaction Product | Fragrance Properties |
|---|---|
| 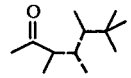 | Fruity, woody, and amber aroma |
| 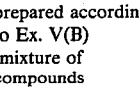<br>prepared according to Ex. V(B) (mixture of compounds wherein one of the dashed lines in one of the molecules represents a carbon-carbon double bond and each of the other of the dashed lines in that molecule represents a carbon-carbon single bond) | Sweet, fruity floral, woody amber aroma |
| 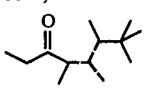<br>prepared according to Ex. II, | A fruity, woody aroma |
| 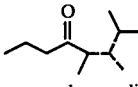<br>prepared according to Ex. III, | A long-lasting, sweet, rich, warm woody, vetiver-like fruity aroma |
| 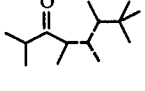<br>prepared according to Ex. IV, | A warm, woody amber aroma with a pat-chouli top-note and a minty under-tone |
| 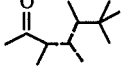<br>prepared according to Ex. I, | A rum/cognac-like, amber, woody, (sandal-wood-like) aroma |
| 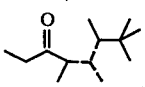<br>prepared according to Ex. VI, | |

| Substance | Fragrance Profile |
|---|---|
| Fragrance composition of Example IXA | A piney, herbaceous aroma with fruity, woody, amber nuances |
| Fragrance composition of Example IXB | A piney, herbaceous aroma with sweet, floral, fruity and woody/amber top-notes |
| Fragrance composition of Example IXC | A piney, herbaceous aroma with fruity and woody top-notes |
| Fragrance composition of Example IXD | An intense piney, vetiver-like aroma with sweet, rich, warm, precious woody undertones, and a fruity top-note |
| Fragrance composition of Example IXE | A piney and herbaceous aroma with woody, amber and patchouli top-notes and a minty undertone |
| Fragrance composition of Example IXF | A piney, ambery, woody aroma with a rum/cognac undertone and a sandalwood top-note |

EXAMPLE XVI

Utilizing the procedure of Example I of column 15 of U.S. Pat. No. 3,632,396, a non-woven cloth substrate useful as a dryer-added fabric softening article of manufacture prepared wherein the substrate, the substrate coating and the outer coating and the perfuming material are as follows:

1. a water "dissolvable" paper ("Dissolvo Paper")
2. Adogen 448 (m.p. about 140° F.) as the substrate coating; and
3. An outer coating having the following formulation (m.p. about 150° F.):
   57 percent $C_{20-22}$ HAPS
   22 percent isopropyl alcohol
   20 percent antistatic agent
   1 percent of one of the substances as set forth in Table VII below.

Fabric softening compositions containing substances as set forth in Table VII below essentially consist of a substrate having a weight of about 3 grams per 100 square-inches of substrate coating, of about 1.85 grams per 100 square inches of substrate, and an outer coating of about 1.4 grams per 100 square inches of substrate, thereby providing a total aromatized substrate and outer coating weight ration of about 1:1 by weight of the substrate. The aromas as set forth in Table VII below, are imparted in a pleasant manner, to the head space in the dryer an operation thereof, using the said dryer-added fabric softening non-woven fabric:

TABLE VII

| Structure of Reaction Product | Fragrance Properties |
|---|---|
| prepared according to Ex. V(B) (mixture of compounds wherein one of the dashed lines in one of the molecules represents a carbon-carbon double bond and each of the other of the dashed lines in that molecule represents a carbon-carbon single bond) | Fruity, woody, and amber aroma |
| prepared according to Ex. II, | Sweet fruity floral, woody amber aroma |
| prepared according to Ex. III, | A fruity, woody aroma |
| prepared according to Ex. IV, infra | A long-lasting, sweet, rich, warm woody, vetiver-like fruity aroma |
| prepared according to Ex. I, infra | A warm, woody amber aroma with a patchouli top-note and a minty undertone |
| prepared according to Ex. VI, infra | A rum/cognac-like, amber, woody, (sandalwood-like) aroma |

| Substance | Fragrance Profile |
|---|---|
| Fragrance composition of Example IXA | A piney, herbaceous aroma with fruity, woody, amber nuances |
| Fragrance composition of Example IXB | A piney, herbaceous aroma with sweet, floral, fruity and woody/amber top-notes |
| Fragrance composition of Example IXC | A piney, herbaceous aroma with fruity and woody top-notes |
| Fragrance composition of Example IXD | An intense piney, vetiver-like aroma with sweet, rich, warm, precious woody undertones, and a fruity top-note |
| Fragrance composition of Example IXE | A piney and herbaceous aroma with woody, amber and patchouli top-notes and a minty undertone |
| Fragrance composition of Example IXF | A piney, ambery, woody aroma with a rum/cognac undertone and a sandalwood top-note |

In the following examples, Aromox® DMC-W and Aromox® DMMC-W are 30% aqueous solutions of dimethyl cocoamine oxide; and Aromox® NCMDW is a 40% aqueous solution of N-cocomorpholine oxide produced by Armac division of AKZO of Chicago, Illinois.

EXAMPLE XVII

Four drops of one of the substances set forth in Table VIII below is added to two grams of Aromox® DMC-W to produce a clear premix. The clear premix is added to 200 grams of CLOROX® with stirring resulting in a clear stable, single phase solution. Sufficient 1 M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry, on dry-out in an atmosphere of 65% relative humidity yields substantially no characteristic "hypochlorite" odor, but does have a faint pleasant aroma as set forth in Table VIII below. Furthermore, no such characteristic "hypochlorite" aroma is retained on the hands of the individual handling such laundry in both the wet and the dry states:

TABLE VIII

| Structure of Reaction Product | Fragrance Properties |
|---|---|

TABLE VIII-continued

| Structure | Fragrance Properties |
|---|---|
| (structure) prepared according to Ex. V(B) (mixture of compounds wherein one of the dashed lines in one of the molecules represents a carbon-carbon double bond and each of the other of the dashed lines in that molecule represents a carbon-carbon single bond) | Fruity, woody, and amber aroma |
| (structure) prepared according to Ex. II, | Sweet, fruity floral, woody amber aroma |
| (structure) prepared according to Ex. III, infra | A fruity, woody aroma |
| (structure) prepared according to Ex. IV, infra | A long-lasting, sweet, rich, warm woody, vetiver-like fruity aroma |
| (structure) prepared according to Ex. I, infra | A warm, woody amber aroma with a patchouli top-note and a minty undertone |

| Substance | Fragrance Profile |
|---|---|
| Fragrance composition of Example IXD | An intense piney, vetiver-like aroma with sweet, rich, warm, precious woody undertones, and a fruity top-note |
| Fragrance composition of Example IXE | A piney and herbaceous aroma with woody, amber and patchouli top-notes and a minty undertone |
| Fragrance composition of Example IXF | A piney, ambery, woody aroma with a rum/cognac undertone and a sandalwood top-note |

EXAMPLE XVIII

Aromox ® DMMC-W in various quantities is mixed with 0.1 grams of one of the substances set forth in Table IX below. The resulting premixes are then added to 200 grams of an aqueous 5% sodium hypochlorite solution. Sufficient 12.5 M aqueous NaOH is added to bring the pH of the mixture up to 13. The following results are obtained:

| Percentage Aromox ® DMMC-W | Clarity of hypochloride solution after addition of premix |
|---|---|
| 0.23% | Clear after three days |
| 0.15% | Clear after three days |
| 0.08% | Initially slightly turbid; two phases exist after three days. |

When the 5% aqueous sodium hypochlorite solution is used as a laundry bleach, the resulting laundry on dry-out, in an atmosphere of 65% relative humidity, yields substantially no characteristic "hypochlorite" odor, but does have a faint, pleasant aroma as set forth in Table IX below. Furthermore, no such characteristic "hypochlorite" aroma is retained on the hands of the individual handling such laundry in both the wet and the dry states:

TABLE IX

| Structure of Reaction Product | Fragrance Properties |
|---|---|
| (structure) prepared according to Ex. V(B) (mixture of compounds wherein one of the dashed lines in one of the molecules represents a carbon-carbon double bond and each of the other of the dashed lines in that molecule represents a carbon-carbon single bond) | Fruity, woody, and amber aroma |
| (structure) prepared according to Ex. II, infra | Sweet, fruity floral, woody amber aroma |
| (structure) prepared according to Ex. III, infra | A fruity, woody aroma |
| (structure) prepared according to Ex. IV, infra | A long-lasting, sweet, rich, warm woody, vetiver-like fruity aroma |
| (structure) prepared according to Ex. I, | A warm, woody amber aroma with a patchouli top-note and a minty undertone |
| (structure) prepared according | A rum/cognac-like, amber, woody, (sandalwood-like) aroma |

TABLE IX-continued to Ex. VI, infra

| Substance | Fragrance Profile |
|---|---|
| Fragrance composition of Example IXA | A piney, herbaceous aroma with fruity, woody, amber nuances |
| Fragrance composition of Example IXB | A piney, herbaceous aroma with sweet, floral, fruity and woody/amber top-notes |
| Fragrance composition of Example IXC | A piney, herbaceous aroma with fruity and woody top-notes |
| Fragrance composition of Example IXD | An intense piney, vetiver-like aroma with sweet, rich, warm, precious woody undertones, and a fruity top-note |
| Fragrance composition of Example IXE | A piney and herbaceous aroma with woody, amber and patchouli top-notes and a minty undertone |
| Fragrance composition of Example IXF | A piney, ambery, woody aroma with a rum/cognac undertone and a sandalwood top-note |

EXAMPLE XIX

Two grams of Aromox® DMMC-W is admixed with eight drops of one of the substances set forth in Table X below. The premix is then added with stirring to 200 grams of a 7% aqueous solution of lithium hypochlorite. Sufficient 3 M aqueous LiOH is added to bring the pH of the solution to 13.4. The mixture is then heated to 120° F. and maintained at that temperature with stirring for a period of 1 week. The resulting solution remains clear in a single phase. When used as a laundry bleach, the resulting bleached laundry, on dry-out in an atmosphere of 50% relative humidity retains a "clean" warm aroma as set forth in Table X below; whereas without the use of the substance set forth in Table X below, the bleached laundry has a faint characteristic disagreeable "hypochlorite" aroma.

TABLE X

| Structure of Reaction Product | Fragrance Properties |
|---|---|
| [structure] prepared according to Ex. V(B) (mixture of compounds wherein one of the dashed lines in one of the molecules represents a carbon-carbon double bond and each of the other of the dashed lines in that molecule represents a carbon-carbon single bond) | Fruity, woody, and amber aroma |
| [structure] | Sweet, fruity floral, woody amber aroma |
| [structure] prepared according to Ex. II, | A fruity, woody aroma |
| [structure] prepared according to Ex. III, | A long-lasting, sweet, rich, warm woody, vetiver-like fruity aroma |
| [structure] prepared according to Ex. IV, | A warm, woody amber aroma with a patchouli top-note and a minty undertone |

| Substance | Fragrance Profile |
|---|---|
| Fragrance composition of Example IXA | A piney, herbaceous aroma with fruity, woody, amber nuances |
| Fragrance composition of Example IXB | A piney, herbaceous aroma with sweet, floral, fruity and woody/amber top-notes |
| Fragrance composition of Example IXC | A piney, herbaceous aroma with fruity and woody top-notes |
| Fragrance composition of Example IXD | An intense piney, vetiver-like aroma with sweet, rich, warm, precious woody undertones, and a fruity top-note |
| Fragrance composition of Example IXE | A piney and herbaceous aroma with woody, amber and patchouli top-notes and a minty undertone |
| Fragrance composition of Example IXF | A piney, ambery, woody aroma with a rum/cognac undertone and a sandalwood top-note |

EXAMPLE XX

Two grams of Aromox® DMMC-W is admixed with eight drops of one of the substance of Table XI below. This premix is then added, with stirring to 200 grams of a mixture containing 4.5% aqueous sodium hypochlorite and 4.5% aqueous lithium hypochlorite. Sufficient 4 M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry on dry-out in an atmosphere of 50% relative humidity retains a "clean fresh" warm aroma as set forth in Table XI below; whereas without the use of the substance set forth in Table XI below, the bleached laundry has a faint characteristic disagreeable "hypochlorite" aroma:

TABLE XI

| Structure of Reaction Product | Fragrance Properties |
|---|---|

TABLE XI-continued

| Structure/Substance | Fragrance Profile |
|---|---|
| [ketone structure] prepared according to Ex. V(B) (mixture of compounds wherein one of the dashed lines in one of the molecules represents a carbon-carbon double bond and each of the other of the dashed lines in that molecule represents a carbon-carbon single bond) | Fruity, woody, and amber aroma |
| [ketone structure] prepared according to Ex. II, | Sweet, fruity floral, woody amber aroma |
| [ketone structure] prepared according to Ex. III, | A fruity, woody aroma |
| [ketone structure] prepared according to Ex. IV, | A long-lasting, sweet, rich, warm woody, vetiver-like fruity aroma |
| [ketone structure] prepared according to Ex. I | A warm, woody amber aroma with a patchouli top-note and a minty undertone |
| [ketone structure] prepared according to Ex. VI, | A rum/cognac-like, amber, woody, (sandalwood-like) aroma |

| Substance | Fragrance Profile |
|---|---|
| Fragrance composition of Example IXA | A piney, herbaceous aroma with fruity, woody, amber nuances |
| Fragrance composition of Example IXB | A piney, herbaceous aroma with sweet, floral, fruity and woody/amber top-notes |
| Fragrance composition of Example IXC | A piney, herbaceous aroma with fruity and woody top-notes |
| Fragrance composition of Example IXD | An intense piney, vetiver-like aroma with sweet, rich, warm, precious woody undertones, and a fruity top-note |
| Fragrance composition of Example IXE | A piney and herbaceous aroma with woody, amber and patchouli top-notes and a minty undertone |
| Fragrance composition of Example IXF | A piney, ambery, woody aroma with a rum/cognac undertone and a sandalwood top-note |

EXAMPLE XXI

Two grams of Aromox ® DMMC-W is admixed with eight drops of one of the substances set forth in Table XII below. This premix is then added with stirring to 200 grams of a mixture containing 4.5% aqueous sodium hypochlorite and 4.5% aqueous lithium hypochlorite. Sufficient 2 M aqueous NaOH is added to bring the pH of the solution to 13.4. The mixture is then heated to 110° F. and maintained at that temperature with stirring for a period of 2 weeks. The resulting solution remains clear as a single phase when used as a laundry bleach. The resulting bleached laundry, on dry-out in an atmosphere of 50% relative humidity, retains an aroma as set forth in Table XII below, whereas without the use of the substance set forth in Table XII below, the bleached laundry has a faint characteristic disagreeable "hypochlorite" aroma.

TABLE XII

| Substance | Fragrance Profile |
|---|---|
| [ketone structure] | A fruity, woody and amber aroma |
| [ketone structure] | A sweet, fruity, floral woody/amber aroma |
| [ketone structure] | A fruity, woody aroma |
| [ketone structure] | A long-lasting, sweet, rich, warm woody, vetiver-like, fruity aroma |
| [ketone structure] | A warm, woody, amber aroma with a patchouli top-note and a minty undertone |
| [ketone structure] | A rum/cognac-like, amber, woody (sandalwood-like) aroma |
| Fragrance composition of Example IXA | A piney, herbaceous aroma with fruity, woody, amber nuances |
| Fragrance composition of Example IXB | A piney, herbaceous aroma with sweet, floral, fruity and woody/amber top-notes |

TABLE XII-continued

| Substance | Fragrance Profile |
| --- | --- |
| Fragrance composition of Example IXC | A piney, herbaceous aroma with fruity and woody top-notes |
| Fragrance composition of Example IXD | An intense piney, vetiver-like aroma with sweet, rich, warm, precious woody undertones, and a fruity top-note |
| Fragrance composition of Example IXE | A piney and herbaceous aroma with woody, amber and patchouli top-notes and a minty undertone |
| Fragrance composition of Example IXF | A piney, ambery, woody aroma with a rum/cognac undertone and a sandalwood top-note |

EXAMPLE XXII

Four drops of one of the substances set forth in Table XIII below is added to 1.5 grams of Aromox® NCMDW to produce a clear premix. The clear premix is added to 200 grams of CLOROX® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant warm, long-lasting aroma as set forth in Table XIII below. Furthermore, no such characteristic "hypochlorite" aroma is retained on the hands of the individual handling such laundry in both the wet and the dry states.

TABLE XIII

| Structure of Reaction Product | Fragrance Properties |
| --- | --- |
| prepared according to Ex. V(B) (mixture of compounds wherein one of the dashed lines in one of the molecules represents a carbon-carbon double bond and each of the other of the dashed lines in that molecule represents a carbon-carbon single bond) | Fruity, woody, and amber aroma |
| prepared according to Ex. II, | Sweet, fruity floral, woody amber aroma |
| prepared according to Ex. III, | A fruity, woody aroma |
| prepared according to Ex. IV, | A long-lasting, sweet, rich, warm woody, vetiver-like fruity aroma |
| prepared according to Ex. I | A warm, woody amber aroma with a patchouli top-note and a minty undertone |
| prepared according to Ex. VI, | A rum/cognac-like, amber, woody, (sandalwood-like) aroma |

| Substance | Fragrance Profile |
| --- | --- |
| Fragrance composition of Example IXA | A piney, herbaceous aroma with fruity, woody, amber nuances |
| Fragrance composition of Example IXB | A piney, herbaceous aroma with sweet, floral, fruity and woody/amber top-notes |
| Fragrance composition of Example IXC | A piney, herbaceous aroma with fruity and woody top-notes |
| Fragrance composition of Example IXD | An intense piney, vetiver-like aroma with sweet, rich, warm, precious woody undertones, and a fruity top-note |
| Fragrance composition of Example IXE | A piney and herbaceous aroma with woody, amber and patchouli top-notes and a minty undertone |
| Fragrance composition of Example IXF | A piney, ambery, woody aroma with a rum/cognac undertone and a sandalwood top-note |

EXAMPLE XXIII

Four drops of one of the substances set forth in Table XIV below is added to 1 gram n-undecyl dimethyl amine oxide to produce a clear premix. The clear premix is added to 200 grams of CLOROX® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant warm aroma as set forth in Table XIV below. Furthermore, no such characteristic "hypochlorite: aroma is retained on the hands of the individual handling such laundry in both the wet and the dry states.

TABLE XIV

| Structure of Reaction Product | Fragrance Properties |
|---|---|
| prepared according to Ex. V(B) (mixture of compounds wherein one of the dashed lines in one of the molecules represents a carbon-carbon double bond and each of the other of the dashed lines in that molecule represents a carbon-carbon single bond) | Fruity, woody, and amber aroma |
| prepared according to Ex. II, | Sweet, fruity floral, woody amber aroma |
| prepared according to Ex. III, | A fruity, woody aroma |
| prepared according to Ex. IV, | A long-lasting, sweet, rich, warm woody, vetiver-like fruity aroma |
| prepared according to Ex. I | A warm, woody amber aroma with a patchouli top-note and a minty undertone |

TABLE XIV-continued

| | |
|---|---|
| prepared according to Ex. VI, | A rum/cognac-like, amber, woody, (sandalwood-like) aroma |

EXAMPLE XXIV

Four drops of one of the substances as set forth in Table XV below are added to 1 gram of n-dodecyl dimethyl amine oxide to produce a clear premix. The clear premix is added to 200 grams of CLOROX® with stirring resulting in a clear, stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite aroma, but does have a warm, pleasant, long-lasting aroma as set forth in Table XV below. Furthermore, no such characteristic "hypochlorite" aroma is retained on the hand of the individual handling such laundry in both the wet and the dry states.

TABLE XV

| Structure of Reaction Product | Fragrance Properties |
|---|---|
| prepared according to Ex. V(B) (mixture of compounds wherein one of the dashed lines in one of the molecules represents a carbon-carbon double bond and each of the other of the dashed lines in that molecule represents a carbon-carbon single bond) | Fruity, woody, and amber aroma |
| prepared according to Ex. II, | Sweet, fruity floral, woody amber aroma |

TABLE XV-continued

| | A fruity, woody aroma |
|---|---|
| prepared according to Ex. III, | |
| | A long-lasting, sweet, rich, warm woody, vetiver-like fruity aroma |
| prepared according to Ex. IV, | |
| | A warm, woody amber aroma with a patchouli top-note and a minty undertone |
| prepared according to Ex. I | |
| | A rum/cognac-like, amber, woody, (sandalwood-like) aroma |
| prepared according to Ex. VI, | |

| Substance | Fragrance Profile |
|---|---|
| Fragrance composition of Example IXA | A piney, herbaceous aroma with fruity, woody, amber nuances |
| Fragrance composition of Example IXB | A piney, herbaceous aroma with sweet, floral, fruity and woody/amber top-notes |
| Fragrance composition of Example IXC | A piney, herbaceous aroma with fruity and woody top-notes |
| Fragrance composition of Example IXD | An intense piney, vetiver-like aroma with sweet, rich, warm, precious woody undertones, and a fruity top-note |
| Fragrance composition of Example IXE | A piney and herbaceous aroma with woody, amber and patchouli top-notes and a minty undertone |
| Fragrance composition of Example IXF | A piney, ambery, woody aroma with a rum/cognac undertone and a sandalwood top-note |

EXAMPLE XXV

One gram of n-tridecyl dimethyl amine oxide is admixed with eight drops of one of the substances as set forth in Table XVI below. This premix is then added with stirring to 200 grams of a 7% aqueous solution of lithium hypochlorite. Sufficient 3 M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry on dry-out in an atmosphere of 50% relative humidity retains a warm, fresh aroma described in Table XVI below; whereas without the use of one of the substances of Table XVI below, the bleached laundry has a faint characteristic disagreeable "hypochlorite" aroma.

TABLE XVI

| Structure of Reaction Product | Fragrance Properties |
|---|---|
| prepared according to Ex. V(B) (mixture of compounds wherein one of the dashed lines in one of the molecules represents a carbon-carbon double bond and each of the other of the dashed lines in that molecule represents a carbon-carbon single bond) | Fruity, woody, and amber aroma |
| prepared according to Ex. II, | Sweet, fruity floral, woody amber aroma |
| prepared according to Ex. III, | A fruity, woody aroma |
| prepared according to Ex. IV, | A long-lasting, sweet, rich, warm woody, vetiver-like fruity aroma |
| prepared according to Ex. I | A warm, woody amber aroma with a patchouli top-note and a minty undertone |
| prepared according to Ex. VI, | A rum/cognac-like, amber, woody, (sandalwood-like) aroma |

| Substance | Fragrance Profile |
|---|---|
| Fragrance composition of Example IXA | A piney, herbaceous aroma with fruity, woody, amber nuances |
| Fragrance composition | A piney, herbaceous aroma |

TABLE XVI-continued

| | |
|---|---|
| of Example IXB | with sweet, floral, fruity and woody/amber top-notes |
| Fragrance composition of Example IXC | A piney, herbaceous aroma with fruity and woody top-notes |
| Fragrance composition of Example IXD | An intense piney, vetiver-like aroma with sweet, rich, warm, precious woody undertones, and a fruity top-note |
| Fragrance composition of Example IXE | A piney and herbaceous aroma with woody, amber and patchouli top-notes and a minty undertone |
| Fragrance composition of Example IXF | A piney, ambery, woody aroma with a rum/cognac undertone and a sandalwood top-note |

EXAMPLE XXVI

A "soft-feel, good-hold" hair spray is produced containing the following ingredients:

| Ingredients | Parts by Weight |
|---|---|
| Polyvinylpyrrilidones/Vinyl acetate "E-735" Copolymer manufactured by the GAF corporation of New York, N.Y. | 4.0 |
| Anhydrous Ethanol | 70.90 |
| Dioctyl Sebecate | 0.05 |
| Benzyl Alcohol | 0.05 |
| "Propellant A46" manufactured by the GAF corporation of New York, N.Y. | 24.95 |
| Fragrance ingredient as set forth in Table XVII below | 0.05 |

PVP/VA copolymers are first dissolved in alcohol and all other ingredients are added until uniform. The propellant is then pressurized and used as an aerosol. The resulting hairspray has a pleasant aroma as set forth in Table XVII below:

TABLE XVII

| Structure of Reaction Product | Fragrance Properties |
|---|---|
| 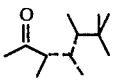 prepared according to Ex. V(B) infra (mixture of compounds wherein one of the dashed lines in one of the molecules represents a carbon-carbon double bond and each of the other of the dashed lines in that molecule represents a carbon-carbon single bond) | Fruity, woody, and amber aroma |
| 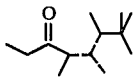 prepared according to Ex. II, infra | Sweet, fruity floral, woody amber aroma |
| 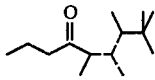 prepared according to Ex. III, infra | A fruity, woody aroma |
| 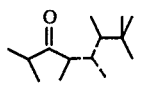 prepared according to Ex. IV, infra | A long-lasting, sweet, rich, warm, woody vetiver-like fruity aroma |
| 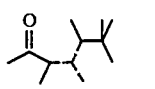 prepared according to Ex. I, infra | A warm, woody amber aroma with a patchouli top-note and a minty undertone |
| 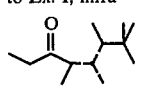 prepared according to Ex. VI, infra | A rum/cognac-like, amber, woody, (sandalwood-like) aroma |

| Substance | Fragrance Profile |
|---|---|
| Fragrance composition of Example IXA | A piney, herbaceous aroma with fruity, woody, amber nuances |
| Fragrance composition of Example IXB | A piney, herbaceous aroma with sweet, floral, fruity and woody/amber top-notes |
| Fragrance composition of Example IXC | A piney, herbaceous aroma with fruity, and woody top-notes |
| Fragrance composition of Example IXD | An intense piney, vetiver-like aroma with sweet, rich, warm, precious woody undertones, and a fruity top-note |
| Fragrance composition of Example IXE | A piney and herbaceous aroma with woody, amber and patchouli top-notes and a minty undertone |
| Fragrance composition of Example IXF | A piney, ambery, woody aroma with a rum/cognac undertone and a sandalwood top-note |

EXAMPLE XXVII

SCOURING CLEANSER COMPOSITION

A scouring cleanser composition is prepared in accordance with Example I, at columns 11 and 12 of U.S. Pat. No. 4,193,888, issued on Mar. 18, 1980. To this composition, a substance as set forth in Table XVIII below is added at the level of 0.250% as set forth in the Table in said Example I of U.S. Pat. No. 4,193,888 yielding an aroma on using said cleanser in ordinary circumstances which is quite pleasant and described in said Table XVIII as set forth below:

TABLE XVIII

| Structure of Reaction Product | Fragrance Properties |
|---|---|
| 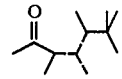 prepared according | Fruity, woody and amber aroma |

TABLE XVIII-continued to Ex. V(B) (mixture of compounds wherein one of the dashed lines in one of the molecules represents a carbon-carbon double bond and each of the other of the dashed lines in that molecule represents a carbon-carbon single bond)

[structure] prepared according to Ex. II, — Sweet, fruity floral, woody amber aroma

[structure] prepared according to Ex. III, — A fruity, woody aroma

[structure] prepared according to Ex. IV, — A long-lasting, sweet, rich, warm woody, vetiver-like fruity aroma

[structure] prepared according to Ex. I — A warm, woody amber aroma with a patchouli top-note and a minty undertone

[structure] prepared according to Ex. VI, — A rum/cognac-like, amber, woody, (sandalwood-like) aroma

| Substance | Fragrance Profile |
| --- | --- |
| Fragrance composition of Example IXA | A piney, herbaceous aroma with fruity, woody, amber nuances |
| Fragrance composition of Example IXB | A piney, herbaceous aroma with sweet, floral, fruity and woody/amber top-notes |
| Fragrance composition of Example IXC | A piney, herbaceous aroma with fruity and woody top-notes |
| Fragrance composition of Example IXD | An intense piney, vetiver-like aroma with sweet-rich, warm, precious woody undertones, and a fruity top-note |
| Fragrance composition of Example IXE | A piney and herbaceous aroma with woody, amber and patchouli top-notes and a minty undertone |
| Fragrance composition of Example IXF | A piney, ambery, woody aroma with a rum/cognac undertone and a sandalwood top-note |

EXAMPLE XXVIII

A fabric softening article prepared substantially as set forth in Example VIII of Canadian Pat. No. 1,069,260 is prepared containing 0.21 percent by weight of a perfuming substance as set forth in Table XIX below and yielding on use in a dryer, a faint aroma as set forth in Table XIX below:

TABLE XIX

| Structure of Reaction Product | Fragrance Properties |
| --- | --- |
| [structure] prepared according to Ex. V(B) infra (mixture of compounds wherein one of the dashed lines in one of the molecules represents a carbon-carbon double bond and each of the other of the dashed lines in that molecule represents a carbon-carbon single bond) | Fruity, woody, and amber aroma |
| [structure] prepared according to Ex. II, infra | Sweet, fruity floral, woody amber aroma |
| [structure] prepared according to Ex. III, infra | A fruity, woody aroma |
| [structure] prepared according to Ex. IV, infra | A long-lasting, sweet, rich, warm woody, vetiver-like fruity aroma |
| [structure] prepared according to Ex. I, infra | A warm, woody amber aroma with a patchouli top-note and a minty undertone |
| [structure] prepared according to Ex. VI, infra | A rum/cognac-like, amber, woody, (sandalwood-like) aroma |

| Substance | Fragrance Profile |
| --- | --- |
| Fragrance composition of Example IXA | A piney, herbaceous aroma with fruity, woody, amber nuances |
| Fragrance composition of Example IXB | A piney, herbaceous aroma with sweet, floral, fruity and woody/amber top-notes |
| Fragrance composition of Example IXC | A piney, herbaceous aroma with fruity and woody top-notes |
| Fragrance composition of Example IXD | An intense piney, vetiver-like aroma with sweet, rich, warm, precious woody undertones, and a fruity top-note |

TABLE XIX-continued

| Fragrance composition of Example IXE | A piney and herbaceous aroma with woody, amber and patchouli top-notes and a minty undertone |
|---|---|
| Fragrance composition of Example IXF | A piney, ambery, woody aroma with a rum/cognac undertone and a sandalwood top-note |

EXAMPLE XXIX

BLUEBERRY FLAVOR FORMULATION

The following formulation is prepared:

| Ingredients | Parts by Weight |
|---|---|
| Heliotropin | 3.0 |
| Terpineol-4 (10% in 95% aqueous food grade ethanol) | 0.2 |
| Benzaldehyde | 1.5 |
| Anisaldehyde | 0.2 |
| Phenyl acetaldehyde | 0.4 |
| Benzyl formate | 0.5 |
| Benzyl acetate | 2.0 |
| Cis-3-hexenyl benzoate (10% in 95% aqueous food grade ethanol) | 0.5 |
| Methyl Hexanoate | 2.0 |
| Hexanal | 1.0 |
| Eucalyptol (1% in 95% aqueous food grade ethanol) | 0.5 |
| Eugenol | 0.2 |
| Acetaldehyde | 3.0 |
| Ethyl acetate | 21.0 |
| Ethyl butyrate | 26.0 |
| Propylene glycol | 38.0 |
|  | 100.0 |

The above formulation is split into two portions. To the first portion is added, at the rate of 1%, the n-butyryl diisoamylene derivative mixture prepared according to Example III, defined according to the structure:

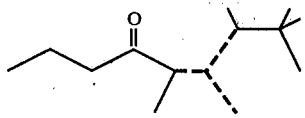

wherein in each of the molecules, one of the dashed lines is a carbon-carbon double bond and the other of the dashed lines is a carbon-carbon single bond. The second portion contains nothing additional added thereto. Both formulations, with and without said n-butyryl diisoamylene derivative prepared according to Example III are combined with water at the rate of 100 ppm. The flavor with the n-butyryl diisoamylene derivative mixture, prepared according to Example II has a more winey, fruity, piney character and is closely similar to the flavor of wild blueberries. It is therefor preferred to the basic blueberry formulation which does not contain said n-butyryl diisoamylene derivative.

EXAMPLE XXX

TOBACCO FILTER

Into a 20 mm cellulose acetate filter is added: the i-butyryl diisoamylene derivative mixture prepared according to Example IV defined according to the generic structure:

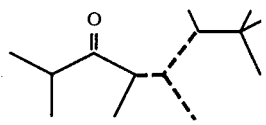

wherein in each of the molecules, one of the dashed lines is a carbon-carbon double bond and the other of the dashed lines is a carbon-carbon single bond. At the rate of 1000 ppm (10 micro liter of a 10% solution of said isobutyryl diisoamylene derivative is added to the filter). The filter is then attached to a full flavor cigarette on the market, e.g. (1) Marlboro ®, (2) Winston ® or (3) viceroy ®, as well as on a Kentucky 1A3 reference cigarette (produced by the University of Kentucky, at Lexington, Kentucky) yielding the following results:

1. Both cigarettes containing the isobutyryl diisoamylene derivative when compared to a cigarette having a filter without said isobutyryl diisoamylene derivative, give rise to a sweet, woody, oriental-like and peppery aroma on smoking, with a pleasant woody, effect and rather noticeable reduced harshness.

2. Both cigarettes containing said isobutyryl diisoamylene derivative mixture, have a lesser degree of "hotness" and give rise to a "Turkish" taste on smoking.

(1) Registered trademark of the Phillip Morris Company.
(2) Registered trademark of the R. J. Reynolds Company.
(3) Registered trademark of the Brown & Williamson Co.

EXAMPLE XXXI

FLAVOR UTILITY OF ISOBUTYRYL DIISOAMYLENE DERIVATIVE MIXTURE PREPARED ACCORDING TO EXAMPLE IV

The following formulation is prepared:

| Ingredients | Parts by Weight |
|---|---|
| Grapefruit oil | 10 |
| Acetaldehyde | 0.6 |
| Alpha-terpinyl | 2.1 |
| Citral | 1.8 |
| Alpha-Terpinene | 0.25 |
| Alpha-fenchyl alcohol | 0.25 |
| Limonene | 0.35 |
| Geranyl acetate | 0.25 |
| Nootkatone | 3.0 |

The flavor formulation is divided into two portions. 40 Parts per million of isobutyryl diisoamylene derivative mixture prepared according to Example IV is added to the first portion and nothing is added to the second portion. A definite aroma improvement, more natural grapefruit juice aroma and taste as well as pleasant sour effect, and generally improved taste is created as a result of the addition of the isobutyryl diisoamylene derivative mixture prepared according to Example IV. In general, the isobutyryl diisoamylene derivatives mixture prepared according to Example IV supplies a natural grapefruit juice note to this grapefruit flavor.

EXAMPLE XXXII

A. POWDER FLAVOR COMPOSITION

20 Grams of the flavor composition of Example XXIX is emulsified in a solution containing 300 gm gum acacia and 700 gm water. The emulsion is spray-dried with a Bowen Lab Model Drier utilizng 260 c.f.m. of air with an inlet temperature of 500° F., an outlet temperature of 200° F. and a wheel speed of 50,000 rpm.

B. SUSTAINED RELEASE FLAVOR

The following mixture is prepared:

| Ingredients | Parts by Weight |
| --- | --- |
| Blueberry Flavor Composition of Example XXIX | 20 |
| Propylene Glycol | 9 |
| Cab-O-Sil ® M-5 (Brand of Silica produced by the Cabot Coprporation of 125 High Street, Boston, Mass. 02110; Physical Properties: Surface area: 200 m²/gm Nominal particle size: 0.012 microns Density: 2.3 lbs/cu. ft. | |

The Cab-O-Sil is dispersed in the liquid blueberry flavor composition of Example XXIX with vigorous stirring, thereby resulting in a viscous liquid. 71 Parts by weight of the powder flavor composition of Part A, supra, is then blended into the said viscous liquid, with stirring at 25° C. for a period of 30 minutes resulting in a dry, free flowing sustained release flavor powder.

EXAMPLE XXXIII

10 Parts by weight of 50 Bloom pigskin gelatin is added to 90 parts by weight of water at a temperature of 150° F. The mixtures is agitated until the gelatin is completely dissolved and the solution is cooled to 120° F. 20 Parts by weight of the liquid flavor composition of Example XXIX is added to the solution which is then homogenized to form an emulsion having particle size typically in the range of 2-5 microns. This material is kept at 120° F. under which conditions the gelatin will not jell.

Coascervation is induced by adding, slowly and uniformly 40 parts by weight of a 20% aqueous solution of sodium sulphate. During coascervation the gelatin molecules are deposited uniformly about each oil droplet as a nucleus.

Gelation is effected by pouring the heated coascervate mixture into 1,000 parts by weight of 7% aqueous solution of sodium sulphate at 65° F. The resulting jelled coascervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE XXXIV

CHEWING GUM

100 Parts by weight of chicle are mixed with 4 parts by weight of the flavor prepared in accordance with Example XXXII. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting blueberry flavor.

EXAMPLE XXXV

CHEWING GUM

100 Parts by weight of chicle are mixed with 18 parts by weight of the flavor prepared in accordance with Example XXXIII. 300 Parts of sucrose and 100 parts of corn syrup are then added. Mixing is effected in a ribbon blender with jacketed side walls of the type manufactured by the Baker Perkings Co.

The resultant chewing gum blend is then manufactured into strips 1 inch in width and 0.1 inches in thickness. The strips are cut into lengths of 3 inches each. On chewing, the chewing gum has a pleasant, long lasting blueberry flavor.

EXAMPLE XXXVI

TOOTHPASTE FORMULATION

The following separate groups of ingredients are prepared:

| Parts by Weight | Ingredients |
| --- | --- |
| Group "A" | |
| 30.200 | Glycerine |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosintae (foaming agent) |
| Group "D" | |
| 1.200 | Flavor Material of Example XXXII |
| 100.00 (Total) | |

PROCEDURE

1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing, until a homogeneous paste is formed.
4. With stirring, the flavor of "D" is added and lastly the sodium n-lauroyl sarcosinate.
5. The resultant slurry is then blended for one hour.

The completed paste is then transferred to a three roller mill and then homogenized, and finally tubed.

The resulting toothpaste when used in a normal toothbrushing procedure yields a pleasant blueberry flavor, of constant strong intensith throughout said procedure.

EXAMPLE XXXVII

CHEWABLE VITAMIN TABLETS

The flavor material produced according to the process of Example XXIX is added to a Chewable Vitamin Tablet Formulation at a rate of 10 gm/Kg which chewable vitamin tablet formulation is prepared as follows:

In a Hobart Mixer the following materials are blended to homogeneity:

| | Gms/ 1000 tablets |
|---|---|
| Vitamin C (ascorbic acid) as ascorbic acid-sodium ascorbate mixture 1:1 | 70.00 |
| Vitamin B₁ (thiamine mononitrate) as Rocoat ® thiamine mononitrate 33⅓% (Hoffman La Roche) | 4.0 |
| Vitamin B₂ (riboflavin) as Rocoat ® riboflavin 33⅓% | 5.0 |
| Vitamin B₆ (pyridoxine hydrochloride) as Rocoat ® pyridoxine hydrochloride 33⅓% | 4.0 |
| Niacinamide as Rocoat ® niacinamide 33⅓% | 33.0 |
| Calcium pantothenate | 11.5 |
| Vitamin B₁₂ (cyanocobalamin) as Merck 0.1% in gelatin | 3.5 |
| Vitamin E (dl-alpha tocopheryl acetate) as dry Vitamin E acetate 33⅓% Roche | 6.6 |
| d-Biotin | 0.044 |
| Flavor of Example XXXII | (as indicated above) |
| Certified Lake color | 5.0 |
| Sweetener - sodium saccharin | 1.0 |
| Magnesium stearate lubricant | 10.0 |
| Mannitol q.s. to make | 500.00 |

Preliminary tablets are prepared by slugging with flat-faced punches and grinding the slugs to 14 mesh. 13.5 G dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong blueberry flavor for a period of 12 minutes.

EXAMPLE XXXVIII

CHEWING TOBACCO

Onto 100 pounds of tobacco for chewing (85% Wisconsin leaf and 15% Pennsylvania leaf) the following casing is sprayed at a rate of 30%:

| Ingredients | Parts by Weight |
|---|---|
| Corn Syrup | 60 |
| Licorice | 10 |
| Glycerine | 20 |
| Fig Juice | 4.6 |
| Prune Juice | 5 |
| Flavor Material of Example XXXII | 0.4 |

The resultant product is redried to a moisture content of 20%. On chewing, this tobacco has an excellent substantially consistent, long-lasting licorice nuance in conjunction with the tobacco note.

What is claimed is:

1. A process for augmenting or enhancing the aroma or taste of a foodstuff, chewing gum or toothpaste comprising the step of adding to a foodstuff, toothpaste or chewing gum from 0.05 parts per million up to about 100 parts per million based on the weight of the total foodstuff, chewing gum or toothpaste composition of a product containing a major proportion of a mixture defined according to the structure:

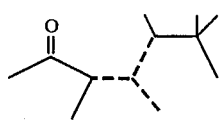

wherein in each of the molecules of the mixture, one of the dashed lines is a carbon-carbon double bond and each of the other of the dashed lines is a carbon-carbon single bond, produced according to the process of:
(i) dimerizing 2-methyl-2-butene in the presence of an acid catalyst to produce a diisoamylene composition;
(ii) reacting the resulting diisoamylene composition with acetic anhydride in the presence of a boron trifluoride diethyletherate catalyst at a reaction temperature of 80°–85° C.; and
(iii) distilling the resulting product at a vapor temperature in the range of from 30° C. up to 80° C. and a pressure of from 3 mm/Hg pressure up to 5 mm/Hg pressure.

2. A process for augmenting or enhancing the aroma or taste of a foodstuff, chewing gum or toothpaste comprising the step of adding to a foodstuff, toothpaste or chewing gum from 0.05 parts per million up to about 100 parts per million based on the weight of the total foodstuff, chewing gum or toothpaste composition of a product containing a major proportion of a mixture defined according to the structure:

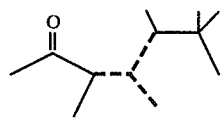

wherein in each of the molecules of the mixture, one of the dashed lines is a carbon-carbon double bond and each of the other of the dashed lines is a carbon-carbon single bond, produced according to the process of:
(i) dimerizing 2-methyl-2-butene in the presence of an acid catalyst to produce a diisoamylene composition;
(ii) reacting the resulting diisoamylene composition with acetic anhydride in the presence of a methane sulfonic acid catalyst at a temperature of 65°–80° C.; and
(iii) distilling the resulting product at a vapor temperature in the range of 52°–61° C.; a liquid temperature in the range of from 80°–134° C. and a pressure of 1 mm/Hg.

3. A process for augmenting or enhancing the aroma or taste of a foodstuff, chewing gum or toothpaste comprising the step of adding to a foodstuff, toothpaste or chewing gum from 0.05 parts per million up to about 100 parts per million based on the weight of the total foodstuff, chewing gum or toothpaste composition of a product containing a major proportion of a mixture defined according to the structure:

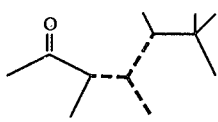

wherein in each of the molecules of the mixture, one of the dashed lines is a carbon-carbon double bond and each of the other of the dashed lines is a carbon-carbon single bond, produced according to the process of:
(i) dimerizing 2-methyl-2-butene in the presence of an acid catalyst to produce a diisoamylene composition;

(ii) reacting the resulting diisoamylene composition with acetic anhydride in the presence of a boron trifluoride diethyletherate catalyst at reaction temperature of 60° C.; and (iii) distilling the resulting product at a vapor temperature in the range of from 50° C. up to 90° C. and a liquid temperature of from 60° C. up to 115° C. and a pressure of from 1.4 up to 3.0 mm/Hg.

4. A process for augmenting or enhancing the aroma or taste of a foodstuff, chewing gum or toothpaste comprising the step of adding to a foodstuff, chewing gum or toothpaste composition from 0.05 parts per million up to about 100 parts per million based on the total weight of foodstuff, toothpaste or chewing gum composition of a mixture containing a major proportion of compounds defined according to the structure:

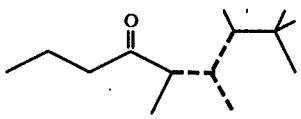

wherein in the mixture, in each of the molecules one of the dashed lines is a carbon-carbon double bond and each of the other of the dashed lines is a carbon-carbon single bond produced according to the process of:

(i) dimerizing 2-methyl-2-butene in the presence of an acid catalyst to form a diisoamylene composition;

(ii) reacting the resulting diisoamylene composition with n-butyric anhydride in the presence of boron trifluoride at a temperature of 65° C.; and (iii) distilling the reaction product at a vapor temperature in the range of from 47° C. up to 84° C.; a liquid temperature of from 105° C. up to 220° C. and a pressure of from 1.0 to 1.8 mm/Hg.

5. A process for augmenting or enhancing the aroma or taste of a foodstuff, chewing gum or toothpaste comprising the step of adding to a foodstuff, chewing gum or toothpaste composition from 0.05 parts per million up to 100 parts per million based on the total composition of said foodstuff, chewing gum or toothpaste composition of a mixture containing a major proportion of compounds defined according to the structure:

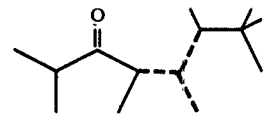

wherein in the mixture, in each of the molecules, one of the dashed lines represents a carbon-carbon double bond and each of the other of the dashed lines represent carbon-carbon single bonds, produced according to the process of:

(i) dimerizing 2-methyl-2-butene in the presence of an acid catalyst to form a diisoamylene composition;

(ii) reacting the resulting diisoamylene composition with isobutyric anhydride in the presence of a boron trifluoride etherate catalyst at a temperature in the range of 65°–85° C.; and (iii) distilling the resulting reaction product at a vapor temperature in the range of from 47° up 72° C.; a liquid temperature in the range of from 84° up to 212° C. and a pressure of from 1.2 up to 1.6 mm/Hg.

* * * * *